United States Patent
Xu et al.

(10) Patent No.: US 7,217,790 B2
(45) Date of Patent: May 15, 2007

(54) UMLR POLYPEPTIDES

(75) Inventors: Wenfeng Xu, Mukilteo, WA (US);
Catherine E. Lofton-Day, Brier, WA (US); Randal M. Henne, Seattle, WA (US); Scott R. Presnell, Tacoma, WA (US); Yue Yao, Kenmore, WA (US); Julia E. Novak, Bainbridge Island, WA (US)

(73) Assignee: ZymoGenetics, Inc., Seattle, WA (US)

( * ) Notice: Subject to any disclaimer, the term of this patent is extended or adjusted under 35 U.S.C. 154(b) by 475 days.

(21) Appl. No.: 10/660,968

(22) Filed: Sep. 12, 2003

(65) Prior Publication Data

US 2004/0063132 A1 Apr. 1, 2004

Related U.S. Application Data

(63) Continuation of application No. 09/695,369, filed on Oct. 23, 2000, now abandoned.

(60) Provisional application No. 60/222,221, filed on Aug. 1, 2000, provisional application No. 60/218,769, filed on Jul. 17, 2000, provisional application No. 60/163,215, filed on Nov. 2, 1999, provisional application No. 60/160,880, filed on Oct. 22, 1999.

(51) Int. Cl.
*C07K 14/00* (2006.01)

(52) U.S. Cl. ...................... 530/350; 536/23.5

(58) Field of Classification Search .................. None
See application file for complete search history.

(56) References Cited

U.S. PATENT DOCUMENTS

2002/0143147 A1 10/2002 Murphy et al. ............ 530/350

2002/0168674 A1 11/2002 Chui et al. .................. 435/6

FOREIGN PATENT DOCUMENTS

| WO | WO 99/11791 | 3/1999 |
| WO | WO 99/13078 | 3/1999 |
| WO | WO 00/01817 | 1/2000 |
| WO | WO 00/39284 | 7/2000 |
| WO | WO200039284 | * 7/2000 |
| WO | WO 00/53758 | 9/2000 |
| WO | WO 00/61757 | 10/2000 |
| WO | WO2003013583 | * 2/2003 |

OTHER PUBLICATIONS

Yan et al., "Two-amino acid molecular switch in an epithelial morphogen that regulates binding to two distinct receptors," Science 290(5491): 523-527, Oct. 2000.
International Search Report for PCT/US00/29304; pages submitted are those identified in the Search Report.
Pro Database Accession No. AF298812, Nov. 2000.
Pro Database Accession No. AAY06400, Valenzuela, D. M., Sep. 1999.
Pro Database Accession No. AAW85724, Jacobs et al, Sep. 1999.
Pro Database Accession No. AAW70386, Tada et al., Dec. 1998.

* cited by examiner

*Primary Examiner*—Eileen B. O'Hara
(74) *Attorney, Agent, or Firm*—Robyn Adams

(57) ABSTRACT

Novel secreted and membrane bound tumor necrosis factor receptor (TNFR) polypeptides, polynucleotides encoding the polypeptides, antibodies and related compositions and methods are disclosed. The polypeptides may be used for detecting ligands, agonists and antagonists. The polypeptides, polynucleotides and antibodies may also be used in methods that modulate inflammation, tumor growth and metastasis, infection, immunity, and cellular maturation.

4 Claims, No Drawings

UMLR POLYPEPTIDES

REFERENCE TO RELATED APPLICATIONS

This application is a continuation of U.S. application Ser. No. 09/695,369, filed Oct. 23, 2000, now abandoned, which claims the benefit of U.S. Provisional Application Ser. No. 60/160,880, filed Oct. 22, 1999, U.S. Provisional Application Ser. No. 60/163,215, filed Nov. 2, 1999, U.S. Provisional Application Ser. No. 60/218,769, filed Jul. 17, 2000, and U.S. Provisional Application Ser. No. 60/222,221, filed Aug. 1, 2000, all of which are herein incorporated by reference.

BACKGROUND OF THE INVENTION

Cellular interactions which occur during an immune response are regulated by members of several families of cell surface receptors, including the tumor necrosis factor receptor (TNFR) family. The TNFR family consists of a number of integral membrane glycoprotein receptors many of which, in conjunction with their respective ligands, regulate interactions between different hematopoietic cell lineages (Smith et al., *The TNF Receptor Superfamily of Cellular and Viral Proteins: Activation, Costimulation and Death*, 76:959–62, 1994; Cosman, *Stem Cells* 12:440–55, 1994).

The TNF receptor family is composed of a number of type I integral membrane glycoproteins which exhibit sequence homology, particularly with respect to cysteine-rich repeats in their extracellular domains. The TNF receptor family includes p75 NGFR (Johnson et al., *Cell* 47:545–54, 1989), p55 TNFR-I (Loetscher et al., *Cell* 61:351–59, 1990), p75 TNFR-II (Schall et al., *Cell* 61:361–70, 1990), TNFR-RP/TNFR-III (Crowe et al. *Science* 264:707–10, 1994), CD27 (Camerini et al., *J. Immunol.* 147:3165–69, 1991), CD30 (Falini et al., *Blood* 85:1–14, 1995), CD40 (Clark and Lane, *Annu. Rev. Immunol.* 9:97–127, 1991), 4-1BB (Kwon and Weissman, *Proc. Natl. Acad. Sci. USA* 86:1963–67, 1989; Schwarz et al., *Gene* 134:295–298, 1993), OX40 (Malletet al., *EMBO J.* 9:1063–68, 1990), FAS/APO-1 (Itoh et al., *Cell* 66:233–43, 1991), DR3 (Chinnaiyan et al., *Science* 274:990–92, 1996) also known as WSL-1 (Kitson et al., *Nature* 384:327–75, 1996), DR4 (Pan et al., *Science* 276: 111–13, 1997), DR5 (Pan et al., *Science* 277:815–8, 1997; Sheridan et al., *Science* 277:818–21, 1997), osteoprotegerin (OPG) (Simonet et al., Cell 89:309–19, 1997; Human Genome Science, WIPO Publication WO96/28546), CAR1, found in chickens (Brojatsch et al., *Cell* 87:845–55, 1996), TRID or DcR1 (Pan et al., *Science* 277:815–8, 1997; Sheridan et al., *Science* 277:818–21, 1997) plus several viral open reading frames encoding TNFR-related molecules. NGFR, TNFR-I, CD30, CD40, 4-1BB, DR3 and OX40 are mainly restricted to cells of the lymphoid/hematopoietic system. TNFR-I, TNFR-II, TNFR-III and DR4 are found in most human tissues.

Members of the TNF receptor family are characterized by a multi-domain structure comprising an extracellular region, a transmembrane domain, a linker region between the extracellular ligand-binding region and the transmembrane domain and a cytoplasmic domain, which in several members of this family (TNFR 1, Fas, DR3, DR4, DR5, CAR1 and low affinity NGFR) contains a death domain associated with apoptosis. One member, TRID or DcR1 (Pan et al., *Science* 277:815–8, 1997; Sheridan et al., ibid.) has a hydrophobic N-terminus with cysteine rich repeats #2 and #3 followed by five tandem repeats of 15 amino acid residues which concludes with a transmembrane domain. The extracellular ligand-binding region is characterized by the presence of one to six cysteine-rich motifs each containing about six cysteines and approximately 40 amino acids, although variation in the size and number of these motifs occurs among members of this family. The cysteine-rich regions provide the motif for binding to shared structures in the ligands. The highest degree of homology among the TNFR family members is within this extracellular cysteine-rich region. Among human TNFRs the average homology is in the range of 25% to 30%. Between the last cysteine-rich repeat and the transmembrane domain is a small spacer region of between 8 to 70 amino acid residues. Cell surface TNF receptors are anchored in the cell membrane by a transmembrane domain characterized by a sequence of hydrophobic amino acid residues. On the opposite end of the protein from the extracellular ligand-binding region and separated from it by the transmembrane domain is the cytoplasmic domain. The cytoplasmic domains of TNFR family members are small, from 46 to 221 amino acid residues, which suggests possible differences in the signaling mechanisms among family members. In the TNF receptor for example, activation is triggered by the aggregation of cytoplasmic domains of three receptors when their corresponding extracellular domains bind to trimeric ligand.

One member of the TNF receptor family, osteoprotegerin (Simonet et al., ibid.), is unique in that it is a secreted protein. Soluble forms of other TNF receptors have been described for TNFR-I, TNFR-II, low-affinity NGFR, FAS, CD27, CD30, CD40 and 4-1BB, but these were generated either by cleaving from the cell membrane or secreted by alternatively spliced mRNA. OPG inhibits osteoclast maturation and it is thought that it might serve to regulate bone density by modulating osteoclast differentiation from hematopoietic precursors. OPG provided protection from normal osteoclast remodeling and ovariectomy-associated bone loss.

Ligands for these receptors have been identified, and with one exception (NGF) belong to the TNF ligand family. The members of the TNF ligand family share approximately 20% sequence identity in the extracellular ligand-binding regions, and exist mainly as type II membrane glycoproteins, biologically active as trimeric or multimeric complexes. This group includes TNF, LT-a, LT-b (Browning et al., *Cell* 72:847–56, 1993), CD27L (Goodwin et al., *Cell* 73:447–56, 1993), CD30L (Smith et al., *Cell* 73:1349–60, 1993), CD40L (Armitage et al., *Nature* 357:80–82, 1992), 4-1BBL (Goodwin et al., *Eur. J, Immunol.* 23:2631–41, 1993), OX40L (Godfrey et al., *J. Exp. Med.* 180:757–62, 1994), TRAIL or apo-2 (Wiley et al., *Immunity* 3:673–82, 1995), TNFg (Human Genome Sciences, WIPO Publication WO96/14328) and FasL (Cosman, ibid., Lotz et al., *J. Leuko. Biol.* 60:1–7, 1996). Soluble ligand forms have been identified for TNF, LT-a and FasL. It is not known whether a specific protease cleaves each ligand, releasing it from the membrane, or whether one protease serves the same function for all TNF ligand family members. TACE (TNF-alpha converting enzyme) has been shown to cleave TNF (Moss et al., *Nature* 385:733–36, 1997; Black et al., *Nature* 385: 729–33, 1997). No other such enzymes are known.

The X-ray crystallographic structures have been resolved for human TNF (Jones et al., *Nature* 338:225–28, 1989), LT-a (Eck et al., *J. Biol. Chem.* 267:2119–122, 1992) and the LT-a/TNFR complex (Banner et al., *Cell* 73:431–45, 1993). This complex features three receptor molecules bound symmetrically to one LT-a trimer. A model of trimeric ligand binding through receptor oligomerization has been proposed to initiate signal transduction pathways. The identification of biological activity of several TNF members has been facilitated through use of monoclonal antibodies specific for the corresponding receptor. These monoclonal antibodies tend to be stimulatory when immobilized and antagonistic in soluble form. This is further evidence that receptor crosslinking is a prerequisite for signal transduction in this receptor family. Importantly, the use of receptor-specific monoclonal antibodies or soluble receptors in the form of multimeric Ig fusion proteins has been useful in determining biological function in vitro and in vivo for several family members. Soluble receptor-Ig fusion proteins have been used successfully in the cloning of the cell surface ligands corresponding to the CD40, CD30, CD27, 4-1BB and Fas receptors.

In general, the members of the tumor necrosis factor ligand family mediate interactions between different hematopoietic cells, such as T cell/B cell, T cell/monocyte and T cell/T cell interactions. The result of this two-way communication can be stimulatory or inhibitory, depending on the target cell or the activation state. These TNF proteins are involved in regulation of cell proliferation, activation and differentiation, including control of cell survival or death by apoptosis or cytotoxicity. One member of this family, OX-40, is restricted to T cells where it acts as a costimulatory receptor. However, among the TNFR family members there are differences in distribution, kinetics of induction and requirements for induction, which support a defined role for each of the ligands in T cell-mediated immune responses.

The demonstrated in vitro and in vivo activities of these TNF receptor ligand family members illustrate the enormous clinical potential of, and need for, other TNF receptors, TNF ligands, TNFR agonists, and TNFR antagonists. The present invention addresses this need by providing a novel TNF receptor and related compositions and methods.

SUMMARY OF THE INVENTION

Within one aspect, the invention provides an isolated polypeptide comprising residues 2 to 129 of SEQ ID NO:2. Within an embodiment, the isolated polypeptide comprises residues 2 to X of SEQ ID NO:2; wherein X is an integer between 130 and 136. Within another embodiment, the isolated polypeptide comprises residues 1 to 129 of SEQ ID NO:2. Within another embodiment, the isolated polypeptide comprises residues 1 to X of SEQ ID NO:2, wherein X is an integer between 130 and 136. Within another embodiment, the isolated polypeptide is selected from the group consisting of: a) polypeptides comprising residues 1 to 161 of SEQ ID NO:2; and b) polypeptides comprising residues 1 to 269 of SEQ ID NO:2.

Within another aspect, the invention provides an isolated polypeptide selected from the group consisting of: a) polypeptides comprising residues 1 to 297 of SEQ ID NO:27; b) polypeptides comprising residues 1 to 267 of SEQ ID NO:29; and c) polypeptides comprising residues 1 to 299 of SEQ ID NO:35.

Within another aspect, the invention provides an isolated polypeptide comprising residues 1 to 173 of SEQ ID NO:38.

Within another aspect, is provided an isolated polypeptide selected from the group consisting of: a) polypeptide molecules comprising residues 1 to 147 of SEQ ID NO:38; b) polypeptide molecules comprising residues 1 to 154 of SEQ ID NO:38; c) polypeptide molecules comprising residues 1 to 163 of SEQ ID NO:38; and d) polypeptide molecules comprising residues 1 to 165 of SEQ ID NO:38.

Within another aspect, the invention provides an isolated polynucleotide that encodes the polypeptide comprising residues 2 to 129 of SEQ ID NO:2. Within an embodiment, the isolated polynucleotide encodes a polypeptide that comprises residues 2 to X of SEQ ID NO:2; wherein X is an integer between 130 and 136. Within another embodiment, the isolated polypeptide encodes a polypeptide that comprises residues 1 to 129 of SEQ ID NO:2. Within another embodiment, the isolated polynucleotide encodes a polypeptide that comprises residues 1 to X of SEQ ID NO:2, wherein X is an integer between 130 and 136. Within another embodiment, the isolated polypeptide encodes a polypeptide that is selected from the group consisting of: a) polypeptides comprising residues 1 to 161 of SEQ ID NO:2; and b) polypeptides comprising residues 1 to 269 of SEQ ID NO:2.

Within another aspect, the invention provides an expression vector comprising the following operably linked elements: a) a transcription promoter; b) a DNA segment wherein the DNA segment is a polynucleotide molecule encoding the polypeptide molecule of comprising residues 1 to 129 of SEQ ID NO:2; and a transcription terminator. Within an embodiment, the DNA segment contains an affinity tag. Within another embodiment, the invention provides a cultured cell into which has been introduced the expression vector, wherein said cell expresses the polypeptide encoded by the DNA segment. Within another embodiment, the invention provides a method of producing a polypeptide comprising culturing the cell, whereby said cell expresses the polypeptide encoded by the DNA segment; and recovering the polypeptide. Within another embodiment, is provided the polypeptide produced by the cell.

Within another aspect, the invention provides a method of detecting lung carcinoma, breast carcinoma, melanoma, osteosarcoma, or lymphoma comprising, contacting said lung carcinoma, breast carcinoma, melanoma, osteosarcoma, or lymphoma with a polynucleotide consisting of the polynucleotide sequence as shown in SEQ ID NOs:1, 31, 32, 33, or 36, wherein the polynucleotide hybridizes to the nucleic acid in the lung carcinoma, breast carcinoma, melanoma, osteosarcoma, or lymphoma. Within an embodiment the polynucleotide is selected from the group consisting of: a polynucleotide consisting of at least 16 contiguous nucleotides as shown in SEQ ID NO:1; a polynucleotide consisting of from 17 to 25 contiguous nucleotides as shown in SEQ ID NO:1; a polynucleotide consisting of 40 contiguous nucleotides as shown in SEQ ID NO:1; a polynucleotide consisting of 60 contiguous nucleotides as shown in SEQ ID NO:1; a polynucleotide consisting of at least 16 contiguous nucleotides as shown in SEQ ID NO:31; a polynucleotide consisting of from 17 to 25 contiguous nucleotides as shown in SEQ ID NO:31; a polynucleotide consisting of 40 contiguous nucleotides as shown in SEQ ID NO:31; a polynucleotide consisting of 60 contiguous nucleotides as shown in SEQ ID NO:31; a polynucleotide consisting of at least 16 contiguous nucleotides as shown in SEQ ID NO:33; a polynucleotide consisting of from 17 to 25 contiguous nucleotides as shown in SEQ ID NO:33; a polynucleotide consisting of 40 contiguous nucleotides as shown in SEQ ID NO:33; a polynucleotide consisting of 60 contiguous nucleotides as shown in SEQ ID NO:33; a polynucleotide consisting of at least 16 contiguous nucleotides as shown in SEQ ID NO:36; a polynucleotide consisting of from 17 to 25 contiguous nucleotides as shown in SEQ ID NO:36; a polynucleotide consisting of 40 contiguous nucleotides as shown in SEQ ID NO:36; a polynucleotide consisting of 60 contiguous nucleotides as shown in SEQ ID NO:36 a polynucleotide encoding a polypeptide consisting of at least 16 contiguous nucleotides as shown in SEQ ID NO:38; a polynucleotide encoding a polypeptide consisting of from 17 to 25 contiguous nucleotides as shown in SEQ ID NO:38; a polynucleotide encoding a polypeptide consisting of 40 contiguous nucleotides as shown in SEQ ID NO:38; a polynucleotide encoding a polypeptide consisting of 60 contiguous nucleotides as shown in SEQ ID NO:38; and a polynucleotide encoding a polypeptide, wherein the polypeptide comprises residues 139 to 297 of SEQ ID NO:27, or residues 139 to 267 of SEQ ID NO:29.

Within another embodiment is method of detecting lung carcinoma, breast carcinoma, melanoma, osteosarcoma, or lymphoma comprising, contacting said lung carcinoma, breast carcinoma, melanoma, osteosarcoma, or lymphoma with an antibody to the polypeptide comprising residues 2 to X wherein x is an integer from 130 to 136. Within an embodiment, the antibody is generated to a polypeptide selected from the group consisting of: a polypeptide comprising residues 4 to 13 of SEQ ID NO:2; a polypeptide comprising residues 17 to 39 of SEQ ID NO:2; a polypeptide comprising residues 44 to 60 of SEQ ID NO:2; a polypeptide comprising residues 69 to 104 of SEQ ID NO:2; a polypeptide comprising residues 106 to 115 of SEQ ID NO:2; a polypeptide comprising 128 to 136 of SEQ ID NO:2; a polypeptide comprising residues 165 to 174 of SEQ ID NO:2; a polypeptide comprising residues 179 to 204 of SEQ ID NO:2; a polypeptide comprising residues 245 to 260 of SEQ ID NO:2; a polypeptide comprising residues 1 to 13 of SEQ ID NO:2; a polypeptide comprising residues 21 to 38 of SEQ ID NO:2; a polypeptide comprising residues 44 to 59 of SEQ ID NO:2; a polypeptide comprising residues 88 to 99 of SEQ ID NO:2; a polypeptide comprising residues 165 to 173 of SEQ ID NO:2; a polypeptide comprising residues 194 to 205 of SEQ ID NO:2; and a polypeptide comprising residues 213 to 221 of SEQ ID NO:2. Within another embodiment the method of detecting lung carcinoma, breast carcinoma, melanoma, osteosarcoma, or lymphoma according to claim 19 wherein the antibody is generated to a polypeptide selected from the group consisting of: a polypeptide comprising residues 181 to 210 of SEQ ID NO:35; a polypeptide comprising residues 219 to 226 of SEQ ID NO:35; a polypeptide comprising residues 218 to 236 of SEQ ID NO:35; a polypeptide comprising residues 162 to 169 of SEQ ID NO:38; a polypeptide comprising residues 149 to 173 of SEQ ID NO:38; a polypeptide comprising residues 194 to 236 of SEQ ID NO:35; a polypeptide comprising residues 150 to 171 of SEQ ID NO:38; a polypeptide comprising residues 230 to 235 of SEQ ID NO:35; and a polypeptide comprising residues 151 to 158 of SEQ ID NO:38. Within another embodiment, the method of detecting lung carcinoma, breast carcinoma, melanoma, osteosarcoma, or lymphoma according to claim 19 wherein the antibody is generated to a polypeptide selected from the group consisting of: a polypeptide consisting of residues 4 to 13 of SEQ ID NO:2; a polypeptide consisting of residues 17 to 39 of SEQ ID NO:2; a polypeptide consisting of residues 44 to 60 of SEQ ID NO:2; a polypeptide consisting of residues 69 to 104 of SEQ ID NO:2; a polypeptide consisting of residues 106 to 115 of SEQ ID NO:2; a polypeptide consisting of 128 to 136 of SEQ ID NO:2; a polypeptide consisting of residues 165 to 174 of SEQ ID NO:2; a polypeptide consisting of residues 179 to 204 of SEQ ID NO:2; a polypeptide consisting of residues 245 to 260 of SEQ ID NO:2; a polypeptide consisting of residues 1 to 13 of SEQ ID NO:2; a polypeptide consisting of residues 21 to 38 of SEQ ID NO:2; a polypeptide consisting of residues 44 to 59 of SEQ ID NO:2; a polypeptide consisting of residues 88 to 99 of SEQ ID NO:2; a polypeptide consisting of residues 165 to 173 of SEQ ID NO:2; a polypeptide consisting of residues 194 to 205 of SEQ ID NO:2; and a polypeptide consisting of residues 213 to 221 of SEQ ID NO:2. Within another embodiment, the method of detecting lung carcinoma, breast carcinoma, melanoma, osteosarcoma, or lymphoma wherein the antibody is generated to a polypeptide selected from the group consisting of: a polypeptide consisting of residues 181 to 210 of SEQ ID NO:35; a polypeptide consisting of residues 219 to 226 of SEQ ID NO:35; a polypeptide consisting of residues 218 to 236 of SEQ ID NO:35; a polypeptide consisting of residues 162 to 169 of SEQ ID O:38; a polypeptide consisting of residues 149 to 173 of SEQ ID NO:38; a polypeptide consisting of residues 194 to 236 of SEQ ID NO:35; a polypeptide consisting of residues 150 to 171 of SEQ ID NO:38; a polypeptide consisting of residues 230 to 235 of SEQ ID NO:35; and a polypeptide consisting of residues 151 to 158 of SEQ ID NO:38.

Within another aspect of the invention, is provided a method of inhibiting the quantity of lung carcinoma, breast carcinoma, melanoma, osteosarcoma, or lymphoma cells expressing a polypeptide selected from the group consisting of: an isolated polypeptide as shown in SEQ ID NO:2; an isolated polypeptide as shown in SEQ ID NO:27; an isolated polypeptide as shown in SEQ ID NO:29; and an isolated polypeptide as shown in SEQ ID NO:35; comprising administering to the cells an isolated polypeptide wherein the isolated polypeptide consists of residues 1 to X of SEQ ID NO:2, wherein X is an integer between 129 and 136. Within another aspect the method uses an isolated polypeptide comprising residues 1 to 173 fo SEQ ID NO:38.

Within another aspect, the invention provides a method of modulating apoptosis of lung carcinoma, breast carcinoma, melanoma, osteosarcoma, or lymphoma cells cells comprising administering to the cells an isolated polypeptide wherein the isolated polypeptide comprising residues 2 to X of SEQ ID NO:2, wherein X is an integer from 129 to 136. Within an embodiment the method of modulating apoptosis of lung carcinoma, breast carcinoma, melanoma, osteosarcoma, or lymphoma cells, uses the isolated polypeptide comprising residues 1 to X, wherein X is an integer from 129 to 136. Within another aspect the method uses an isolated polypeptide comprising residues 1 to 173 of SEQ ID NO:38.

Within another aspect, the invention provides an isolated polypeptide consisting of residues 2 to 129 of SEQ ID NO:2. Within an embodiment, the isolated polypeptide consists of residues 2 to X of SEQ ID NO:2; wherein X is an integer between 130 and 136. Within another embodiment, the isolated consists of residues 1 to 129 of SEQ ID NO:2. Within another embodiment, the isolated polypeptide consists of residues 1 to X of SEQ ID NO:2, wherein X is an integer between 130 and 136. Within another embodiment, the isolated polypeptide is selected from the group consisting of: polypeptides consisting of residues 1 to 161 of SEQ ID NO:2; and polypeptides consisting of residues 1 to 269 of SEQ ID NO:2. Within another embodiment, the isolated polypeptide selected from the group consisting of: polypeptides consisting of residues 1 to 297 of SEQ ID NO:27; polypeptides consisting of residues 1 to 267 of SEQ ID NO:29; and polypeptides consisting of residues 1 to 299 of SEQ ID NO:35.

Within another aspect, the invention provides an isolated polypeptide consisting of residues 1 to 173 of SEQ ID NO:38.

Within another aspect, the invention provides an isolated polypeptide selected from the group consisting of: polypeptide molecules consisting of residues 1 to 147 of SEQ ID NO:38; polypeptide molecules consisting of residues 1 to 154 of SEQ ID NO:38; polypeptide molecules consisting of residues 1 to 163 of SEQ ID NO:38; and polypeptide molecules consisting of residues 1 to 165 of SEQ ID NO:38. Within an embodiment the isolated polynucleotide encodes a polypeptide consisting of residues 2 to 129 of SEQ ID NO:2.

Within one aspect, the invention provides an isolated polypeptide molecule comprising residues 1 to 129 of SEQ ID NO:2. Within an embodiment the isolated polypeptide molecule comprises residues 1 to 136 of SEQ ID NO:2. Within another embodiment the isolated polypeptide molecule comprises residues 1 to 269 of SEQ ID NO:2.

Within another aspect the invention provides an isolated polypeptide molecule selected from the group consisting of: a polypeptide molecule comprising residues 2 to 42 of SEQ ID NO:2; a polypeptide molecule comprising residues 43 to 84 of SEQ ID NO:2; a polypeptide molecule comprising residues 85 to 129 of SEQ ID NO:2; a polypeptide molecule comprising residues 130 to 136 of SEQ ID NO:2; a polypeptide molecule comprising residues 137 to 161 of SEQ ID NO:2; and a polypeptide molecule comprising residues 162 to 269 of SEQ ID NO:2.

Within another aspect the invention provides a isolated polynucleotide molecule encoding a polypeptide molecule wherein the polypeptide molecule comprises residues 1 to 120 of SEQ ID NO:2.

Within another aspect, the invention provides an isolated polynucleotide molecule encoding a polypeptide molecule wherein the polypeptide molecule comprises residues 1 to 136 of SEQ ID NO:2.

Within another aspect of the invention is provided an isolated polynucleotide molecule encoding a polypeptide molecule wherein the polypeptide molecule comprises residues 1 to 269 of SEQ ID NO:2.

Within another aspect, an isolated polynucleotide molecule encoding a polypeptide molecule wherein the polypeptide molecule is selected from the group consisting of: a polypeptide molecule comprising residues 2 to 42 of SEQ ID NO:2; a polypeptide molecule comprising residues 43 to 84 of SEQ ID NO:2; a polypeptide molecule comprising residues 85 to 129 of SEQ ID NO:2; a polypeptide molecule comprising residues 130 to 136 of SEQ ID NO:2; a polypeptide molecule comprising residues 137 to 161 of SEQ ID NO:2; and a polypeptide molecule comprising residues 162 to 269 of SEQ ID NO:2 is provided.

Within another aspect, the invention provides an expression vector comprising the following operably linked elements: a transcription promoter; a DNA segment wherein the DNA segment is a polynucleotide molecule encoding the polypeptide molecule of claim 1; and a transcription terminator. Within an embodiment, the expression vector according contains an affinity tag. Within another embodiment, is provided a cultured cell into which has been introduced the expression vector according, and the cell expresses the polypeptide encoded by the DNA segment. Within a further embodiment, the invention provides a method of producing a polypeptide comprising culturing the cell, whereby said cell expresses the polypeptide encoded by the DNA segment; and recovering the polypeptide.

Within another aspect, the invention provides a method of producing an antibody comprising the following steps in order: inoculating an animal with a polypeptide selected from the group consisting of: a polypeptide molecule consisting of residues 2 to 42 of SEQ ID NO:2; a polypeptide molecule consisting of residues 43 to 84 of SEQ ID NO:2; a polypeptide molecule consisting of residues 85 to 129 of SEQ ID NO:2; a polypeptide molecule consisting of residues 130 to 136 of SEQ ID NO:2; a polypeptide molecule consisting of residues 137 to 161 of SEQ ID NO:2; a polypeptide molecule consisting of residues 162 to 269 of SEQ ID NO:2; a polypeptide molecule consisting of residues 1 to 269 of SEQ ID NO:2; a polypeptide molecule consisting of residues 1 to 129 of SEQ ID NO:2; a polypeptide molecule consisting of residues 1 to 136 of SEQ ID NO:2; and a polypeptide molecule consisting of residues 137 to 269 of SEQ ID NO:2 wherein the polypeptide elicits an immune response in the animal to produce the antibody; and isolating the antibody from the animal. Within an embodiment, the antibody produced by the method binds to a residues 1 to 269 of SEQ ID NO:2. Within an embodiment, is provided the antibody of claim 14, wherein the antibody is a monoclonal antibody. Within an embodiment, the antibody specifically binds to the polypeptide.

Within another aspect, the invention provides a method of producing an antibody comprising the following steps in order: inoculating an animal with an epitope bearing portion of a polypeptide wherein the epitope bearing portion is selected from the group consisting of: a polypeptide molecule consisting of residues 4 to 13 of SEQ ID NO:2; a polypeptide molecule consisting of residues 17 to 39 of SEQ ID NO:2; a polypeptide molecule consisting of residues 44 to 60 of SEQ ID NO:2; a polypeptide molecule consisting of residues 69 to 104 of SEQ ID NO:2; a polypeptide molecule consisting of residues 106 to 115 of SEQ ID NO:2; a polypeptide molecule consisting of residues 128 to 136 of SEQ ID NO:2; a polypeptide molecule consisting of residues 165 to 174 of SEQ ID NO:2; a polypeptide molecule consisting of residues 179 to 204 of SEQ ID NO:2; a polypeptide molecule consisting of residues 245 to 260 of SEQ ID NO:2; a polypeptide molecule consisting of residues 1 to 13 of SEQ ID NO:2; a polypeptide molecule consisting of residues 21 to 38 of SEQ ID NO:2; a polypeptide molecule consisting of residues 44 to 59 of SEQ ID NO:2; a polypeptide molecule consisting of residues 88 to 99 of SEQ ID NO:2; a polypeptide molecule consisting of residues 165 to 173 of SEQ ID NO:2; a polypeptide molecule consisting of residues 213 to 221 of SEQ ID NO:2 wherein the polypeptide elicits an immune response in the animal to produce the antibody; and isolating the antibody from the animal. Within an embodiment, the antibody produced by the method binds to a residues 1 to 269 of SEQ ID NO:2. Within an embodiment, the antibody is a monoclonal antibody. Within an embodiment, the antibody specifically binds to the polypeptide.

Within another aspect, the invention provides a method of forming a reversible peptide-receptor complex comprising; providing a receptor wherein the receptor comprises residues 1 to 129 of SEQ ID NO:2; and contacting the receptor with a peptide; whereby the receptor binds the peptide. Within an embodiment, is provided a method wherein the peptide is selected from the group consisting of: TNF peptides; antibodies; and other binding proteins.

Within another aspect, the invention provides an isolated polypeptide molecule selected from the groups consisting of: a polypeptide molecule comprising residues 1 to 297 of SEQ ID NO:27; and a polypeptide molecule comprising residues 1 to 267 of SEQ ID NO:29. Within an embodiment, the invention provides a polynucleotide encoding the isolated polypeptide.

Within another aspect, the invention provides a method of detecting carcinoma in lung tissue or breast tissue comprising, contacting said carcinoma with a polynucleotide consisting of the polynucleotide sequence as shown in SEQ ID NO:1, wherein the polynucleotide hybridizes to the nucleic acid in the carcinoma tissue. Within an embodiment, the polynucleotide is selected from the group consisting of: a polynucleotide consisting of at least 16 contiguous nucleotides as shown in SEQ ID NO:1; a polynucleotide consisting of from 17 to 25 contiguous nucleotides as shown in SEQ ID NO:1; a polynucleotide consisting of 40 contiguous nucleotides as shown in SEQ ID NO:1; a polynucleotide consisting of 60 contiguous nucleotides as shown in SEQ ID NO:1; a polynucleotide selected from the group consisting of: the polynucleotide as shown in SEQ ID NO:10; the polynucleotide as shown in SEQ ID NO:11; the polynucleotide as shown in SEQ ID NO:12; the polynucleotide as shown in SEQ ID NO:13; the polynucleotide as shown in SEQ ID NO:23; the polynucleotide as shown in SEQ ID NO:24; the polynucleotide as shown in SEQ ID NO:25; and the polynucleotide as shown in SEQ ID NO:26; a polynucleotide encoding a polypeptide, wherein the polypeptide comprises residues 139 to 297 of SEQ ID NO:27, or residues 139 to 267 of SEQ ID NO:29.

Within another aspect, the invention provides a method of detecting carcinoma in lung tissue or breast tissue comprising, contacting said carcinoma with an antibody to the polypeptide as shown in SEQ ID NO:2. Within an embodiment, the antibody is generated to a polypeptide selected from the group consisting of: a polypeptide comprising residues 4 to 13 of SEQ ID NO:2; a polypeptide comprising residues 17 to 39 of SEQ ID NO:2; a polypeptide comprising residues 44 to 60 of SEQ ID NO:2; a polypeptide comprising residues 69 to 104 of SEQ ID NO:2; a polypeptide comprising residues 106 to 115 of SEQ ID NO:2; a polypeptide comprising 128 to 136 of SEQ ID NO:2; a polypeptide comprising residues 165 to 174 of SEQ ID NO:2; a polypeptide comprising residues 179 to 204 of SEQ ID NO:2; a polypeptide comprising residues 245 to 260 of SEQ ID NO:2; a polypeptide comprising residues 1 to 13 of SEQ ID NO:2; a polypeptide comprising residues 21 to 38 of SEQ ID NO:2; a polypeptide comprising residues 44 to 59 of SEQ ID NO:2; a polypeptide comprising residues 88 to 99 of SEQ ID NO:2; a polypeptide comprising residues 165 to 173 of SEQ ID NO:2; a polypeptide comprising residues 194 to 205 of SEQ ID NO:2; and a polypeptide comprising residues 213 to 221 of SEQ ID NO:2. Within another embodiment, the antibody is generated to a polypeptide selected from the group consisting of: a polypeptide consisting of residues 4 to 13 of SEQ ID NO:2; a polypeptide consisting of residues 17 to 39 of SEQ ID NO:2; a polypeptide consisting of residues 44 to 60 of SEQ ID NO:2; a polypeptide consisting of residues 69 to 104 of SEQ ID NO:2; a polypeptide consisting of residues 106 to 115 of SEQ ID NO:2; a polypeptide consisting of 128 to 136 of SEQ ID NO:2; a polypeptide consisting of residues 165 to 174 of SEQ ID NO:2; a polypeptide consisting of residues 179 to 204 of SEQ ID NO:2; a polypeptide consisting of residues 245 to 260 of SEQ ID NO:2; a polypeptide consisting of residues 1 to 13 of SEQ ID NO:2; a polypeptide consisting of residues 21 to 38 of SEQ ID NO:2; a polypeptide consisting of residues 44 to 59 of SEQ ID NO:2; a polypeptide consisting of residues 88 to 99 of SEQ ID NO:2; a polypeptide consisting of residues 165 to 173 of SEQ ID NO:2; a polypeptide consisting of residues 194 to 205 of SEQ ID NO:2; and p) a polypeptide consisting of residues 213 to 221 of SEQ ID NO:2.

Within another aspect of the invention is provided a method of detecting inflamed tissue in lung carcinoma or breast carcinoma comprising, contacting said carcinoma with a polynucleotide consisting of the polynucleotide sequence as shown in SEQ ID NO:1, wherein the polynucleotide hybridizes to the nucleic acid in the inflammed tissue. Within an embodiment, the polynucleotide is selected from the group consisting of: a polynucleotide consisting of at least 16 contiguous nucleotides as shown in SEQ ID NO:1; a polynucleotide consisting of from 17 to 25 contiguous nucleotides as shown in SEQ ID NO:1; a polynucleotide consisting of 40 contiguous nucleotides as shown in SEQ ID NO:1; a polynucleotide consisting of 60 contiguous nucleotides as shown in SEQ ID NO:1; a polynucleotide selected from the group consisting of: the polynucleotide as shown in SEQ ID NO:10; the polynucleotide as shown in SEQ ID NO:11; the polynucleotide as shown in SEQ ID NO:12; the polynucleotide as shown in SEQ ID NO:13; the polynucleotide as shown in SEQ ID NO:23; the polynucleotide as shown in SEQ ID NO:24; the polynucleotide as shown in SEQ ID NO:25; and the polynucleotide as shown in SEQ ID NO:26; a polynucleotide encoding a polypeptide, wherein the polypeptide comprises residues 139 to 297 of SEQ ID NO:27, or residues 139 to 267 of SEQ ID NO:29.

Within another aspect, the invention provides a method of detecting inflamed tissue in lung carcinoma or breast carcinoma comprising, contacting said carcinoma with an antibody to the polypeptide as shown in SEQ ID NO:2. Within an embodiment, the antibody is generated to a polypeptide selected from the group consisting of: a polypeptide comprising residues 4 to 13 of SEQ ID NO:2; a polypeptide comprising residues 17 to 39 of SEQ ID NO:2; a polypeptide comprising residues 44 to 60 of SEQ ID NO:2; a polypeptide comprising residues 69 to 104 of SEQ ID NO:2; a polypeptide comprising residues 106 to 115 of SEQ ID NO:2; a polypeptide comprising 128 to 136 of SEQ ID NO:2; a polypeptide comprising residues 165 to 174 of SEQ ID NO:2; a polypeptide comprising residues 179 to 204 of SEQ ID NO:2; a polypeptide comprising residues 245 to 260 of SEQ ID NO:2; a polypeptide comprising residues 1 to 13 of SEQ ID NO:2; a polypeptide comprising residues 21 to 38 of SEQ ID NO:2; a polypeptide comprising residues 44 to 59 of SEQ ID NO:2; a polypeptide comprising residues 88 to 99 of SEQ ID NO:2; a polypeptide comprising residues 165 to 173 of SEQ ID NO:2; a polypeptide comprising residues 194 to 205 of SEQ ID NO:2; and a polypeptide comprising residues 213 to 221 of SEQ ID NO:2. Within another aspect, the antibody is generated to a polypeptide selected from the group consisting of: a polypeptide consisting of residues 4 to 13 of SEQ ID NO:2; a polypeptide consisting of residues 17 to 39 of SEQ ID NO:2; a polypeptide consisting of residues 44 to 60 of SEQ ID NO:2; a polypeptide consisting of residues 69 to 104 of SEQ ID NO:2; a polypeptide consisting of residues 106 to 115 of SEQ ID NO:2; a polypeptide consisting of 128 to 136 of SEQ ID NO:2; a polypeptide consisting of residues 165 to 174 of SEQ ID NO:2; a polypeptide consisting of residues 179 to 204 of SEQ ID NO:2; a polypeptide consisting of residues 245 to 260 of SEQ ID NO:2; a polypeptide consisting of residues 1 to 13 of SEQ ID NO:2; a polypeptide consisting of residues 21 to 38 of SEQ ID NO:2; a polypeptide consisting of residues 44 to 59 of SEQ ID NO:2; a polypeptide consisting of residues 88 to 99 of SEQ ID NO:2; a polypeptide consisting of residues 165 to 173 of SEQ ID NO:2; a polypeptide consisting of residues 194 to 205 of SEQ ID NO:2; and a polypeptide consisting of residues 213 to 221 of SEQ ID NO:2.

Within another aspect, the invention provides a method of modulating the quantity of cells expressing a polypeptide selected from the group consisting of: a polypeptide comprising the amino acid sequence of SEQ ID NO:1; a polypeptide comprising the amino acid sequence of SEQ ID NO:27; and a polypeptide comprising the amino acid sequence of SEQ ID NO:29, comprising contacting the cells with an antibody generated to the polypeptide as shown in the amino acid sequence of SEQ ID NO:2.

Within another aspect, the invention provides a method of modulating the quantity of cells expressing a polypeptide selected from the group consisting of: a polypeptide comprising the amino acid sequence of SEQ ID NO:1; a polypeptide comprising the amino acid sequence of SEQ ID NO:27; and a polypeptide comprising the amino acid sequence of SEQ ID NO:29, comprising administering to the cells an isolated polypeptide wherein the isolated polypeptide consists of residues 1 to X of SEQ ID NO:2, wherein X is an integer between 129 and 136.

Within another aspect, the invention provides a method of modulating receptor activation in cells comprising administering to the cells an isolated polypeptide, wherein the isolated polypeptide comprises an amino acid as shown in SEQ ID NO:2 from residue 1 to residue X, wherein X is an integer from 129 to 136. Within an embodiment, the cells express a polypeptide sequence selected from the group consisting of: a polypeptide comprising the amino acid sequence of SEQ ID NO:1; a polypeptide comprising the amino acid sequence of SEQ ID NO:27; and a polypeptide comprising the amino acid sequence of SEQ ID NO:29. Within another embodiment, the isolated polypeptide consists of an amino acid as shown in SEQ ID NO:2 from residue 1 to residue X.

Within another aspect of the invention is provided a method of modulating proliferation of carcinoma cells comprising administering to the cells an isolated polypeptide wherein the isolated polypeptide comprises an amino acid as shown in SEQ ID NO:2 from residue 1 to X, wherein X is an integer from 129 to 136. Within an embodiment, the carcinoma cells are lung carcinoma or breast carcinoma cells. Within another embodiment, the isolated polypeptide consists of an amino acid as shown in SEQ ID NO:2 from residue 1 to X.

Within another aspect, the invention provides a method of modulating proliferation of inflammatory cells comprising administering to the cells an isolated polypeptide wherein the isolated polypeptide comprises an amino acid as shown in SEQ ID NO:2 from residue 1 to X, wherein X is an integer from 129 to 136. Within an embodiment, the isolated polypeptide consists of an amino acid as shown in SEQ ID NO:2 from residue 1 to X.

Within another aspect, the invention provides a method of modulating apoptosis of carcinoma cells comprising administering to the cells an isolated polypeptide wherein the isolated polypeptide comprises an amino acid as shown in SEQ ID NO:2 from residue 1 to X, wherein X is an integer from 129 to 136. Within an embodiment, the carcinoma cells are lung carcinoma or breast carcinoma cells. Within another embodiment, the isolated polypeptide consists of an amino acid as shown in SEQ ID NO:2 from residue 1 to X.

Within another aspect, the invention provides a method of modulating apoptosis of inflammatory cells comprising administering to the cells an isolated polypeptide wherein the isolated polypeptide comprises an amino acid as shown in SEQ ID NO:2 from residue 1 to X, wherein X is an integer from 129 to 136. Within an embodiment, the isolated polypeptide consists of an amino acid as shown in SEQ ID NO:2 from residue 1 to X.

These and other aspects of the invention will become evident upon reference to the following detailed description of the invention and attached drawings.

DETAILED DESCRIPTION OF THE INVENTION

Prior to setting forth the invention in detail, it may be helpful to the understanding thereof to define the following terms:

The term "affinity tag" is used herein to denote a polypeptide segment that can be attached to a second polypeptide to provide for purification of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952–4, 1985) (SEQ ID NO:7), substance P, Flag™ peptide (Hopp et al., *Biotechnology* 6:1204–1210, 1988), streptavidin binding peptide, maltose binding protein (Guan et al., *Gene* 67:21–30, 1987), cellulose binding protein, thioredoxin, ubiquitin, T7 polymerase, or other antigenic epitope or binding domain. See, in general, Ford et al., *Protein Expression and Purification* 2: 95–107, 1991. DNAs encoding affinity tags and other reagents are available from commercial suppliers (e.g., Pharmacia Biotech, Piscataway, N.J.; New England Biolabs, Beverly, Mass.; Eastman Kodak, New Haven, Conn.).

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "complements of a polynucleotide molecule" is a polynucleotide molecule having a complementary base sequence and reverse orientation as compared to a reference sequence. For example, the sequence 5' ATGCACGGG 3' is complementary to 5' CCCGTGCAT 3'.

The term "corresponding to", when applied to positions of amino acid residues in sequences, means corresponding positions in a plurality of sequences when the sequences are optimally aligned.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

"Operably linked" means that two or more entities are joined together such that they function in concert for their intended purposes. When referring to DNA segments, the phrase indicates, for example, that coding sequences are joined in the correct reading frame, and transcription initiates in the promoter and proceeds through the coding segment(s) to the terminator. When referring to polypeptides, "operably linked" includes both covalently (e.g., by disulfide bonding) and non-covalently (e.g., by hydrogen bonding, hydrophobic interactions, or salt-bridge interactions) linked sequences, wherein the desired function(s) of the sequences are retained.

The term "ortholog" or "species homolog", denotes a polypeptide or protein obtained from one species that is the functional counterpart of a polypeptide or protein from a different species. Sequence differences among orthologs are the result of speciation.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

A "peptide-receptor complex" is formed when a peptide, or ligand, binds to a receptor resulting in a change in the properties of the receptor. This change can result in an initiation of sequences of reactions leading to a change in cellular function, or the inability of the receptor to bind additional peptides. The forming of a peptide-receptor complex can be reversible.

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-domain or multi-peptide structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

A "segment" is a portion of a larger molecule (e.g., polynucleotide or polypeptide) having specified attributes. For example, a DNA segment encoding a specified polypeptide is a portion of a longer DNA molecule, such as a plasmid or plasmid fragment, that, when read from the 5' to the 3' direction, encodes the sequence of amino acids of the specified polypeptide.

A "soluble receptor" is a receptor polypeptide that is not bound to a cell membrane. Soluble receptors are most commonly ligand-binding receptor polypeptides that lack transmembrane and cytoplasmic domains. Soluble receptors can comprise additional amino acid residues, such as affinity tags that provide for purification of the polypeptide or provide sites for attachment of the polypeptide to a substrate. Many cell-surface receptors have naturally occurring, soluble counterparts that are produced by proteolysis or translated from alternatively spliced mRNAs. Receptor polypeptides are said to be substantially free of transmembrane and intracellular polypeptide segments when they lack sufficient portions of these segments to provide membrane anchoring or signal transduction, respectively.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

Structurally, the TNF receptor family is characterized by an extracellular portion composed of several modules called, historically, "cysteine-rich pseudo-repeats". A prototypical family member has four of these pseudo-repeats, each about 29–43 residues long, one right after the other. A typical pseudo-repeat has 6 cysteine residues. They are called pseudo-repeats because, although they appear to originate from a common ancestral module, they may not repeat exactly. The crystal structure of the p55 TNF receptor revealed that each pseudo-repeat corresponds to one folding domain, and that all four pseudo-repeats fold into the same tertiary structure, held together internally by disulfide bonds.

Four motifs for the pseudo-repeat sequences are shown below. Within in each motif, X represents an amino acid residue, the numbers contained within curly brackets are multipliers for the preceding residue and residues in brackets are optional. Alternative sequences are indicated with asterisks.

```
Pseudo-repeat motif #1 (SEQ ID NO:4)
X-C-X{10-14}-C-C-X-X-C-X{5-9}-C-X{6-8}-C-X Pseudo-repeat motif #2 (SEQ ID NO:5)
X-C-X{13-15}-C-X-X-C-X{2-3}-C-X{8-11}-C-X{7}-C Pseudo-repeat motif #3 (SEQ ID NO:6) and alternative motif (SEQ ID NO:7)
X-C-X{5-6}-X-X{4-9}-C-X-X-C-X{2-7}-C-X{8-9}-C-X{7}-C-(X)
       *                              ***********
       C                              X{10-16}
```

All references cited herein are incorporated by reference in their entirety.

The present invention is based in part upon the discovery of a novel DNA sequences (SEQ ID NOs:1) and corresponding polypeptide sequences (SEQ ID NOs:2) which have homology to members of the tumor necrosis factor receptor family. The receptor has been designated (Uterine Myometrium Lieomyoma Receptor) and is also referred to herein as ztnfr11. Novel UMLR receptor-encoding polynucleotides and polypeptides of the present invention were identified by the discovery of a novel cDNA having homology to tumor necrosis factor receptor family members. Sequence analysis of a deduced amino acid sequence indicates the presence of 2 complete extracellular, cysteine-rich pseudo-repeats (#1, comprises residues 2 to 42, nucleotides 107 to 229; #2 comprises residues 43 to 84 of SEQ ID NO:2, nucleotides 230 to 355 of SEQ ID NO:1), and one partial cysteine-rich pseudo-repeat (#3, comprises residues 85 to approximately 129 of SEQ ID NO:2, nucleotides 356 to approximately 490 of SEQ ID NO:1). Other members of the TNFR superfamily are also known to have partial cysteine-rich repeats. These include APO4 and TRAIL. The membrane-bound form further consists of a linker region (approximately residues 130 to 136 of SEQ ID NO:2, nucleotides 491 to 511 of SEQ ID NO:1), a transmembrane domain (residues 137 to 161 of SEQ ID NO:2, nucleotides 512 to 586 of SEQ ID NO:1) and a cytoplasmic, or signaling, domain (residues 162 to 269 of SEQ ID NO:2, nucleotides 587 to 910 of SEQ ID NO:1). The mature membrane-bound UMLR protein comprises amino acid residue 1 to 269 of SEQ ID NO:2, nucleotides 104 to 913 of SEQ ID NO:1. Those skilled in the art will recognize that these domain boundaries are approximate, and are based on alignments with known proteins and predictions of protein folding. These features indicate that the receptors encoded by the DNA sequences of SEQ ID NO:1 is a member of the TNF receptor family.

Some TNF receptors, such as OX-40, osteoprotegerin and CD-27, do not contain a complete pseudo-repeat #3 as defined in SEQ ID NOs:6 and 7.

```
Pseudo-repeat motif #4 (SEQ ID NO:8) and
alternative motif (SEQ ID NO:9)
X-C-X{10-14}-C-X-X-C-X-X-C-X{4-10}-C-X{3-7}-C-X
                    *                  *
                    X                  X
```

The pseudo-repeat #2 (residues 43 to 84 of SEQ ID NO:2) is encompassed by motif #4 (SEQ ID NO:8). Pseudo-repeats #1 (residues 2 to 42 of SEQ ID NO:2) and #3 (residues 85 to approximately 107 of SEQ ID NO:2) most closely resemble motif #4 (SEQ ID NO:8).

Within UMLR, the region corresponding to pseudo-repeat #1 has conserved cysteine residues at amino acid residues 3, 15, 18, 21, 31 and 41 of SEQ ID NO:2. The region corresponding to pseudo-repeat #2 has conserved cysteine residues at amino acid residues 44, 58, 61, 64, 75 and 83 of SEQ ID NO:2. The region corresponding to pseudo-repeat #3 has conserved cysteine residues at amino acid residues 86, 104, 107 and 118 of SEQ ID NO:2.

The cycteine-rich pseudo-repeats are the known ligand binding sites for TNF ligands. Thus, the amino acid residues of UMLR most likely to be involved in ligand binding are likely to be found within residues 1 to 129 of SEQ ID NO:2.

The cysteine-rich domains (pseudo-repeats) of the extracellular ligand binding region of UMLR are similar to several other members of the TNF receptor family. One member of this family is human APO4. See Chaudhary, WO 99/11791. Human APO4 is expressed in the developing fetus as well as adult, and has been characterized as having apoptotic activity, and the ability to activate the JNK signaling pathway. Additionally, mouse APO4 has two isoforms: one with a short cytoplasmic tail, and the other with a longer cytoplasmic tail. These isoforms are the result of alternative splicing. Additional isoforms of the present invention have been identified as well and include one isoform with an insertion as illustrated by the polypeptide sequence as shown in SEQ ID NO:27. As the insertion in this isoform is in the cytoplamsic domain, the polypeptide as shown in SEQ ID NO:27 may be involved in cell signaling. The other isoform contains this insertion as well as a deletion as illustrated by the polypeptide sequence as shown in SEQ ID NO:29. The deletion in the isoform represented by SEQ ID NO: 29 is in the transmembrane and cytoplasmic domains, and as such may be used as a soluble form of the receptor. An additional sequence identified is SEQ ID NO:38.

OPG is a soluble tumor necrosis factor receptor, which reduces its ligand's concentration in circulation, and regulates osteoclast differentiation and activation (Lacey, D. L., et al., *Cell* 93: 165–176, 1998). UMLR can be a membrane-bound signaling receptor (residues 1 to 269 of SEQ ID NO:2; residues 1 to 297 of SEQ ID NO:27; or residues 1 to 299 of SEQ ID NO:35) or a soluble receptor (residues 1 to approximately 129 of SEQ ID NO:2) which regulate the amount of circulating ligand. The linker region of UMLR (residues 130 to 136 of SEQ ID NO:2) may not be necessary for binding of the receptor to the ligand. Thus, portions of it may be deleted from a construct for the soluble receptor. Therefore, a construct for a soluble receptor can be as short as residues 1 to 129 of SEQ ID NO:2, or as long as residues 1 to 136 of SEQ ID NO:2. An additional sequences for a soluble ztnfr11 sequences are shown in SEQ ID NO:38.

UMLR can act in a manner analogous to hAPO4 but with an independent ligand. Therefore the ligand for UMLR can function in development, in cellular interactions of the uterus, inflammation, and/or abnormal cell growth. However it is likely to be homologous to TNF or NGF, or perhaps have a completely different structure from known TNF ligands.

Analysis of the tissue distribution of UMLR RNA was performed by Northern blot techniques. Two transcripts of approximately 3.5 kb and approximately 4.7 kb were detected corresponding to UMLR in melanoma and tumorous lung cell lines. Additional analyses show UMLR RNA in osteosarcoma cell lines and a lymphoma cell line by RT-PCR, and in breast carcinoma and cutaneous lymphoma tissue by in situ hybridization. As UMLR polypeptides are expressed in osteosarcoma cell lines, which are derived from osteoblasts, molecules of the present invention may be involved in osteoblast differentiation and activation.

The polynucleotides of the present invention were originally discovered in a uterus, myometrium with leiomyoma library. Expression in tumor cells is consistent with other members of the TNFR family that are associated with growth regulation, differentiation and tumorigenesis.

Broad tissue distribution is also not unknown in the TNF receptor family. Several members, TNRFR-I, TNRFR-II, TNRFR-III and DR4, are found in most human tissues. OPG was detected in lung, heart, kidney, placenta, and to a lesser degree, in hematopoietic and immune organs (Simmonet et al., ibid.).

Chromosomal localization of UMLR to Xq11–q12 was determined using radiation hybrid chimeras.

The present invention provides polynucleotide molecules, including DNA and RNA molecules, that encode the UMLR polypeptides disclosed herein. Those skilled in the art will readily recognize that, in view of the degeneracy of the genetic code, considerable sequence variation is possible among these polynucleotide molecules. SEQ ID NO:3 is a degenerate DNA sequence that encompasses all DNAs that encode the UMLR polypeptide of SEQ ID NO:2. SEQ ID NO:28 is a degenerate DNA sequence that encompasses all DNAs that encode the UMLR polypeptide of SEQ ID NO:27. SEQ ID NO:30 is a degenerate DNA sequence that encompasses all DNAs that encode the UMLR polypeptide of SEQ ID NO:29. SEQ ID NO:39 is a degenerate DNA sequence that encompasses all DNAs that encode the UMLR polypeptide of SEQ ID NO:38. Those skilled in the art will recognize that the degenerate sequence of SEQ ID NOs:3, 28, 30, and 39 also provide all RNA sequences encoding SEQ ID NOs:2, 27, 29, and 38, respectively, by substituting U for T. Thus, UMLR polypeptide-encoding polynucleotides comprising nucleotide 1 to nucleotide 1162 of SEQ ID NO:1, nucleotide 1 to nucleotide 891 of SEQ ID NO:28, nucleotide 1 to nucleotide 801 of SEQ ID NO:30, nucleotide 1 to nucleotide 519 of SEQ ID NO:39, and their RNA equivalents are contemplated by the present invention. Table 1 sets forth the one-letter codes used within SEQ ID Nos:3, 28, 30, and 39 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 1

| Nucleotide | Resolution | Nucleotide | Complement |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NOs:3, 28, 30, and 39 encompassing all possible codons for a given amino acid, are set forth in Table 2.

TABLE 2

| Amino Acid | One Letter Code | Codons | | | | | | Degenerate Codon |
|---|---|---|---|---|---|---|---|---|
| Cys | C | TGC | TGT | | | | | TGY |
| Ser | S | AGC | AGT | TCA | TCC | TCG | TCT | WSN |
| Thr | T | ACA | ACC | ACG | ACT | | | CAN |
| Pro | P | CCA | CCC | CCG | CCT | | | CCN |
| Ala | A | GCA | GCC | GCG | GCT | | | GCN |
| Gly | G | GGA | GGC | GGG | GGT | | | GGN |
| Asn | N | AAC | AAT | | | | | AAY |
| Asp | D | GAC | GAT | | | | | GAY |
| Glu | B | GAA | GAG | | | | | GAR |
| Gln | Q | CAA | CAG | | | | | CAR |
| His | H | CAC | CAT | | | | | CAY |
| Arg | R | AGA | AGG | CGA | CGC | CGG | CGT | MGN |
| Lys | K | AAA | AAG | | | | | AAR |
| Met | M | ATG | | | | | | ATG |
| Ile | I | ATA | ATC | ATT | | | | ATH |
| Leu | L | CTA | CTC | CTG | CTT | TTA | TTG | YTN |
| Val | V | GTA | GTC | GTG | GTT | | | GTN |
| Phe | F | TTC | TTT | | | | | TTY |
| Tyr | Y | TAC | TAT | | | | | TAY |

TABLE 2-continued

| Amino Acid | One Letter Code | Codons | Degenerate Codon |
|---|---|---|---|
| Trp | W | TGG | TGG |
| Ter | . | TAA TAG TGA | TRR |
| Asn˜p | B | | RAY |
| Glun | Z | | SAR |
| Any | X | | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequences of SEQ ID NOs:2, 27, 29, 35, and 38. Variant sequences can be readily tested for functionality as described herein.

The present invention further provides polynucleotide molecules, including DNA and RNA molecules, encoding UMLR proteins. The polynucleotides of the present invention include the sense strand; the anti-sense strand; and the DNA as double-stranded, having both the sense and anti-sense strand annealed together by their respective hydrogen bonds. Representative DNA sequences encoding UMLR proteins are set forth in SEQ ID NOs:1, 3, 22, 28, 30, 31, 32, 33, 36, and 39. DNA sequences encoding other UMLR proteins can be readily generated by those of ordinary skill in the art based on the genetic code.

One of ordinary skill in the art will also appreciate that different species can exhibit "preferential codon usage." Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequences disclosed in SEQ ID NOs:3, 28, 30, and 39 serve as templates for optimizing expression of polynucleotides in various cell types and species commonly used in the art and disclosed herein. Sequences containing preferential codons can be tested and optimized for expression in various species, and tested for functionality as disclosed herein.

Within preferred embodiments of the invention the isolated polynucleotides will hybridize to similar sized regions of SEQ ID NOs:1, 3, 22, 28, 30, 31, 32, 33, 36, and 39, or a sequence complementary thereto under stringent conditions. Polynucleotide hybridization is well known in the art and widely used for many applications, see for example, Sambrook et al., *Molecular Cloning: A Laboratory Manual, Second Edition*, Cold Spring Harbor, N.Y., 1989; Ausubel et al., eds., *Current Protocols in Molecular Biology*, John Wiley and Sons, Inc., NY, 1987; Berger and Kimmel, eds., Guide to Molecular Cloning Techniques, *Methods in Enzymology*, volume 152, 1987 and Wetmur, *Crit. Rev. Biochem. Mol. Biol.* 26:227–59, 1990. Polynucleotide hybridization exploits the ability of single stranded complementary sequences to form a double helix hybrid. Such hybrids include DNA-DNA, RNA-RNA and DNA-RNA.

As an illustration, a nucleic acid molecule encoding a variant UMLR polypeptide can be hybridized with a nucleic acid molecule having the nucleotide sequence of SEQ ID NOs:1, 3, 22, 28, 30, 31, 32, 33, 36, and 39 (or their complements) at 65° C. overnight in ExpressHyb™ Hybridization Solution (CLONTECH Laboratories, Inc., Palo Alto, Calif.). One of skill in the art can devise variations of these hybridization conditions.

Following hybridization, the nucleic acid molecules can be washed to remove non-hybridized nucleic acid molecules under stringent conditions, or under highly stringent conditions. Typical stringent washing conditions include washing in a solution of 0.5×–2×SSC with 0.1% sodium dodecyl sulfate (SDS) at 55–65° C. That is, nucleic acid molecules encoding a variant UMLR polypeptide hybridize with a nucleic acid molecule having the nucleotide sequences of SEQ ID NOs:1, 3, 22, 28, 30, 31, 32, 33, 35, 36, and 39 (or their complements) under stringent washing conditions, in which the wash stringency is equivalent to 0.1×–2×SSC with 0.1% SDS at 55–65° C., including 0.1×SSC with 0.1% SDS at 55° C., or 2×SSC with 0.1% SDS at 65° C. One of skill in the art can readily devise equivalent conditions, for example, by substituting SSPE for SSC in the wash solution.

The present invention also contemplates UMLR variant nucleic acid molecules that can be identified using two criteria: a determination of the similarity between the encoded polypeptides with the amino acid sequences of SEQ ID NOs:2, 27, 29, 34, 35, 37, and 38 (as described below), and a hybridization assay, as described above. Such UMLR variants include nucleic acid molecules that hybridize with a nucleic acid molecule having the nucleotide sequence of SEQ ID NOs:1, 3, 22, 28, 30, 31, 32, 33, 36, and 39 (or their complements) under stringent washing conditions, in which the wash stringency is equivalent to 0.1×–2×SSC with 0.1% SDS at 55–65° C., and (2) that encode a polypeptide having at least 80%, preferably 90%, more preferably, 95% or greater than 95% sequence identity to the amino acid sequence of SEQ ID NOs:2, 27, 29, 34, 35, 37, and 38. Alternatively, UMLR variants can be characterized as nucleic acid molecules (1) that hybridize with a nucleic acid molecule having the nucleotide sequence of SEQ ID NOs:1, 3, 22, 28, 30, 31, 32, 33, 35, 36, and 39 (or their complements) under highly stringent washing conditions, in which the wash stringency is equivalent to 0.1×–0.2×SSC with 0.1% SDS at 50–65° C., and (2) that encode a polypeptide having at least 80%, preferably 90%, more preferably 95% or greater than 95% sequence identity to the amino acid sequence of SEQ ID NOs:2, 27, 29, 34, 35, 37, and 38.

The highly conserved amino acids in the cysteine-rich pseudo-repeat domains of UMLR can be used as a tool to identify new family members. For instance, reverse transcription-polymerase chain reaction (RT-PCR) can be used to amplify sequences encoding the conserved cysteine-rich domain from RNA obtained from a variety of tissue sources or cell lines. In particular, highly degenerate primers designed from the UMLR sequences are useful for this purpose.

As previously noted, the isolated polynucleotides of the present invention include DNA and RNA. Methods for preparing DNA and RNA are well known in the art. In general, RNA is isolated from a tissue or cell that produces large amounts of UMLR RNA. Such tissues and cells are identified by Northern blotting (Thomas, *Proc. Natl. Acad. Sci. USA* 77:5201, 1980) and in situ hybridization, and include tissues of the uterus, lung carcinoma and breast carcinoma, as well as cell lines of melanoma, osteosarcoma and lymphoma. Cells lines which express ztnfr11 polynucleotides and polypeptides are available from ATCC (Manasas, Va.) and include, but are not limited to ATCC numbers HTB-64, CRL-1585, HTB-68, and CRL-1424.

Total RNA can be prepared using guanidine isothiocyante extraction followed by isolation by centrifugation in a CsCl gradient (Chirgwin et al., *Biochemistry* 18:52–94, 1979). Poly (A)$^+$ RNA is prepared from total RNA using the method of Aviv and Leder (*Proc. Natl. Acad. Sci. USA* 69:1408–12, 1972). Complementary DNA (cDNA) is prepared from poly(A)$^+$ RNA using known methods. In the alternative, genomic DNA can be isolated. Polynucleotides encoding UMLR polypeptides are then identified and isolated by, for example, hybridization or PCR.

A full-length clone encoding UMLR can be obtained by conventional cloning procedures. Complementary DNA (cDNA) clones are preferred, although for some applications (e.g., expression in transgenic animals) it may be preferable to use a genomic clone, or to modify a cDNA clone to include at least one genomic intron. Methods for preparing cDNA and genomic clones are well known and within the level of ordinary skill in the art, and include the use of the sequence disclosed herein, or parts thereof, for probing or priming a library. Expression libraries can be probed with antibodies to UMLR or other specific binding partners.

The invention also provides isolated and purified UMLR polynucleotide probes. Such polynucleotide probes can be RNA or DNA. DNA can be either cDNA or genomic DNA. Polynucleotide probes are single or double-stranded DNA or RNA, generally synthetic oligonucleotides, but may be generated from cloned cDNA or genomic sequences and will generally comprise at least 16 nucleotides, more often from 17 nucleotides to 25 or more nucleotides, sometimes 40 to 60 nucleotides, and in some instances a substantial portion, domain or even the entire UMLR gene or cDNA. The synthetic oligonucleotides of the present invention have at least 80% identity to a representative UMLR DNA sequence (SEQ ID NOs:1, 3, 22, 28, 30, 31, 32, 33, 36, and 39) or their complements. The invention also provides oligonucleotide probes or primers comprising at least 14 contiguous nucleotides of a polynucleotide of SEQ ID NOs:1, 3, 22, 28, 30, 31, 32, 33, 36, and 39 or a sequence complementary to SEQ ID NOs:1, 3, 22, 28, 30, 31, 32, 33, 35, 36, and 39.

Preferred regions from which to construct probes include the 5' and/or 3' coding sequences, ligand binding regions, and signal sequences, and the like. Techniques for developing polynucleotide probes and hybridization techniques are known in the art, see for example, Ausubel et al., eds., *Current Protocols in Molecular Biology*, John Wiley and Sons, Inc., NY, 1991. For use as probes, the molecules can be labeled to provide a detectable signal, such as with an enzyme, biotin, a radionuclide, fluorophore, chemiluminescer, paramagnetic particle and the like, which are commercially available from many sources, such as Molecular Probes, Inc., Eugene, Oreg., and Amersham Corp., Arlington Heights, Ill., using techniques that are well known in the art. Such probes can also be used in hybridizations to detect the presence or quantify the amount of UMLR gene or mRNA transcript in a sample. UMLR polynucleotide probes could be used to hybridize to DNA or RNA targets for diagnostic purposes, using such techniques such as fluorescent in situ hybridization (FISH) or immunohistochemistry. Polynucleotide probes can be used to identify genes encoding UMLR-like proteins. For example, UMLR polynucleotides can be used as primers and/or templates in PCR reactions to identify other novel members of the TNFR family. Such probes can also be used to screen libraries for related sequences encoding novel tumor necrosis factor receptors. Such screening would be carried out under conditions of low stringency which would allow identification of sequences which are substantially homologous, but not requiring complete homology to the probe sequence. Such methods and conditions are well known in the art, see, for example, Sambrook et al., *Molecular Cloning: A Laboratory Manual*, Second Edition, Cold Spring Harbor, N.Y., 1989. Such low stringency conditions could include hybridization temperatures less than 42° C., formamide concentrations of less than 50% and moderate to low concentrations of salt. Libraries may be made of genomic DNA or cDNA. Polynucleotide probes are also useful for Southern, Northern, or slot blots, colony and plaque hybridization and in situ hybridization. Mixtures of different UMLR polynucleotide probes can be prepared which would increase sensitivity or the detection of low copy number targets, in screening systems.

In addition, such polynucleotide probes could be used to hybridize to counterpart sequences on individual chromosomes. Chromosomal identification and/or mapping of the UMLR gene could provide useful information about gene function and disease association. Many mapping techniques are available to one skilled in the art, for example, mapping somatic cell hybrids, and fluorescence in situ hybridization (FISH). A preferred method is radiation hybrid mapping. Radiation hybrid mapping is a somatic cell genetic technique developed for constructing high-resolution, contiguous maps of mammalian chromosomes (Cox et al., *Science* 250:245–50, 1990). Partial or full knowledge of a gene's sequence allows the designing of PCR primers suitable for use with chromosomal radiation hybrid mapping panels. Commercially available radiation hybrid mapping panels which cover the entire human genome, such as the Stanford G3 RH Panel and the GeneBridge 4 RH Panel (Research Genetics, Inc., Huntsville, Ala.), are available. These panels enable rapid, PCR based, chromosomal localizations and ordering of genes, sequence-tagged sites (STSs), and other non-polymorphic- and polymorphic markers within a region of interest. This includes establishing directly proportional physical distances between newly discovered genes of interest and previously mapped markers. The precise knowledge of a gene's position can be useful in a number of ways including: 1) determining if a sequence is part of an existing contig and obtaining additional surrounding genetic sequences in various forms such as YAC-, BAC- or cDNA clones, 2) providing a possible candidate gene for an inheritable disease which shows linkage to the same chromosomal region, and 3) for cross-referencing model organisms such as mouse which may be beneficial in helping to determine what function a particular gene might have.

UMLR polynucleotide sequences disclosed herein can also be used as probes or primers to clone 5' non-coding regions of a UMLR gene. In view of the tissue-specific expression observed for UMLR by Northern blotting, this gene region is expected to provide for specific expression in tissues of the uterus, lung carcinoma and breast carcinoma, as well as in cell lines of melanoma, osteosarcoma and lymphoma. Promoter elements from a UMLR gene could thus be used to direct the tissue-specific expression of heterologous genes in, for example, transgenic animals or patients treated with gene therapy. Cloning of 5' flanking sequences also facilitates production of UMLR proteins by "gene activation" as disclosed in U.S. Pat. No. 5,641,670. Briefly, expression of an endogenous UMLR gene in a cell is altered by introducing into the UMLR locus a DNA construct comprising at least a targeting sequence, a regulatory sequence, an exon, and an unpaired splice donor site. The targeting sequence is a UMLR 5' non-coding sequence that permits homologous recombination of the construct with the endogenous UMLR locus, whereby the sequences within the construct become operably linked with the endogenous UMLR coding sequence. In this way, an endogenous UMLR promoter can be replaced or supplemented with other regulatory sequences to provide enhanced, tissue-specific, or otherwise regulated expression.

The polynucleotides of the present invention can also be synthesized using DNA synthesizers. Currently the method of choice is the phosphoramidite method. If chemically synthesized double stranded DNA is required for an application such as the synthesis of a gene or a gene fragment, then each complementary strand is made separately. The production of short genes (60 to 80 bp) is technically straightforward and can be accomplished by synthesizing the complementary strands and then annealing them. For the production of longer genes (>300 bp), however, special strategies must be invoked, because the coupling efficiency of each cycle during chemical DNA synthesis is seldom 100%. To overcome this problem, synthetic genes (double-stranded) are assembled in modular form from single-stranded fragments that are from 20 to 100 nucleotides in length. See Glick and Pasternak, *Molecular Biotechnology, Principles and Applications of Recombinant DNA*, (ASM Press, Washington, D.C. 1994); Itakura et al., *Annu. Rev. Biochem.* 53: 323–356 (1984) and Climie et al., *Proc. Natl. Acad. Sci. USA* 87:633–7, 1990.

The present invention further provides counterpart polypeptides and polynucleotides from other species (orthologs). These species include, but are not limited to mammalian, avian, amphibian, reptile, fish, insect and other vertebrate and invertebrate species. Of particular interest are UMLR polypeptides from other mammalian species, including murine, porcine, ovine, bovine, canine, feline, equine, and other primate polypeptides. Orthologs of human UMLR can be cloned using information and compositions provided by the present invention in combination with conventional cloning techniques. For example, a cDNA can be cloned using mRNA obtained from a tissue or cell type that expresses UMLR as disclosed herein. Such tissue would include, for example, tissues of the uterus, lung carcinoma, breast carcinoma, as well as in cell lines of melanoma, osteosarcoma, and lymphoma. Suitable sources of mRNA can be identified by probing Northern blots with probes designed from the sequences disclosed herein. A library is then prepared from mRNA of a positive tissue or cell line. A UMLR-encoding cDNA can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the representative human UMLR sequences disclosed herein. Within an additional method, the cDNA library can be used to transform or transfect host cells, and expression of the cDNA of interest can be detected with an antibody to UMLR polypeptide. Similar techniques can also be applied to the isolation of genomic clones.

Those skilled in the art will recognize that the sequences disclosed in SEQ ID NO:1 represents a single allele of human UMLR and that allelic variation and alternative splicing are expected to occur. Allelic variants of this sequence can be cloned by probing cDNA or genomic libraries from different individuals according to standard procedures. Allelic variants of the DNA sequences shown in SEQ ID NO:1, including those containing silent mutations and those in which mutations result in amino acid sequence changes, are within the scope of the present invention, as are proteins which are allelic variants of SEQ ID NO:2. cDNAs generated from alternatively spliced mRNAs, which retain the properties of the UMLR polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

The present invention also provides isolated UMLR polypeptides that are substantially similar to the polypeptides of SEQ ID NOs:2, 27, 29, 34, 35, 37, and 38 and their orthologs. Such polypeptides will more preferably be at least 90% identical, and more preferably 95% or more identical to SEQ ID NOs:2, 27, 29, 34, 35, 37, and 38 and their orthologs. Percent sequence identity is determined by conventional methods. See, for example, Altschul et al., *Bull. Math. Bio.* 48: 603–16, 1986 and Henikoff and Henikoff, *Proc. Natl. Acad. Sci. USA* 89:10915–9, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 3 (amino acids are indicated by the standard one-letter codes). The percent identity is then calculated as:

$$\frac{\text{Total number of identical matches}}{\text{[length of the longer sequence plus the number of gaps introduced into the longer sequence in order to align the two sequences]}} \times 100$$

TABLE 3

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | −1 | 5 | | | | | | | | | | | | | | | | | | |
| N | −2 | 0 | 6 | | | | | | | | | | | | | | | | | |
| D | −2 | −2 | 1 | 6 | | | | | | | | | | | | | | | | |
| C | 0 | −3 | −3 | −3 | 9 | | | | | | | | | | | | | | | |
| Q | −1 | 1 | 0 | 0 | −3 | 5 | | | | | | | | | | | | | | |
| E | −1 | 0 | 0 | 2 | −4 | 2 | 5 | | | | | | | | | | | | | |
| G | 0 | −2 | 0 | −1 | −3 | −2 | −2 | 6 | | | | | | | | | | | | |
| H | −2 | 0 | 1 | −1 | −3 | 0 | 0 | −2 | 8 | | | | | | | | | | | |
| I | −1 | −3 | −3 | −3 | −1 | −3 | −3 | −4 | −3 | 4 | | | | | | | | | | |
| L | −1 | −2 | −3 | −4 | −1 | −2 | −3 | −4 | −3 | 2 | 4 | | | | | | | | | |

TABLE 3-continued

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| K | −1 | 2 | 0 | −1 | −3 | 1 | 1 | −2 | −1 | −3 | −2 | 5 | | | | | | | | |
| M | −1 | −1 | −2 | −3 | −1 | 0 | −2 | −3 | −2 | 1 | 2 | −1 | 5 | | | | | | | |
| F | −2 | −3 | −3 | −3 | −2 | −3 | −3 | −3 | −1 | 0 | 0 | −3 | 0 | 6 | | | | | | |
| P | −1 | −2 | −2 | −1 | −3 | −1 | −1 | −2 | −2 | −3 | −3 | −1 | −2 | −4 | 7 | | | | | |
| S | 1 | −1 | 1 | 0 | −1 | 0 | 0 | 0 | −1 | −2 | −2 | 0 | −1 | −2 | −1 | 4 | | | | |
| T | 0 | −1 | 0 | −1 | −1 | −1 | −1 | −2 | −2 | −1 | −1 | −1 | −1 | −2 | −1 | 1 | 5 | | | |
| W | −3 | −3 | −4 | −4 | −2 | −2 | −3 | −2 | −2 | −3 | −2 | −3 | −1 | 1 | −4 | −3 | −2 | 11 | | |
| Y | −2 | −2 | −2 | −3 | −2 | −1 | −2 | −3 | 2 | −1 | −1 | −2 | −1 | 3 | −3 | −2 | −2 | 2 | 7 | |
| V | 0 | −3 | −3 | −3 | −1 | −2 | −2 | −3 | −3 | 3 | 1 | −2 | 1 | −1 | −2 | −2 | 0 | −3 | −1 | 4 |

Sequence identity of polynucleotide molecules is determined by similar methods using a ratio as disclosed above.

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative variant UMLR. The FASTA algorithm is described by Pearson and Lipman, *Proc. Nat'l Acad. Sci. USA* 85:2444 (1988), and by Pearson, *Meth. Enzymol.* 183:63 (1990).

Briefly, FASTA first characterizes sequence similarity by identifying regions shared by the query sequence (e.g., SEQ ID NOs:2, 27, 29, 34, 35, 37, and 38) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444 (1970); Sellers, *SIAM J. Appl. Math.* 26:787 (1974)), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.* 183:63 (1990).

FASTA can also be used to determine the sequence identity of nucleic acid molecules using a ratio as disclosed above. For nucleotide sequence comparisons, the ktup value can range between one to six, preferably from four to six.

The present invention includes nucleic acid molecules that encode a polypeptide having one or more conservative amino acid changes, compared with the amino acid sequences of SEQ ID NOs:2, 27, 29, 34, 35, 37, and 38. The BLOSUM62 table is an amino acid substitution matrix derived from about 2,000 local multiple alignments of protein sequence segments, representing highly conserved regions of more than 500 groups of related proteins (Henikoff and Henikoff, *Proc. Nat'l Acad. Sci. USA* 89:10915 (1992)). Accordingly, the BLOSUM62 substitution frequencies can be used to define conservative amino acid substitutions that may be introduced into the amino acid sequences of the present invention. As used herein, the language "conservative amino acid substitution" refers to a substitution represented by a BLOSUM62 value of greater than −1. For example, an amino acid substitution is conservative if the substitution is characterized by a BLOSUM62 value of 0, 1, 2, or 3. Preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Conservative amino acid changes in an UMLR gene can be introduced by substituting nucleotides for the nucleotides recited in SEQ ID NOs:1, 3, 22, 28, 30, 31, 32, 33, 35, 36, and 39. Such "conservative amino acid" variants can be obtained, for example, by oligonucleotide-directed mutagenesis, linker-scanning mutagenesis, mutagenesis using the polymerase chain reaction, and the like (see Ausubel (1995) at pages 8-10 to 8-22; and McPherson (ed.), *Directed Mutagenesis: A Practical Approach* (IRL Press 1991)). The ability of such variants to modulate cell-cell interactions, apoptosis, and inflammation can be determined using a standard method, such as the assay described herein. Alternatively, a variant UMLR polypeptide can be identified by the ability to specifically bind anti-UMLR antibodies.

Essential amino acids in the polypeptides of the present invention can be identified according to procedures known in the art, such as site-directed mutagenesis or alanine-scanning mutagenesis (Cunningham and Wells, *Science* 244: 1081–5, 1989; Bass et al., *Proc. Natl. Acad. Sci. USA* 88:4498–502, 1991). In the latter technique, single alanine mutations are introduced at every residue in the molecule, and the resultant mutant molecules are tested for biological activity as disclosed below to identify amino acid residues that are critical to the activity of the molecule. See also, Hilton et al., *J. Biol. Chem.* 271:4699–708, 1996. Sites of receptor-ligand interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306–12, 1992; Smith et al., *J. Mol. Biol.* 224:899–904, 1992; Wlodaver et al., *FEBS Lett.* 309:59–64, 1992. The identities of essential amino acids can also be inferred from analysis of homologies with related TNFR-like molecules.

Multiple amino acid substitutions can be made and tested using known methods of mutagenesis and screening, such as those disclosed by Reidhaar-Olson and Sauer (*Science* 241: 53–7, 1988) or Bowie and Sauer (*Proc. Natl. Acad. Sci. USA* 86:2152–6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832–7, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Variants of the disclosed UMLR DNA and polypeptide sequences can be generated through DNA shuffling, as disclosed by Stemmer, *Nature* 370:389–91, 1994, Stemmer, *Proc. Natl. Acad. Sci. USA* 91:10747–51, 1994 and WIPO Publication WO 97/20078. Briefly, variant DNAs are generated by in vitro homologous recombination by random fragmentation of a parent DNA followed by reassembly using PCR, resulting in randomly introduced point mutations. This technique can be modified by using a family of parent DNAs, such as allelic variants or DNAs from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode active polypeptides (e.g., ligand binding activity) can be recovered from the host cells and rapidly sequenced using modern equipment. These methods allow the rapid determination of the importance of individual amino acid residues in a polypeptide of interest, and can be applied to polypeptides of unknown structure.

Regardless of the particular nucleotide sequence of a variant UMLR gene, the gene encodes a polypeptide that is characterized by its cell-cell interaction activity, including but not limited to apoptosis, and tumorigensis, or by the ability to bind specifically to an anti-UMLR antibody. More specifically, variant UMLR genes encode polypeptides which exhibit at least 50%, and preferably, greater than 70, 80, or 90%, of the activity of polypeptide encoded by the human UMLR gene described herein.

Variant UMLR polypeptides or substantially homologous UMLR polypeptides are characterized as having one or more amino acid substitutions, deletions or additions. These changes are preferably of a minor nature, that is conservative amino acid substitutions and other substitutions that do not significantly affect the folding or activity of the polypeptide; small deletions, typically of one to about 30 amino acids; and amino- or carboxyl-terminal extensions, such as an amino-terminal methionine residue, a small linker peptide of up to about 20–25 residues, or an affinity tag. The present invention thus includes polypeptides of from 40 to 2000 amino acid residues that comprise a sequence that is at least 85%, preferably at least 90%, and more preferably 95% or more identical to the corresponding region of SEQ ID NOs:2, 27, 29, 34, 35, 37, and 38. Polypeptides comprising affinity tags can further comprise a proteolytic cleavage site between the UMLR polypeptide and the affinity tag. Preferred such sites include thrombin cleavage sites and factor Xa cleavage sites.

For any UMLR polypeptide, including variants and fusion proteins, one of ordinary skill in the art can readily generate a fully degenerate polynucleotide sequence encoding that variant using the information set forth in Tables 1 and 2 above. Moreover, those of skill in the art can use standard software to devise UMLR variants based upon the nucleotide and amino acid sequences described herein. Accordingly, the present invention includes a computer-readable medium encoded with a data structure that provides at least one of the following sequences: SEQ ID NOs:1, 2, 3, 22, 27, 28, 29, 30, 31, 32, 33, 34, 35, 36, 37, 38, and 39. Suitable forms of computer-readable media include magnetic media and optically-readable media. Examples of magnetic media include a hard or fixed drive, a random access memory (RAM) chip, a floppy disk, digital linear tape (DLT), a disk cache, and a ZIP disk. Optically readable media are exemplified by compact discs (e.g., CD-read only memory (ROM), CD-rewritable (RW), and CD-recordable), and digital versatile/video discs (DVD) (e.g., DVD-ROM, DVD-RAM, and DVD+RW).

The present invention further provides a variety of other polypeptide fusions and related multimeric proteins comprising one or more polypeptide fusions. For example, the cysteine-rich pseudo-repeat, or cytoplasmic polypeptide domains can be prepared as a fusion to a dimerizing protein, as disclosed in U.S. Pat. Nos. 5,155,027 and 5,567,584. Preferred dimerizing proteins in this regard include other cysteine-rich pseudo-repeat or cytoplasmic polypeptide domains, or polypeptides comprising other members of the TNF receptor family of proteins, such as, for example, APO4, TNFR-I, TNFR-II, and TNFR-III. Additionally, chimeras can be prepared with the extracellular portion of cytokine receptors. For example, the extracellular domain of erythropoietin can be fused to the linker, transmembrane, and cytoplasmic domain of UMRL polypeptides to produce dimerization. These polypeptide domain fusions, can be expressed in genetically engineered cells to produce a variety of multimeric TNFR-like analogs.

Fusion proteins can be prepared by methods known to those skilled in the art by preparing each component of the fusion protein and chemically conjugating them. Alternatively, a polynucleotide encoding both components of the fusion protein in the proper reading frame can be generated using known techniques and expressed by the methods described herein. For example, part or all of a domain(s) conferring a biological function may be swapped between UMLR of the present invention with the functionally equivalent domain(s) from another family member, such as APO4, TNFR-I, TNFR-II, and TNFR-III. Such domains include, but are not limited to, conserved motifs such as the cysteine-rich pseudo-repeat, transmembrane, and cytoplasmic domains. Such fusion proteins would be expected to have a biological functional profile that is the same or similar to polypeptides of the present invention or other known TNFR family proteins (e.g. APO4, TNFR-I, TNFR-II, and TNFR-III), depending on the fusion constructed. Moreover, such fusion proteins may exhibit other properties as disclosed herein.

Moreover, using methods described in the art, polypeptide fusions, or hybrid UMLR proteins, are constructed using regions or domains of the inventive UMLR in combination with those of other TNFR molecules. (e.g. APO4, TNFR-I, TNFR-II, and TNFR-III), or heterologous proteins (Sambrook et al., ibid., Altschul et al., ibid., Picard, *Cur. Opin. Biology,* 5:511–5, 1994, and references therein). These methods allow the determination of the biological importance of larger domains or regions in a polypeptide of interest. Such hybrids may alter reaction kinetics, binding, constrict or expand the substrate specificity, or alter tissue and cellular localization of a polypeptide, and can be applied to polypeptides of unknown structure.

Auxiliary domains can be fused to UMLR polypeptides to target them to specific cells, tissues, or macromolecules (e.g., tissues of the uterus, lung carcinoma and breast carcinoma, as well as in cells of melanoma, osteosarcoma, and lymphoma). For example, a protease domain could be targeted to a predetermined cell type (uterus, melanoma, osteosarcoma, breast carcinoma, and lymphoma, and in tumorous lung) by fusing it to a the cysteine-rich pseudo-repeat domains (i.e., residues 1 to 129 of SEQ ID NO:2, or residues 1 to 173 of SEQ ID NO:38), or a portion thereof which has been shown to bind the cognate ligand for UMLR. In this way, polypeptides, polypeptide fragments and proteins can be targeted for therapeutic or diagnostic purposes. Such the cysteine-rich pseudo-repeat domains, or portions thereof can be fused to two or more moieties, such as an affinity tag for purification and a targeting domains. Polypeptide fusions can also comprise one or more cleavage sites, particularly between domains. See, Tuan et al., *Connective Tissue Research* 34:1–9, 1996.

Polypeptide fusions of the present invention will generally contain not more than about 1,500 amino acid residues, preferably not more than about 1,200 residues, more preferably not more than about 1,000 residues, and will in many cases be considerably smaller. For example, residues of UMLR polypeptide can be fused to *E. coli* b-galactosidase (1,021 residues; see Casadaban et al., J. Bacteriol. 143: 971–980, 1980), a 10-residue spacer, and a 4-residue factor Xa cleavage site. In a second example, residues of UMLR polypeptide can be fused to maltose binding protein (approximately 370 residues), a 4-residue cleavage site, and a 6-residue polyhistidine tag.

UMLR polypeptides or fragments thereof may also be prepared through chemical synthesis. UMLR polypeptides may be monomers or multimers; glycosylated or non-glycosylated; pegylated or non-pegylated; and may or may not include an initial methionine amino acid residue.

The invention also provides soluble UMLR receptors, used to form fusion or chimeric proteins with human Ig, as His-tagged proteins, or FLAG™-tagged proteins. One such construct is comprises residues 1 to 129 of SEQ ID NO:2, fused to human Ig. UMLR or UMLR-Ig chimeric proteins are used, for example, to identify the UMLR ligands, including the natural ligand, as well as agonists and antagonists of the natural ligand. Another construct comprises residues 1 to 173 of SEQ ID NO: 38 fused to the human Ig. Additional constructs comprise residues 1 to 130 of SEQ ID NO:2, residues 1 to 131 of SEQ ID NO:2, residues 1 to 132 of SEQ ID NO:2, residues 1 to 133 of SEQ ID NO:2, residues 1 to 134 of SEQ ID NO:2, residues 1 to 135 of SEQ ID NO:2, residues 1 to 136 of SEQ ID NO:2 fused to the human Ig. Additional constructs consist of residues 2 to 130 of SEQ ID NO:2, residues 2 to 131 of SEQ ID NO:2, residues 2 to 132 of SEQ ID NO:2, residues 2 to 133 of SEQ ID NO:2, residues 2 to 134 of SEQ ID NO:2, residues 2 to 135 of SEQ ID NO:2, residues 2 to 136 of SEQ ID NO:2, residues 1 to 173 of SEQ ID NO:38, residues 1 to 147 of SEQ ID NO:38, residues 1 to 154 of SEQ ID NO:38, and residues 1 to 165 of SEQ ID NO:38, fused to the human Ig. Using labeled soluble UMLR, cells expressing the ligand are identified by fluorescence immunocytometry or immunohistochemistry. The soluble fusion proteins or soluble Ig fusion protein is useful in studying the distribution of the ligand on tissues or specific cell lineages, and to provide insight into receptor/ligand biology.

In an alternative approach, a soluble UMLR receptor extracellular ligand-binding region can be expressed as a chimera with immunoglobulin heavy chain constant regions, typically an $F_c$ fragment, which contains two constant region domains and a hinge region, but lacks the variable region. Such fusions are typically secreted as multimeric molecules, wherein the Fc portions are disulfide bonded to each other and two receptor polypeptides are arrayed in close proximity to each other. Fusions of this type can be used to affinity purify the cognate ligand from solution, as an in vitro assay tool, to block signals in vitro by specifically titrating out ligand, and as antagonists in vivo by administering them to block ligand stimulation. To purify ligand, a UMLR-Ig fusion protein (chimera) is added to a sample containing the ligand under conditions that facilitate receptor-ligand binding (typically near-physiological temperature, pH, and ionic strength). The chimera-ligand complex is then separated by the mixture using protein A, which is immobilized on a solid support (e.g., insoluble resin beads). The ligand is then eluted using conventional chemical techniques, such as with a salt or pH gradient. In the alternative, the chimera itself can be bound to a solid support, with binding and elution carried out as above. For use in assays, the chimeras are bound to a support via the $F_C$ region and used in an ELISA format.

Ligand binding studies have been performed on a number of known tumor necrosis factors including TNFα, TNFβ, THANK (Mukhopadhyay et al., *J. Biol. Chem.* 274:15978–81, 1999), FasL, RankL, Trail, and Tweak. None of these ligands has been shown to bind to ztnfr11.

To direct the export of a UMLR polypeptide from the host cell, the UMLR DNA may be linked to a second DNA segment encoding a secretory peptide, such as a t-PA secretory peptide or a UMLR secretory peptide. To facilitate purification of the secreted polypeptide, a C-terminal extension, such as a poly-histidine tag, substance P, Flag peptide (Hopp et al., *Bio/Technology* 6:1204–1210, 1988; available from Eastman Kodak Co., New Haven, Conn.), maltose binding protein, or another polypeptide or protein for which an antibody or other specific binding agent is available, can be fused to the UMLR polypeptide.

The present invention also includes "functional fragments" of UMLR polypeptides and nucleic acid molecules encoding such functional fragments. Routine deletion analyses of nucleic acid molecules can be performed to obtain functional fragments of a nucleic acid molecule that encodes an UMLR polypeptide. As an illustration, DNA molecules having the nucleotide sequence of SEQ ID NOs:1, 22, 32, 33, and 36, can be digested with Bal31 nuclease to obtain a series of nested deletions. The fragments are then inserted into expression vectors in proper reading frame, and the expressed polypeptides are isolated and tested for cell-cell interactions, or for the ability to bind anti-UMLR antibodies. One alternative to exonuclease digestion is to use oligonucleotide-directed mutagenesis to introduce deletions or stop codons to specify production of a desired fragment. Alternatively, particular fragments of an UMLR gene can be synthesized using the polymerase chain reaction.

Standard methods for identifying functional domains are well-known to those of skill in the art. For example, studies on the truncation at either or both termini of interferons have been summarized by Horisberger and Di Marco, *Pharmac. Ther.* 66:507 (1995). Moreover, standard techniques for functional analysis of proteins are described by, for example, Treuter et al., *Molec. Gen. Genet.* 240:113 (1993), Content et al., "Expression and preliminary deletion analysis of the 42 kDa 2–5A synthetase induced by human interferon," in *Biological Interferon Systems, Proceedings of ISIR-TNO Meeting on Interferon Systems*, Cantell (ed.), pages 65–72 (Nijhoff 1987), Herschman, "The EGF Receptor," in *Control of Animal Cell Proliferation, Vol.* 1, Boynton et al., (eds.)

pages 169–199 (Academic Press 1985), Coumailleau et al., *J. Biol. Chem.* 270:29270 (1995); Fukunaga et al., *J. Biol. Chem.* 270:25291 (1995); Yamaguchi et al., *Biochem. Pharmacol.* 50:1295 (1995), and Meisel et al., *Plant Molec. Biol.* 30:1 (1996).

The present invention also contemplates functional fragments of an UMLR gene that has amino acid changes, compared with the amino acid sequences of SEQ ID NOs:2, 27, 29, 35, and 38. A variant UMLR gene can be identified on the basis of structure by determining the level of identity with nucleotide and amino acid sequences of SEQ ID NOs:1, 2, 3, 22, 27, 28, 29, 30, 31, 32, 33, 34, 35, 36, 37, 38, and 39 as discussed above. An alternative approach to identifying a variant gene on the basis of structure is to determine whether a nucleic acid molecule encoding a potential variant UMLR gene can hybridize to a nucleic acid molecule having the nucleotide sequence of SEQ ID NO:1, as discussed above.

Using the methods discussed herein, one of ordinary skill in the art can identify and/or prepare a variety of polypeptide fragments or variants of SEQ ID NO:2 or that retain the ligand-binding, or intracellular signaling activity of the wild-type UMLR protein. Such polypeptides may include additional amino acids from, for example, cysteine-rich pseudo-repeats, a linker domain, a transmembrane and cytoplasmic domains, including amino acids responsible for intracellular signaling; fusion domains; affinity tags; and the like. Similarly, the cysteine-rich pseudo repeats (i.e., residues 2 to 42 of SEQ ID NO:2, residues 43 to 84 of SEQ ID NO:2, and/or residues 85 to 129 of SEQ ID NO:2) can be substituted for the cysteine-rich pseudo repeats from other TNFR family member to increase or decrease ligand binding, or specificity.

Within the polypeptides of the present invention are polypeptides that comprise an epitope-bearing portion of a protein as shown in SEQ ID NO:2. An "epitope" is a region of a protein to which an antibody can bind. See, for example, Geysen et al., *Proc. Natl. Acad. Sci. USA* 81:3998–4002, 1984. Epitopes can be linear or conformational, the latter being composed of discontinuous regions of the protein that form an epitope upon folding of the protein. Linear epitopes are generally at least 6 amino acid residues in length. Relatively short synthetic peptides that mimic part of a protein sequence are routinely capable of eliciting an antiserum that reacts with the partially mimicked protein. See, Sutcliffe et al., *Science* 219:660–666, 1983. Antibodies that recognize short, linear epitopes are particularly useful in analytic and diagnostic applications that employ denatured protein, such as Western blotting (Tobin, *Proc. Natl. Acad. Sci. USA* 76:4350–4356, 1979), or in the analysis of fixed cells or tissue samples. Antibodies to linear epitopes are also useful for detecting fragments of UMLR, such as might occur in body fluids or cell culture media.

Antigenic, epitope-bearing polypeptides of the present invention are useful for raising antibodies, including monoclonal antibodies, that specifically bind to a UMLR protein. Antigenic, epitope-bearing polypeptides contain a sequence of at least six, preferably at least nine, more preferably from 15 to about 30 contiguous amino acid residues of a UMLR protein (e.g., SEQ ID NO:2). Polypeptides comprising a larger portion of a UMLR protein, i.e. from 30 to 50 residues up to the entire sequence, are included. It is preferred that the amino acid sequence of the epitope-bearing polypeptide is selected to provide substantial solubility in aqueous solvents, that is the sequence includes relatively hydrophilic residues, and hydrophobic residues are substantially avoided. Preferred such regions include the cysteine-rich pseudo-repeats, the linker domain, the transmembrane domain, or the cytoplasmic domain UMLR and fragments thereof. Specific, preferred polypeptides in this regard include those comprising residues 2 to 42 of SEQ ID NO:2; residues 43 to 84 of SEQ ID NO:2; residues 85 to 129 of SEQ ID NO:2; residues 130 to 136 of SEQ ID NO:2; residues 137 to 161 of SEQ ID NO:2; residues 162 to 269 of SEQ ID NO:2; residues 1 to 269 of SEQ ID NO:2; residues 1 to 129 of SEQ ID NO:2; residues 1 to 136 of SEQ ID NO:2; residues 137 to 269 of SEQ ID NO:2; residues 85 to 173 of SEQ ID NO:38; residues 85 to 163 of SEQ ID NO:38; residues 85 to 165 of SEQ ID NO:38; residues 85 to 147 of SEQ ID NO:38; and residues 85 to 154 of SEQ ID NO:38.

The present invention also provides polypeptide fragments or peptides comprising an epitope-bearing portion of an UMLR polypeptide described herein. Such fragments or peptides may comprise an "immunogenic epitope," which is a part of a protein that elicits an antibody response when the entire protein is used as an immunogen. Immunogenic epitope-bearing peptides can be identified using standard methods (see, for example, Geysen et al., *Proc. Nat'l Acad. Sci. USA* 81:3998 (1983)).

In contrast, polypeptide fragments or peptides may comprise an "antigenic epitope," which is a region of a protein molecule to which an antibody can specifically bind. Certain epitopes consist of a linear or contiguous stretch of amino acids, and the antigenicity of such an epitope is not disrupted by denaturing agents. It is known in the art that relatively short synthetic peptides that can mimic epitopes of a protein can be used to stimulate the production of antibodies against the protein (see, for example, Sutcliffe et al., *Science* 219:660 (1983)). Accordingly, antigenic epitope-bearing peptides and polypeptides of the present invention are useful to raise antibodies that bind with the polypeptides described herein.

Antigenic epitope-bearing peptides and polypeptides contain at least four to ten amino acids, preferably at least ten to fifteen amino acids, more preferably 15 to 30 amino acids of SEQ ID NOs:2, 27, 29, 34, 35, 37, and 38. Such epitope-bearing peptides and polypeptides can be produced by fragmenting an UMLR polypeptide, or by chemical peptide synthesis, as described herein. Moreover, epitopes can be selected by phage display of random peptide libraries (see, for example, Lane and Stephen, *Curr. Opin. Immunol.* 5:268 (1993), and Cortese et al., *Curr. Opin. Biotechnol.* 7:616 (1996)). Standard methods for identifying epitopes and producing antibodies from small peptides that comprise an epitope are described, for example, by Mole, "Epitope Mapping," in *Methods in Molecular Biology*, Vol. 10, Manson (ed.), pages 105–116 (The Humana Press, Inc. 1992), Price, "Production and Characterization of Synthetic Peptide-Derived Antibodies," in *Monoclonal Antibodies: Production, Engineering, and Clinical Application*, Ritter and Ladyman (eds.), pages 60–84 (Cambridge University Press 1995), and Coligan et al. (eds.), *Current Protocols in Immunology*, pages 9.3.1–9.3.5 and pages 9.4.1–9.4.11 (John Wiley & Sons 1997).

UMLR polypeptides can also be used to prepare antibodies that specifically bind to UMLR epitopes, peptides or polypeptides. The UMLR polypeptide or a fragment thereof serves as an antigen (immunogen) to inoculate an animal and elicit an immune response. One of skill in the art would recognize that antigenic, epitope-bearing polypeptides contain a sequence of at least 6, preferably at least 9, and more preferably at least 15 to about 30 contiguous amino acid residues of a UMLR polypeptide (e.g., SEQ ID NOs:2, 27, 29, 34, 35, 37, and 38). Polypeptides comprising a larger portion of a UMLR polypeptide, i.e., from 30 to 10 residues up to the entire length of the amino acid sequence are included. Antigens or immunogenic epitopes can also include attached tags, adjuvants and carriers, as described herein. Suitable antigens include the UMLR polypeptides encoded by SEQ ID NO:2 from amino acid number 1 to amino acid number 269; polypeptides encoded by SEQ ID NO:27 from amino acid number 1 to amino acid number 297; polypeptides encoded by SEQ ID NO:35 from amino acid number 1 to amino acid number 299; polypeptides encoded by SEQ ID NO:38 from amino acid number 1 to amino acid number 173, or a contiguous 9 to 269 amino acid fragment thereof.

As an illustration, potential antigenic sites in UMLR were identified using the Jameson-Wolf method, Jameson and Wolf, *CABIOS* 4:181, (1988), as implemented by the PROTEAN program (version 3.14) of LASERGENE (DNASTAR; Madison, Wis.). Default parameters were used in this analysis.

Suitable antigens from this analysis include residue 4 to residue 13 of SEQ ID NO:2; residue 17 to residue 39 of SEQ ID NO:2; residue 44 to residue 60 of SEQ ID NO:2; residue 69 to residue 104 of SEQ ID NO:2; residue 106 to residue 115 of SEQ ID NO:2; residue 128 to residue 136 of SEQ ID NO:2; residue 165 to residue 174 of SEQ ID NO:2; residue 179 to residue 204 of SEQ ID NO:2; and residue 245 to residue 260 of SEQ ID NO:2. Suitable antigens from this analysis of SEQ ID NOs:35 and 38 include residue 181 to residue 210 of SEQ ID NO:35; residue 219 to residue 226 of SEQ ID NO:35; residue 218 to residue 236 of SEQ ID NO:35; and residue 162 to residue 169 of SEQ ID NO:38; and residue 149 to residue 173 of SEQ ID NO:38. Hydrophilic peptides, such as those predicted by one of skill in the art from a hydrophobicity plot are also immonogenic. UMLR hydrophilic peptides include peptides comprising amino acid sequences selected from the group consisting of: residues 1 to 13 of SEQ ID NO:2; residues 21 to 38 of SEQ ID NO:2; residues 44 to 59 of SEQ ID NO:2; residues 88 to 99 of SEQ ID NO:2; residues 165 to 173 of SEQ ID NO:2; residues 194 to 205 of SEQ ID NO:2; residues 213 to 221 of SEQ ID NO:2; residue 194 to residue 236 of SEQ ID NO:35; and residue 150 to residue 171 of SEQ ID NO:38. Regions of the polypeptide, which are likely to be on the surface of the folded protein, are also likely to be antigenic. These regions include: residue 230 to residue 235 of SEQ ID NO:35; and residue 151 to residue 158 of SEQ ID NO:38. Antibodies from an immune response generated by inoculation of an animal with these antigens can be isolated and purified as described herein. Methods for preparing and isolating polygonal and monoclonal antibodies are well known in the art. See, for example, *Current Protocols in Immunology*, Cooligan, et al. (eds.), National Institutes of Health, John Wiley and Sons, Inc., 1995; Sambrook et al., *Molecular Cloning: A Laboratory Manual, Second Edition*, Cold Spring Harbor, N.Y., 1989; and Hurrell, J. G. R., Ed., *Monoclonal Hybridoma Antibodies: Techniques and Applications*, CRC Press, Inc., Boca Raton, Fla., 1982.

As would be evident to one of ordinary skill in the art, polyclonal antibodies can be generated from inoculating a variety of warm-blooded animals such as horses, cows, goats, sheep, dogs, chickens, rabbits, mice, and rats with a UMLR polypeptide or a fragment thereof. The immunogenicity of a UMLR polypeptide may be increased through the use of an adjuvant, such as alum (aluminum hydroxide) or Freund's complete or incomplete adjuvant. Polypeptides useful for immunization also include fusion polypeptides, such as fusions of UMLR or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as $F(ab')_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced.

Alternative techniques for generating or selecting antibodies useful herein include in vitro exposure of lymphocytes to UMLR protein or peptide, and selection of antibody display libraries in phage or similar vectors (for instance, through use of immobilized or labeled UMLR protein or peptide). Genes encoding polypeptides having potential UMLR polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from CLONTECH Laboratories, Inc., (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the UMLR sequences disclosed herein to identify proteins which bind to UMLR. These "binding proteins" which interact with UMLR polypeptides can be used for tagging cells; for isolating homolog polypeptides by affinity purification; they can be directly or indirectly conjugated to drugs, toxins, radionuclides and the like. These binding proteins can also be used in analytical methods such as for screening expression libraries and neutralizing activity. The binding proteins can also be used for diagnostic assays for determining circulating levels of polypeptides; for detecting or quantitating soluble polypeptides as marker of underlying pathology or disease. These binding proteins can also act as UMLR "antagonists" to block UMLR binding and signal transduction in vitro and in vivo. These anti-UMLR binding proteins would be useful for modulating, for example, apoptosis, myogenesis, immunologic recognition, tumor formation, and cell-cell interactions in general.

As used herein, the term "binding proteins" additionally includes antibodies to UMLR polypeptides, the cognate ligand of UMLR polypeptides, proteins useful for purification of UMLR polypeptides, and proteins associated with the cytoplasmic domain (residues 137 to 269 of SEQ ID NO:2; residues 137 to 297 of SEQ ID NO:27; residues 137 to 299 of SEQ ID NO:35, and residues 137 to 173 of SEQ ID NO:38). Such cytoplasmic domain associated peptides, also called cytoplasmic mediators, function in intracellular signaling of UMLR polypeptides. See Bazzoni, F. et al., *J. of Inflammation* 45:221–238, 1995. These cytoplasmic mediators include, but are not limited to TRAP-1, TRADD, RIP, TRAF-1, TRAF-2, LAP-1, FADD/MORT-1, and CAP-1.

Antibodies are determined to be specifically binding if they exhibit a threshold level of binding activity (to a UMLR polypeptide, peptide or epitope) of at least 10-fold greater than the binding affinity to a control (non-UMLR) polypeptide. The binding affinity of an antibody can be readily determined by one of ordinary skill in the art, for example, by Scatchard analysis (Scatchard, G., *Ann. NY Acad. Sci.* 51: 660–672, 1949).

A variety of assays known to those skilled in the art can be utilized to detect antibodies which specifically bind to UMLR proteins or peptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radioimmunoassay, radioimmunoprecipitation, enzyme-linked immunosorbent assay (ELISA), dot blot or Western blot assay, inhibition or competition assay, and sandwich assay. In addition, antibodies can be screened for binding to wild-type versus mutant UMLR protein or polypeptide.

Antibodies to UMLR may be used for immunohistochemical tagging cells that express UMLR; for isolating UMLR by affinity purification; for diagnostic assays for determining circulating levels of UMLR polypeptides; for detecting or quantitating soluble UMLR as marker of underlying pathology or disease; in analytical methods employing FACS; for screening expression libraries; for generating anti-idiotypic antibodies; and as neutralizing antibodies or as antagonists to block UMLR in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications. Moreover, antibodies to UMLR or fragments thereof may be used in vitro to detect denatured UMLR or fragments thereof in assays, for example, Western Blots or other assays known in the art.

The soluble UMLR is useful in studying the distribution of ligands on tissues or specific cell lineages, and to provide insight into receptor/ligand biology. Using labeled UMLR, cells expressing the ligand are identified by fluorescence immunocytometry or immunocytochemistry. Application may also be made of the specificity of TNF receptors for their ligands.

Antibodies can be made to soluble UMLR polypeptides which are His or FLAG™ tagged. Alternatively, such polypeptides form a fusion protein with Human Ig. In particular, antiserum containing polypeptide antibodies to His-tagged, or FLAG™-tagged soluble UMLR can be used in analysis of tissue distribution of UMLR by immunohistochemistry on human or primate tissue. These soluble UMLR polypeptides can also be used to immunize mice in order to produce monoclonal antibodies to a soluble human UMLR polypeptide. Monoclonal antibodies to a soluble human UMLR polypeptide can also be used to mimic ligand/receptor coupling, resulting in activation or inactivation of the ligand/receptor pair. For instance, it has been demonstrated that cross-linking anti-soluble CD40 monoclonal antibodies provides a stimulatory signal to B cells that have been sub-optimally activated with anti-IgM or LPS, and results in proliferation and immunoglobulin production. These same monoclonal antibodies act as antagonists when used in solution by blocking activation of the receptor. Monoclonal antibodies to UMLR can be used to determine the distribution, regulation and biological interaction of the UMLR/UMLR-ligand pair on specific cell lineages identified by tissue distribution studies.

Soluble receptors or antibodies to the receptor can also be directly or indirectly conjugated to drugs, toxins, radionuclides and the like, and these conjugates used for in vivo diagnostic or therapeutic applications. For instance, polypeptides or antibodies of the present invention can be used to identify or treat tissues or organs that express a corresponding anti-complementary molecule (ligand or antigen, respectively, for instance). More specifically, UMLR polypeptides or anti-UMLR antibodies, or bioactive fragments or portions thereof, can be coupled to detectable or cytotoxic molecules and delivered to a mammal having cells, tissues or organs that express the anti-complementary molecule.

Suitable detectable molecules may be directly or indirectly attached to the polypeptide or antibody, and include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, *diphtheria* toxin, *Pseudomonas* exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Polypeptides or antibodies may also be conjugated to cytotoxic drugs, such as adriamycin. For indirect attachment of a detectable or cytotoxic molecule, the detectable or cytotoxic molecule can be conjugated with a member of a complementary/anti-complementary pair, where the other member is bound to the polypeptide or antibody portion. For these purposes, biotin/streptavidin is an exemplary complementary/anticomplementary pair.

In another embodiment, polypeptide-toxin fusion proteins or antibody-toxin fusion proteins can be used for targeted cell or tissue inhibition or ablation (for instance, to treat cancer or inflammatory cells or tissues). Alternatively, a fusion protein including only the cysteine-rich pseudo-repeats may be suitable for directing a detectable molecule, a cytotoxic molecule or a complementary molecule to a cell or tissue type of interest. Similarly, the corresponding ligand to UMLR can be conjugated to a detectable or cytotoxic molecule and provide a generic targeting vehicle for cell/ tissue-specific delivery of generic anti-complementary-detectable/cytotoxic molecule conjugates.

As would be evident to one of skill in the art, certain molecular markers can aid in identifying the existence and prognosis of disease. Such markers include, for example, p53, C-Ki-ras, and c-erbB-2. See, in general, Schneider, P. et al. *Br. J. Cancer* 83(4): 473–479, 2000; and Watatani, M., et al., *Surg. Today* 30(6):516–522, 2000. One of routine skill in the art will also know that such molecular markers can also be used as a target for treatment with or with out combination therapy with other agents, including chemotherapy. An example of a treatment approach to a membrane bound receptor is the use of trastuzumab to treat breast cancer wherein the cancerous tissue is overexpressing HER2. See, for example, Baselga, J., et al., *Semin. Oncol.* 26 (4 Suppl 12): 78–83, 1999; Ravdin, P., *Semin. Oncol.* 26 (4 Suppl 12): 117–23, 1999; Shak, S., *Semin. Oncol.* 26 (4 Suppl 12): 71–7, 1999; and Stebbing, J., et al., *Cancer Treat. Rev.* 26(4): 287–290, 2000.

As a protein that shows upregulation in some tumor cells, such as, for example, melanoma, lung carcinoma, breast carcinoma, osteosarcoma, and lymphoma, polynucleotides and polypeptides of the present invention, fragments thereof, and binding proteins thereto (including antibodies, and ligands) can be used in a multitude of ways to detect and/or diagnose such diseases. For example, polynucleotide probes, (including DNA, RNA, and peptide-nucleic acid) can be used as a diagnostic marker to determine if such disease tissues are present. Hybridization techniques are taught elsewhere in this application and are widely known by one of skill in the art. Such polynucleotides, fragments thereof, and fusions thereto, can also be used to incorporate the proper polynucleotide sequence into a tissue, cell line or organism defective in the proper gene, as is also taught elsewhere in this application. As a means of treating such disease, said polunucleotides, fragments thereof, and fusions thereto, can also be administered in the presence of an agent that allows the DNA to traverse the cell membrane and act as a tag for cell ablation to a therapeutic agent with an appropriate binding partner. In this manner cells which contain ztnfr11 polynucleotides can be inhibited or destroyed.

Ztnfr11 polypeptides, fragments thereof, and fusions thereto, can be used both diagnostically and therapeutically. Such ztnfr11 polypeptides, including soluble polypeptides, can be used as a marker for identifying tumor cells, such as, for example, melanoma, lung carcinoma, breast carcinoma, osteosarcoma, and lymphoma. As a soluble polypeptide, this diagnosis can be determined by measuring ztnfr11 polypeptides, fragments thereof, and fusions thereto in body fluids, including, but not limited to, blood, plasma, saliva, urine, lavage fluid and biopsy fluid. As a membrane bound polypeptide ztnfr11 polypeptides, fragments thereof, and fusions thereto, can be measured in tissue biopsies (i.e., excised from the body) as well as locally (i.e., epithlelial surfaces) using imaging and/or visualization. The targeting of such disease tissues will be helpful in treatment options. For example, if the spread of disease is limited, such visualization will aid a surgeon in resection of disease tissue. Similarly, the presence of membrane bound ztnfr11 can be used as a target for a ztnfr11 binding protein (including its ligand or antibodies) that has been fused or conjugated to an inhibitory or ablative agent.

In another embodiment, UMLR-cytokine fusion proteins or antibody-cytokine fusion proteins can be used for enhancing in vivo killing of target tissues (for example, uterus, as well as in melanoma, osteosarcoma, breast carcinoma, and lymphoma, and in tumors of the lung), if the UMLR polypeptide or anti-UMLR antibody targets hyperproliferative tissues from these organs. (See, generally, Hornick et al., *Blood* 89:4437–47, 1997). They described fusion proteins that enable targeting of a cytokine to a desired site of action, thereby providing an elevated local concentration of cytokine. Suitable UMLR polypeptides or anti-UMLR antibodies target an undesirable cell or tissue (i.e., a tumor or a leukemia), and the fused cytokine mediates improved target cell lysis by effector cells. Suitable cytokines for this purpose include interleukin 2 and granulocyte-macrophage colony-stimulating factor (GM-CSF), for instance.

UMLR polynucleotides and/or polypeptides may be useful for regulating the maturation of TNF ligand-bearing cells, such as T cells, B cells, lymphocytes, peripheral blood mononuclear cells, polymorphonuclear leukocytes, fibroblasts and hematopoietic cells. UMLR polypeptides will also find use in mediating metabolic or physiological processes in vivo. The effects of a compound on proliferation and differentiation can be measured in vitro using cultured cells. Bioassays and ELISAs are available to measure cellular response to UMLR, in particular are those which measure changes in cytokine production as a measure of cellular response (see for example, *Current Protocols in Immunology* ed. John E. Coligan et al., NIH, 1996). Assays to measure other cellular responses, including antibody isotype, monocyte activation. NK cell formation, antigen presenting cell function, apoptosis are known in the art.

The UMLR polypeptides of the present invention, including full-length polypeptides, biologically active fragments, and fusion polypeptides, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., *Molecular Cloning: A Laboratory Manual*, 2nd ed., Cold Spring Harbor Laboratory Press, Cold Spring Harbor, N.Y., 1989, and Ausubel et al., eds., *Current Protocols in Molecular Biology*, John Wiley and Sons, Inc., NY, 1987.

In general, a DNA sequence encoding a UMLR polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a UMLR polypeptide into the secretory pathway of a host cell, a secretory signal sequence (also known as a leader sequence, prepro sequence or pre sequence) can be provided in the expression vector. The secretory signal sequence may be derived from another secreted protein (e.g., APO4, or t-PA) or synthesized de novo. The secretory signal sequence is operably linked to the UMLR DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain secretory signal sequences may be positioned elsewhere in the DNA sequence of interest (see, e.g., Welch et al., U.S. Pat. No. 5,037,743; Holland et al., U.S. Pat. No. 5,143,830).

The cytoplasmic domain of UMLR can be substituted by a heterologous sequence providing a different cytoplasmic domain. In this case, the fusion product can be secreted, and the cysteine-rich pseudo-repeat domain of UMLR can direct the new cytoplasmic domain to a specific tissue described above. This substituted cytoplasmic domain can be chosen from the cytoplasmic domain represented by the TNFR protein families. Similarly, the cysteine-rich pseudo-repeat domain of UMLR protein can be substituted by a heterlogous sequence providing a different cysteine-rich pseudo-repeat domain. Again, the fusion product can be secreted and the substituted cysteine-rich pseudo-repeat domain can target the cytoplasmic domain of UMLR to a specific tissue. The substituted cysteine-rich pseudo-repeat domain can be chosen from the cysteine-rich pseudo-repeat domains of the TNFR protein families. In these cases, the fusion products can be soluble or membrane-bound proteins.

Cultured mammalian cells are suitable hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841–5, 1982), DEAE-dextran mediated transfection (Ausubel et al., ibid.), and liposome-mediated transfection (Hawley-Nelson et al., *Focus* 15:73, 1993; Ciccarone et al., *Focus* 15:80, 1993, and viral vectors (Miller and Rosman, *BioTechniques* 7:980–90, 1989; Wang and Finer, *Nature Med.* 2:714–6, 1996). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59–72, 1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g., hygromycin resistance, multi-drug resistance, puromycin acetyltransferase) can also be used. Alternative markers that introduce an altered phenotype, such as green fluorescent protein, or cell surface proteins, such as CD4, CD8, Class I MHC, or placental alkaline phosphatase, may be used to sort transfected cells from untransfected cells by such means as FACS sorting or magnetic bead separation technology.

Other higher eukaryotic cells can also be used as hosts, including plant cells, insect cells and avian cells. The use of *Agrobacterium rhizogenes* as a vector for expressing genes in plant cells has been reviewed by Sinkar et al., *J. Biosci.* (Bangalore) 11:47–58, 1987. Transformation of insect cells and production of foreign polypeptides therein is disclosed by Guarino et al., U.S. Pat. No. 5,162,222 and WIPO publication WO 94/06463. Insect cells can be infected with recombinant baculovirus, commonly derived from *Autographa californica* nuclear polyhedrosis virus (AcNPV). See, King, L. A. and Possee, R. D., *The Baculovirus Expression System: A Laboratory Guide*, London, Chapman & Hall; O'Reilly, D. R. et al., *Baculovirus Expression Vectors: A Laboratory Manual*, New York, Oxford University Press., 1994; and, Richardson, C. D., Ed., *Baculovirus Expression Protocols. Methods in Molecular Biology*, Totowa, N.J., Humana Press, 1995. A second method of making recombinant UMLR baculovirus utilizes a transposon-based system described by Luckow (Luckow, V. A, et al., *J Virol* 67:4566–79, 1993). This system, which utilizes transfer vectors, is sold in the Bac-to-Bac™ kit (Life Technologies, Rockville, Md.). This system utilizes a transfer vector, pFastBac1™ (Life Technologies) containing a Tn7 transposon to move the DNA encoding the UMLR polypeptide into a baculovirus genome maintained in *E. coli* as a large plasmid called a "bacmid." The pFastBac1™ transfer vector utilizes the AcNPV polyhedrin promoter to drive the expression of the gene of interest, in this case UMLR. However, pFastBac1™ can be modified to a considerable degree. The polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins. See, Hill-Perkins, M. S. and Possee, R. D., *J. Gen. Virol.* 71:971–6, 1990; Bonning, B. C. et al., *J. Gen. Virol.* 75:1551–6, 1994; and, Chazenbalk, G. D., and Rapoport, B., *J. Biol Chem* 270:1543–9, 1995. In such transfer vector constructs, a short or long version of the basic protein promoter can be used. Moreover, transfer vectors can be constructed which replace the native UMLR secretory signal sequences with secretory signal sequences derived from insect proteins. For example, a secretory signal sequence from Ecdysteroid Glucosyltransferase (EGT), honey bee Melittin (Invitrogen, Carlsbad, Calif.), or baculovirus gp67 (PharMingen, San Diego, Calif.) can be used in constructs to replace the native UMLR secretory signal sequence. In addition, transfer vectors can include an in-frame fusion with DNA encoding an epitope tag at the C- or N-terminus of the expressed UMLR polypeptide, for example, a Glu-Glu epitope tag (Grussenmeyer, T. et al., *Proc. Natl. Acad. Sci.* 82:7952–4, 1985). Using a technique known in the art, a transfer vector containing UMLR is transformed into *E. coli*, and screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, e.g. Sf9 cells. Recombinant virus that expresses UMLR is subsequently produced. Recombinant viral stocks are made by methods commonly used the art.

The recombinant virus is used to infect host cells, typically a cell line derived from the fall armyworm, *Spodoptera frugiperda*. See, in general, Glick and Pasternak, *Molecular Biotechnology: Principles and Applications of Recombinant DNA*, ASM Press, Washington, D.C., 1994. Another suitable cell line is the High FiveO™ cell line (Invitrogen) derived from *Trichoplusia ni* (U.S. Pat. No. 5,300,435). Commercially available serum-free media are used to grow and maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. The cells are grown up from an inoculation density of approximately $2–5\times10^5$ cells to a density of $1–2\times10^6$ cells at which time a recombinant viral stock is added at a multiplicity of infection (MOI) of 0.1 to 10, more typically near 3. Procedures used are generally described in available laboratory manuals (King, L. A. and Possee, R. D., ibid.; O'Reilly, D. R. et al., ibid.; Richardson, C. D., ibid.). Subsequent purification of the UMLR polypeptide from the supernatant can be achieved using methods described herein.

Fungal cells, including yeast cells, can also be used within the present invention. Yeast species of particular interest in this regard include *Saccharomyces cerevisiae, Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459–65, 1986 and Cregg, U.S. Pat. No. 4,882,279. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533. The use of *Pichia methanolica* as host for the production of recombinant proteins is disclosed in U.S. Pat. Nos. 5,716,808, 5,736,383, 5,854,039, and 5,888,768.

Prokaryotic host cells, including strains of the bacteria *Escherichia coli, Bacillus* and other genera are also useful host cells within the present invention. Techniques for transforming these hosts and expressing foreign DNA sequences cloned therein are well known in the art (see, e.g., Sambrook et al., ibid.). When expressing a UMLR polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine and 0.006% L-leucine).

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806–9, 1993; and Chung et al., *Proc. Natl. Acad. Sci. USA* 90:10145–9, 1993). In a second method, translation is carried out in *Xenopus* oocytes by microinjection of mutated mRNA and chemically aminoacylated suppressor tRNAs (Turcatti et al., *J. Biol. Chem.* 271:19991–8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470–6, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395–403, 1993).

A limited number of non-conservative amino acids, amino acids that are not encoded by the genetic code, non-naturally occurring amino acids, and unnatural amino acids may be substituted for UMLR amino acid residues.

It is preferred to purify the polypeptides of the present invention to ≧80% purity, more preferably to ≧90% purity, even more preferably ≧95% purity, and particularly preferred is a pharmaceutically pure state, that is greater than 99.9% pure with respect to contaminating macromolecules, particularly other proteins and nucleic acids, and free of infectious and pyrogenic agents. Preferably, a purified polypeptide is substantially free of other polypeptides, particularly other polypeptides of animal origin.

Expressed recombinant UMLR proteins (including chimeric polypeptides and multimeric proteins) are purified by conventional protein purification methods, typically by a combination of chromatographic techniques. See, in general, *Affinity Chromatography: Principles & Methods*, Pharmacia LKB Biotechnology, Uppsala, Sweden, 1988; and Scopes, *Protein Purification: Principles and Practice*, Springer-Verlag, New York, 1994. Proteins comprising a polyhistidine affinity tag (typically about 6 histidine residues) are purified by affinity chromatography on a nickel chelate resin. See, for example, Houchuli et al., *Bio/Technol.* 6:1321–1325, 1988. Proteins comprising a glu-glu tag can be purified by immunoaffinity chromatography according to conventional procedures. See, for example, Grussenmeyer et al., ibid. Maltose binding protein fusions are purified on an amylose column according to methods known in the art.

The polypeptides of the present invention can be isolated by a combination of procedures including, but not limited to, anion and cation exchange chromatography, size exclusion, and affinity chromatography. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1–7, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (*Methods in Enzymol.*, Vol. 182, "Guide to Protein Purification", M. Deutscher, (ed.), Acad. Press, San Diego, 1990, pp. 529–39). Within additional embodiments of the invention, a fusion of the polypeptide of interest and an affinity tag (e.g., maltose-binding protein, an immunoglobulin domain) may be constructed to facilitate purification.

UMLR polypeptides can also be prepared through chemical synthesis according to methods known in the art, including exclusive solid phase synthesis, partial solid phase methods, fragment condensation or classical solution synthesis. See, for example, Merrifield, *J. Am. Chem. Soc.* 85:2149, 1963; Stewart et al., *Solid Phase Peptide Synthesis* (2nd edition), Pierce Chemical Co., Rockford, Ill., 1984; Bayer and Rapp, *Chem. Pept. Prot.* 3:3, 1986; and Atherton et al., *Solid Phase Peptide Synthesis: A Practical Approach*, IRL Press, Oxford, 1989. In vitro synthesis is particularly advantageous for the preparation of smaller polypeptides.

Using methods known in the art, UMLR proteins can be prepared as monomers or multimers; glycosylated or non-glycosylated; pegylated or non-pegylated; and may or may not include an initial methionine amino acid residue.

The activity of UMLR polypeptides can be measured using a variety of assays that measure, for example, cell-cell interactions, apoptosis, inflammation, anti-infective capabilities and other biological functions associated with TNFR family members or with TNFR interactions, such as, differentiation, and proliferation for example. Of particular interest is a change in inflammation. Assays measuring inflammation are well known in the art.

Proteins, including alternatively spliced peptides, of the present invention are useful for tumor suppression, immunologic recognition, and growth and differentiation either working in isolation, or in conjunction with other molecules (growth factors, cytokines, etc.) in uterus, as well as in melanoma, osteosarcoma, breast carcinoma, and lymphoma, and in tumors of the lung. Alternative splicing of UMLR may cell-type specific and confer activity to specific tissues.

As polynucleotides of the present invention have been identified in lung carcinoma, melanoma, osteosarcoma, breast carcinoma, and lymphoma cells, polynucleotides of UMLR can be used to detect these cell types by hybridization, or with UMLR binding proteins. Similarly antibodies to the UMLR polypeptides can detect cells expressing the surface bound UMLR receptor. Such detection can be useful to determine metastasis, disease stage, or primary diagnosis of disease. Additionally, proliferation, differentiation and/or apoptosis of these cell types can be modulated by contacting the cells with UMLR binding proteins, including a UMLR-cognate ligand, or an antibody to UMLR, for example. The proliferation, differentiation and/or apoptosis of such cells can also be mediated by UMLR polypeptides, or fragments thereof, as an antagonist of cell signaling by binding the ligand and thereby reducing the interaction between ligand and membrane-bound UMLR proteins. The effects of the modulation of UMLR molecules on proliferation, differentiation and/or apoptosis can be measured, for example, by the presence or absence of cell markers specific to these cell types, or by measuring other manifestations of these diseases. For example, UMLR polypeptides or fragments thereof, as well as UMLR binding proteins can be administered to cells of lung carcinoma and inhibition of the carcinoma can be monitored by conventional imaging techniques.

Another assay of interest measures or detects changes in proliferation, differentiation, and development. Additionally, the effects of a UMLR polypeptides on cell-cell interactions of fibroblasts, epithelial cells, tumor cells and cells of the genito-urinary tract in particular, would be of interest to measure. Yet other assays examines changes in apoptosis, and intracellular signaling.

The activity of molecules of the present invention can be measured using a variety of assays that, for example, measure neogenesis or hyperplasia (i.e., proliferation) of tissues of the uterus, lung carcinoma, or breast carcinoma, as well as cells of melanoma, osteosarcoma, and lymphoma. Additional activities likely associated with the polypeptides of the present invention include proliferation of endothelial cells, fibroblasts, and lymphoid cells directly or indirectly through other growth factors; action as a chemotaxic factor for endothelial cells, fibroblasts and/or phagocytic cells; osteogenic factor; and factor for expanding mesenchymal stem cell and precursor populations.

The UMLR polypeptides of the present invention can be used to study proliferation or differentiation in uterus, as well as in melanoma, osteosarcoma, breast carcinoma, and lymphoma, and in tumors of the lung. Such methods of the present invention generally comprise incubating cells derived from these tissues in the presence and absence of UMLR polypeptide, monoclonal antibody, agonist or antagonist thereof and observing changes in cell proliferation or differentiation. Cell lines from these tissues are commercially available from, for example, American Type Culture Collection (Manasas, Va.).

Proliferation can be measured using cultured uterine or lung cells or in vivo by administering molecules of the claimed invention to an appropriate animal model. Generally, proliferative effects are observed as an increase in cell number and therefore, may include inhibition of apoptosis, as well as mitogenesis. Cultured cells include uterine fibroblasts, lung tumors, and melanoma, osteosarcoma, breast carcinoma, and lymphoma, as well as from primary cultures. Established cell lines are easily identifiable by one skilled in the art and are available from ATCC (Manasas, Va.). Assays measuring cell proliferation are well known in the art. For example, assays measuring proliferation include such assays as chemosensitivity to neutral red dye (Cavanaugh et al., *Investigational New Drugs* 8:347–354, 1990), incorporation of radiolabelled nucleotides (Cook et al., *Analytical Biochem.* 179:1–7, 1989), incorporation of 5-bromo-2'-deoxyuridine (BrdU) in the DNA of proliferating cells (Porstmann et al., *J. Immunol. Methods* 82:169–179, 1985), and use of tetrazolium salts (Mosmann, *J. Immunol. Methods* 65:55–63, 1983; Alley et al., *Cancer Res.* 48:589–601, 1988; Marshall et al., *Growth Reg.* 5:69–84, 1995; and Scudiero et al., *Cancer Res.* 48:4827–4833, 1988).

To determine if UMLR is a chemotractant in vivo, UMLR can be given by intradermal or intraperitoneal injection. Characterization of the accumulated leukocytes at the site of injection can be determined using lineage specific cell surface markers and fluorescence immunocytometry or by immunohistochemistry (Jose, *J. Exp. Med.* 179:881–87, 1994). Release of specific leukocyte cell populations from bone marrow into peripheral blood can also be measured after UMLR injection.

Differentiation is a progressive and dynamic process, beginning with pluripotent stem cells and ending with terminally differentiated cells. Pluripotent stem cells that can regenerate without commitment to a lineage express a set of differentiation markers that are lost when commitment to a cell lineage is made. Progenitor cells express a set of differentiation markers that may or may not continue to be expressed as the cells progress down the cell lineage pathway toward maturation. Differentiation markers that are expressed exclusively by mature cells are usually functional properties such as cell products, enzymes to produce cell products and receptors and receptor-like complementary molecules. The stage of a cell population's differentiation is monitored by identification of markers present in the cell population. For example, myocytes, osteoblasts, adipocytes, chrondrocytes, fibroblasts and reticular cells are believed to originate from a common mesenchymal stem cell (Owen et al., *Ciba Fdn. Symp.* 136:42–46, 1988). Markers for mesenchymal stem cells have not been well identified (Owen et al., *J. of Cell Sci.* 87:731–738, 1987), so identification is usually made at the progenitor and mature cell stages. The novel polypeptides of the present invention are useful for studies to isolate mesenchymal stem cells and uterine myocyte progenitor cells, both in vivo and ex vivo.

There is evidence to suggest that factors that stimulate specific cell types down a pathway towards terminal differentiation or dedifferentiation affect the entire cell population originating from a common precursor or stem cell. Thus, UMLR polypeptides may stimulate inhibition or proliferation of endocrine and exocrine cells of the uterus, as well as in melanoma, osteosarcoma, breast carcinoma, and lymphoma, and in tumors of the lung.

Molecules of the present invention may, while stimulating proliferation or differentiation of uterine fibroblasts, inhibit proliferation or differentiation of adipocytes, by virtue of their effect on common precursor/stem cells. The novel polypeptides of the present invention are useful to study neural and epithelial stem cells and uterus, as well as in melanoma, osteosarcoma, breast carcinoma, and lymphoma, and in tumors in lung progenitor cells, both in vivo and ex vivo.

Assays measuring differentiation include, for example, measuring cell-surface markers associated with stage-specific expression of a tissue, enzymatic activity, functional activity or morphological changes (Watt, *FASEB*, 5:281–284, 1991; Francis, *Differentiation* 57:63–75, 1994; Raes, *Adv. Anim. Cell Biol. Technol. Bioprocesses,* 161–171, 1989).

Proteins, including alternatively spliced peptides, and fragments, of the present invention are useful for studying cell-cell interactions, fertilization, development, immune recognition, growth control, tumor suppression, and embryo maturation. UMLR molecules, variants, and fragments can be applied in isolation, or in conjunction with other molecules (growth factors, cytokines, etc.) in uterus, as well as in melanoma, osteosarcoma, breast carcinoma, and lymphoma, and in tumors of the lung.

Proteins of the present invention are useful for delivery of therapeutic agents such as, but not limited to, proteases, radionuclides, chemotherapy agents, and small molecules. Effects of these therapeutic agents can be measured in vitro using cultured cells, ex vivo on tissue slices, or in vivo by administering molecules of the claimed invention to the appropriate animal model. An alternative in vivo approach for assaying proteins of the present invention involves viral delivery systems. Exemplary viruses for this purpose include adenovirus, herpesvirus, lentivirus, vaccinia virus and adeno-associated virus (AAV). Adenovirus, a double-stranded DNA virus, is currently the best studied gene transfer vector for delivery of heterologous nucleic acid (for a review, see T. C. Becker et al., *Meth. Cell Biol.* 43:161–89, 1994; and J. T. Douglas and D. T. Curiel, *Science & Medicine* 4:44–53, 1997). The adenovirus system offers several advantages: adenovirus can (i) accommodate relatively large DNA inserts; (ii) be grown to high-titer; (iii) infect a broad range of mammalian cell types; and (iv) be used with a large number of available vectors containing different promoters. Also, because adenoviruses are stable in the bloodstream, they can be administered by intravenous injection.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. In an exemplary system, the essential E1 gene has been deleted from the viral vector, and the virus will not replicate unless the E1 gene is provided by the host cell (the human 293 cell line is exemplary). When intravenously administered to intact animals, adenovirus primarily targets the liver. If the adenoviral delivery system has an E1 gene deletion, the virus cannot replicate in the host cells. However, the host's tissue (e.g., liver) will express and process (and, if a secretory signal sequence is present, secrete) the heterologous protein. Secreted proteins will enter the circulation in the highly vascularized liver, and effects on the infected animal can be determined.

Moreover, adenoviral vectors containing various deletions of viral genes can be used in an attempt to reduce or eliminate immune responses to the vector. Such adenoviruses are E1 deleted, and in addition contain deletions of E2A or E4 (Lusky, M. et al., *J. Virol.* 72:2022–2032, 1998; Raper, S. E. et al., *Human Gene Therapy* 9:671–679, 1998). In addition, deletion of E2b is reported to reduce immune responses (Amalfitano, A. et al., *J. Virol.* 72:926–933, 1998). Moreover, by deleting the entire adenovirus genome, very large inserts of heterologous DNA can be accommodated. Generation of so called "gutless" adenoviruses where all viral genes are deleted are particularly advantageous for insertion of large inserts of heterologous DNA. For review, see Yeh, P. and Perricaudet, M., *FASEB J.* 11:615–623, 1997.

The adenovirus system can also be used for protein production in vitro. By culturing adenovirus-infected non-293 cells under conditions where the cells are not rapidly dividing, the cells can produce proteins for extended periods of time. For instance, BHK cells are grown to confluence in cell factories, then exposed to the adenoviral vector encoding the secreted protein of interest. The cells are then grown under serum-free conditions, which allows infected cells to survive for several weeks without significant cell division. Alternatively, adenovirus vector infected 293S cells can be grown in suspension culture at relatively high cell density to produce significant amounts of protein (see Garnier et al., *Cytotechnol.* 15:145–55, 1994). With either protocol, an expressed, secreted heterologous protein can be repeatedly isolated from the cell culture supernatant. Within the infected 293S cell production protocol, non-secreted proteins may also be effectively obtained.

As a soluble or cell-surface protein, the activity of UMLR polypeptide or a peptide to which UMLR binds, can be measured by a silicon-based biosensor microphysiometer which measures the extracellular acidification rate or proton excretion associated with cell-surface protein interactions and subsequent physiologic cellular responses. An exemplary device is the Cytosensorm™ Microphysiometer manufactured by Molecular Devices, Sunnyvale, Calif. A variety of cellular responses, such as cell proliferation, ion transport, energy production, inflammatory response, regulatory and receptor activation, and the like, can be measured by this method. See, for example, McConnell, H. M. et al., *Science* 257:1906–1912, 1992; Pitchford, S. et al., *Meth. Enzymol.* 228:84–108, 1997; Arimilli, S. et al., *J. Immunol. Meth.* 212:49–59, 1998; Van Liefde, I. et al., *Eur. J. Pharmacol.* 346:87–95, 1998. The microphysiometer can be used for assaying adherent or non-adherent eukaryotic or prokaryotic cells. By measuring extracellular acidification changes in cell media over time, the microphysiometer directly measures cellular responses to various stimuli, including proteins, agonists, and antagonists which affect a UMLR-mediated pathway. UMLR-responsive eukaryotic cells comprise cells into which a polynucleotide for UMLR has been transfected creating a cell that is responsive to activation of UMLR; or cells naturally responsive to activation of UMLR. Differences, measured by a change in the response of cells exposed to UMLR activation, relative to a control not exposed to UMLR activation, are a direct measurement of UMLR-mediated cellular responses. Moreover, such UMLR-mediated responses can be assayed under a variety of stimuli. The present invention provides a method of identifying agonists and antagonists of UMLR protein, comprising providing cells responsive to activation of UMLR polypeptide, culturing a first portion of the cells in the absence of a test compound, culturing a second portion of the cells in the presence of a test compound, and detecting a change in a cellular response of the second portion of the cells as compared to the first portion of the cells. The change in cellular response is shown as a measurable change in extracellular acidification rate. Moreover, culturing a third portion of the cells in the presence of UMLR polypeptide and the absence of a test compound provides a positive control for the UMLR-responsive cells, and a control to compare the agonist activity of a test compound with that of the UMLR polypeptide. Antagonists of UMLR can be identified by exposing the cells to UMLR protein in the presence and absence of the test compound, whereby a reduction in UMLR-stimulated activity is indicative of antagonist activity in the test compound.

Similarly, the microphysiometer, can be used to rapidly identify cells, tissues or cell lines which activate a UMLR-stimulated pathway. Such tissues and cell lines can be used to identify ligands, antagonists and agonists of UMLR polypeptide as described above. Using similar methods, cells expressing UMLR can be used to identify cells which stimulate or block a UMLR-signaling pathway.

UMLR shares homology with OPG, a soluble TNF receptor involved in the regulation of bone density (Simonet et al., ibid.). Well established animal models are available to test the in vivo efficacy of UMLR polypeptides for certain disease states, such as bone-related disorders. For example, the hypocalcemic rat model can be used to determine the effect of UMLR on serum calcium, and the ovariectomized rat or mouse can be used as a model system for osteoporosis. Bone changes seen in these models and in humans during the early stages of estrogen deficiency are qualitatively similar.

In view of the tissue distribution (uterus, lung carcinoma, breast carcinoma, and thymus and pituitary, as well as cells of melanoma, osteosarcoma, and lymphoma) observed for UMLR expression, agonists (including the native cysteine-rich pseudo-repeat and cytoplasmic domains, and antagonists have enormous potential in both in vitro and in vivo applications. Compounds identified as UMLR agonists and antagonists are useful for studying cell-cell interactions, apoptosis, tumor proliferation and suppression, infection, and inflammation in vitro and in vivo. For example, UMLR and agonist compounds are useful as components of defined cell culture media, and may be used alone or in combination with cytokines and hormones to replace serum that is commonly used in cell culture. Agonists are thus useful in specifically promoting the growth and/or development of cells of the myeloid and lymphoid lineages in culture. Additionally, UMLR polypeptides and UMLR agonists, including small molecules are useful as a research reagent, such as for the expansion, differentiation, proliferation, and/or cell-cell interactions of uterus, as well as in melanoma, osteosarcoma, breast carcinoma, and lymphoma, and in tumors of the lung. UMLR polypeptides are added to tissue culture media for these cell types.

Compounds identified as UMLR agonists are useful for modifying the proliferation and development of target cells in vitro and in vivo. For example, agonist compounds are useful alone or in combination with other cytokines and hormones as components of defined cell culture media. Agonists are thus useful in specifically mediating the growth and/or development of UMLR-bearing T lymphocytes or other UMLR-bearing cells in culture. Agonists and antagonists may also prove useful in the study of effector functions of T lymphocytes, in particular T lymphocyte activation and differentiation. Antagonists are useful as research reagents for characterizing ligand-receptor interaction.

As a member of the TNFR family, UMLR polypeptides are likely to be involved in the immune response to infection. Lymphotoxin-beta receptor, another member of this receptor family, has been shown to regulate HIV-1 replication. (Marshall, W. L. et al., *J. Immun.* 162: 6016–6023, 1999). Further, it has been shown that cosignaling via the lymphotoxin-beta receptor and TNF-receptors is probably involved in the modulation of HIV-1 replication and the subsequent determination of HIV-1 viral burden in monocytes. UMLR polypeptides, agonists, and antagonists can be used to treat microbial infections. Such infections include bacterial, yeast, and viral infections. Anti-microbial activity of proteins is evaluated by techniques that are known in the art. For example, anti-microbial activity can be assayed by evaluating the sensitivity of microbial cell cultures to test agents and by evaluating the protective effect of test agents on infected mice. See, for example, Musiek et al., *Antimicrob. Agents Chemothr.* 3:40, 1973. Antiviral activity can also be assessed by protection of mammalian cell cultures. Known techniques for evaluating anti-microbial activity include, for example, Barsum et al., *Eur. Respir. J.* 8:709–714, 1995; Sandovsky-Losica et al., *J. Med. Vet. Mycol* (England) 28:279–287, 1990; Mehentee et al., *J. Gen. Microbiol* (England) 135(:2181–2188, 1989; and Segal and Savage, *J. Med. Vet. Mycol.* 24:477–479, 1986. Assays specific for anti-viral activity include, for example, those described by Daher et al., *J. Virol.* 60:1068–1074, 1986. Similarly, assays measuring HIV-1 viral burden on cells can be used.

Shock is a manifestation of infection. Studies show that increased serum TNF levels are associated with high mortality rates. See Wage, A. et al., *Lancet i:*355–357, 1987, and Girardin et al., *New. Eng. J. Med.* 39: 397–400, 1988. Soluble TNF receptors, including UMLR polypeptides of the present invention, may be useful to reduce serum concentrations of TNF, and minimize the effects of sepsis.

The invention also provides antagonists, which either bind to UMLR polypeptides or, alternatively, to a ligand to which UMLR polypeptides bind, thereby inhibiting or eliminating the function of UMLR. Such UMLR antagonists would include antibodies; polypeptides which bind either to the UMLR polypeptide or to its ligand; natural or synthetic analogs of UMLR ligands which retain the ability to bind the receptor but do not result in either ligand or receptor signaling. Such analogs could be peptides or peptide-like compounds. Natural or synthetic small molecules which bind to UMLR polypeptides and prevent signaling are also contemplated as antagonists. Also contemplated are soluble UMLR receptors. As such, UMLR antagonists would be useful as therapeutics for treating certain disorders where blocking signal from either a UMLR receptor or ligand would be beneficial. Antagonists are useful as research reagents for characterizing ligand-receptor interaction.

UMLR polypeptides may be used within diagnostic systems to detect the presence of ligand polypeptides. Antibodies or other agents that specifically bind to UMLR may also be used to detect the presence of circulating or membrane bound receptor or ligand polypeptides. Such detection methods are well known in the art and include, for example, enzyme-linked immunosorbent assay (ELISA) and radioimmunoassay. Immunohistochemically labeled UMLR antibodies can be used to detect UMLR receptor and/or ligands in tissue samples. UMLR levels can also be monitored by such methods as RT-PCR, where UMLR mRNA can be detected and quantified. The information derived from such detection methods would provide insight into the significance of UMLR polypeptides in various diseases, and as such would serve as diagnostic tools for diseases for which altered levels of UMLR are significant. Altered levels of UMLR receptor polypeptides may be indicative of pathological conditions including cancer, autoimmune disorders, bone disorders, inflammation and immunodeficiencies.

Antagonists are also useful as research reagents for characterizing sites of interactions between members of complement/anti-complement pairs as well as sites of cell-cell interactions. Inhibitors of UMLR activity (UMLR antagonists) include anti-UMLR antibodies and soluble UMLR polypeptides (such as described above), as well as other peptidic and non-peptidic agents (including ribozymes).

UMLR can also be used to identify inhibitors (antagonists) of its activity. Test compounds are added to the assays disclosed herein to identify compounds that inhibit the activity of UMLR. In addition to those assays disclosed herein, samples can be tested for inhibition of UMLR activity within a variety of assays designed to measure receptor/ligand binding or the stimulation/inhibition of UMLR-dependent cellular responses. For example, UMLR-responsive cell lines can be transfected with a reporter gene construct that is responsive to a UMLR-stimulated cellular pathway. Reporter gene constructs of this type are known in the art, and will generally comprise a DNA response element operably linked to a gene encoding an assayable protein, such as luciferase, or a metabolite, such as cyclic AMP. DNA response elements can include, but are not limited to, cyclic AMP response elements (CRE), hormone response elements (HRE), insulin response element (IRE) (Nasrin et al., *Proc. Natl. Acad. Sci. USA* 87:5273–7, 1990) and serum response elements (SRE) (Shaw et al. *Cell* 56: 563–72, 1989). Cyclic AMP response elements are reviewed in Roestler et al., *J. Biol. Chem.* 263 (19):9063–6; 1988 and Habener, *Molec. Endocrinol.* 4 (8):1087–94; 1990. Hormone response elements are reviewed in Beato, *Cell* 56:335–44; 1989. Such a reporter gene construct would contain a cysteine-rich pseudo-repeat that, upon binding a TNF, would signal intracellularly through, for example, a SRE reporter. Candidate compounds, solutions, mixtures or extracts are tested for the ability to inhibit the activity of UMLR on the target cells, as evidenced by a decrease in UMLR stimulation of reporter gene expression. Assays of this type will detect compounds that directly block UMLR binding to a cell-surface protein, i.e., ligand, or the anti-complementary member of a complementary/anti-complementary pair, as well as compounds that block processes in the cellular pathway subsequent to complement/anti-complement binding. In the alternative, compounds or other samples can be tested for direct blocking of UMLR binding to a ligand using UMLR tagged with a detectable label (e.g., $^{125}$I, biotin, horseradish peroxidase, FITC, and the like). Within assays of this type, the ability of a test sample to inhibit the binding of labeled UMLR to the TNF is indicative of inhibitory activity, which can be confirmed through secondary assays. TNFs used within binding assays may be cellular TNFs, soluble TNFs, or isolated, immobilized TNFs.

Also, UMLR polypeptides, agonists or antagonists thereof may be therapeutically useful for promoting wound healing, for example, in uterus, as well as in melanoma, osteosarcoma, breast carcinoma, and lymphoma, and in tumors of the lung. To verify the presence of this capability in UMLR polypeptides, agonists or antagonists of the present invention, such UMLR polypeptides, agonists or antagonists are evaluated with respect to their ability to facilitate wound healing according to procedures known in the art. If desired, UMLR polypeptide performance in this regard can be compared to growth factors, such as EGF, NGF, TGF-α, TGF-β, insulin, IGF-I, IGF-II, fibroblast growth factor (FGF) and the like. In addition, UMLR polypeptides or agonists or antagonists thereof may be evaluated in combination with one or more growth factors to identify synergistic effects.

The activity of agonists and antagonists can be determined by activity assays which determine the potency of receptor/ligand engagement. Stably transfected cell lines, which co-express high levels of reporter gene constructs for NfKB, NFAT-1 and AP-1 can be made which express ztnfr11. A ztnfr11 ligand can be found to signal through the reporter genes in these constructs. Soluble ztnfr11 and antibodies can be used to measure binding.

A UMLR ligand-binding polypeptide can also be used for purification of ligand. The polypeptide is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting medium will generally be configured in the form of a column, and fluids containing ligands are passed through the column one or more times to allow ligands to bind to the receptor polypeptide. The ligand is then eluted using changes in salt concentration, chaotropic agents (guanidine HCl), or pH to disrupt ligand-receptor binding.

An assay system that uses a ligand-binding receptor (or an antibody, one member of a complementary/anti-complementary pair or other cell-surface binding protein) or a binding fragment thereof, and a commercially available biosensor instrument (BIAcore, Pharmacia Biosensor, Piscataway, N.J.) may be advantageously employed. Such receptor, antibody, member of a complement/anti-complement pair or fragment is immobilized onto the surface of a receptor chip. Use of this instrument is disclosed by Karlsson, *J. Immunol. Methods* 145:229–40, 1991 and Cunningham and Wells, *J. Mol. Biol.* 234:554–63, 1993. A receptor, antibody, member or fragment is covalently attached, using amine or sulfhydryl chemistry, to dextran fibers that are attached to gold film within the flow cell. A test sample is passed through the cell. If a ligand, epitope, or opposite member of the complementary/anti-complementary pair is present in the sample, it will bind to the immobilized ligand, antibody or member, respectively, causing a change in the refractive index of the medium, which is detected as a change in surface plasmon resonance of the gold film. This system allows the determination of on- and off-rates, from which binding affinity can be calculated, and assessment of.

Ligand binding receptor polypeptides can also be used within other assay systems known in the art. Such systems include Scatchard analysis for determination of binding affinity (see Scatchard, *Ann. NY Acad. Sci.* 51: 660–72, 1949) and calorimetric assays (Cunningham et al., *Science* 253:545–48, 1991; Cunningham et al., *Science* 245:821–25, 1991).

A "soluble protein" is a protein that is not bound to a cell membrane. Soluble proteins are most commonly ligand-binding receptor polypeptides that lack transmembrane and cytoplasmic domains. Soluble proteins can comprise additional amino acid residues, such as affinity tags that provide for purification of the polypeptide or provide sites for attachment of the polypeptide to a substrate, or immunoglobulin constant region sequences. Many cell-surface proteins have naturally occurring, soluble counterparts that are produced by proteolysis or translated from alternatively spliced mRNAs. Proteins are said to be substantially free of transmembrane and intracellular polypeptide segments when they lack sufficient portions of these segments to provide membrane anchoring or signal transduction, respectively. The sequence as shown in SEQ ID NO:38 from residue 1 to residue 173 is a soluble protein. Fragments of the polypeptide as shown in SEQ ID NO:38 can also be used as a soluble protein. The partial cysteine-rich domain of SEQ ID NO:2, may be a complete domain in the polypeptide as shown in SEQ ID NO:38. Thus, this cyeteine-rich domain would be from residue 85 to residue 147, or from residue 85 to residue 163 as shown in SEQ ID NO:38. Additionally, there are two possible dibasic cleavage sites in SEQ ID NO:38 at residues 153–154, and residues 164–165. Thus, soluble fragments of ztnfr11 include the polypeptide from residue 1 to residue 147 fo SEQ ID NO:38; from residue 1 to 154 of SEQ ID NO:38; from residue 1 to residue 163 of SEQ ID NO:38; from residue 1 to 165 of SEQ ID NO:38; and from residue 1 to 173 of SEQ ID NO:38.

Soluble forms of UMLR polypeptides may act as antagonsits to or agonists of UMLR polypeptides, and would be useful to modulate the effects of UMLR in uterus, as well as in melanoma, osteosarcoma, breast carcinoma, and lymphoma, and in tumors of the lung. Thus, the isoform of UMLR that does not contain a transmembrane domain (i.e., the polypeptide of residues 1 to 129 of SEQ ID NO:2; residues 1 to 173 of SEQ ID NO:38; residues 1 to 147 of SEQ ID NO:38; residues 1 to 154 of SEQ ID NO:38; and residues 1 to 165 of SEQ ID NO:38;) will be soluble, and may act as an agonist or antagonist of UMLR activity. Since polypeptides of this nature are not anchored to the membrane, they can act at sites distant from the tissues in which they are expressed. Thus, the activity of the soluble form of UMLR polypeptides can be more wide spread than its membrane-anchored counterpart. Both isoforms would be useful in studying the effects of the present invention in vitro an in vivo.

Molecules of the present invention can be used to identify and isolate TNFs, or members of complement/anti-complement pairs involved in cell-cell interactions. For example, proteins and peptides of the present invention can be immobilized on a column and membrane preparations run over the column (*Immobilized Affinity Ligand Techniques*, Hermanson et al., eds., Academic Press, San Diego, Calif., 1992, pp. 195–202). Proteins and peptides can also be radiolabeled (*Methods in Enzymol.*, vol. 182, "Guide to Protein Purification", M. Deutscher, ed., Acad. Press, San Diego, 1990, 721–37) or photoaffinity labeled (Brunner et al., *Ann. Rev. Biochem.* 62:483–514, 1993 and Fedan et al., *Biochem. Pharmacol.* 33:1167–80, 1984) and specific cell-surface proteins can be identified.

The molecules of the present invention will be useful in modulating abnormal cell growth, inflammation, apoptosis, proliferation and differentiation. The polypeptides, nucleic acid and/or antibodies of the present invention can be used in treatment of disorders associated with infection, tumor growth, immunodeficiency, auto-immunity, and fertility. The molecules of the present invention can be used to modulate apoptosis, cell adhesion, cell fusion, and signaling or to treat or prevent development of pathological conditions in such diverse tissue as uterus, lung carcinoma, and breast carcinoma, as well as in cells of melanoma, osteosarcoma, and lymphoma. In particular, certain diseases may be amenable to such diagnosis, treatment or prevention. These diseases include, but are not limited to, melanoma, osteosarcoma, lung carcinoma, breast carcinoma, endometriosis, immunodeficiency, and infection of the genito-urinary tract. The molecules of the present invention can be used to modulate inhibition and proliferation of tissues in the uterus, lung carcinoma and breast carcinoma, as well as cells of melanoma, osteosarcoma, and lymphoma.

Polynucleotides encoding UMLR polypeptides are useful within gene therapy applications where it is desired to increase or inhibit UMLR activity. If a mammal has a mutated or absent UMLR gene, the UMLR gene can be introduced into the cells of the mammal. In one embodiment, a gene encoding a UMLR polypeptide is introduced in vivo in a viral vector. Such vectors include an attenuated or defective DNA virus, such as, but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes simplex virus 1 (HSV1) vector (Kaplitt et al., *Molec. Cell. Neurosci.* 2:320–30, 1991); an attenuated adenovirus vector, such as the vector described by Stratford-Perricaudet et al., *J. Clin. Invest.* 90:626–30, 1992; and a defective adeno-associated virus vector (Samulski et al., *J. Virol.* 61:3096–101, 1987; Samulski et al., *J. Virol.* 63:3822–8, 1989).

In another embodiment, a UMLR gene can be introduced in a retroviral vector, e.g., as described in Anderson et al., U.S. Pat. No. 5,399,346; Mann et al. *Cell* 33:153, 1983; Temin et al., U.S. Pat. No. 4,650,764; Temin et al., U.S. Pat. No. 4,980,289; Markowitz et al., *J. Virol.* 62:1120, 1988; Temin et al., U.S. Pat. No. 5,124,263; International Patent Publication No. WO 95/07358, published Mar. 16, 1995 by Dougherty et al.; and Kuo et al., *Blood* 82:845, 1993. Alternatively, the vector can be introduced by lipofection in vivo using liposomes. Synthetic cationic lipids can be used to prepare liposomes for in vivo transfection of a gene encoding a marker (Feigner et al., *Proc. Natl. Acad. Sci. USA* 84:7413–7, 1987; Mackey et al., *Proc. Natl. Acad. Sci. USA* 85:8027–31, 1988). The use of lipofection to introduce exogenous genes into specific organs in vivo has certain practical advantages. Molecular targeting of liposomes to specific cells represents one area of benefit. More particularly, directing transfection to particular cells represents one area of benefit. For instance, directing transfection to particular cell types would be particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

Similarly, the UMLR polynucleotides (SEQ ID NOs:1, 32, 33, and 36) can be used to target specific tissues such as tissues of the uterus, lung carcinoma and breast carcinoma, as well as in cells of melanoma, osteosarcoma, and lymphoma. It is possible to remove the target cells from the body; to introduce the vector as a naked DNA plasmid; and then to re-implant the transformed cells into the body. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., *J. Biol. Chem.* 267:963–7, 1992; Wu et al., *J. Biol. Chem.* 263:14621–4, 1988.

Various techniques, including antisense and ribozyme methodologies, can be used to inhibit UMLR gene transcription and translation, such as to inhibit cell proliferation in vivo. Polynucleotides that are complementary to a segment of a UMLR-encoding polynucleotide (e.g., a polynucleotide as set forth in SEQ ID NOs:1 or 3) are designed to bind to UMLR-encoding mRNA and to inhibit translation of such mRNA. Such antisense polynucleotides are used to inhibit expression of UMLR polypeptide-encoding genes in cell culture or in a subject.

Mice engineered to express the UMLR gene, referred to as "transgenic mice," and mice that exhibit a complete absence of UMLR gene function, referred to as "knockout mice," may also be generated (Snouwaert et al., *Science* 257:1083, 1992), may also be generated (Lowell et al., *Nature* 366:740–42, 1993; Capecchi, M. R., Science 244: 1288–1292, 1989; Palmiter, R. D. et al. *Annu Rev Genet.* 20: 465–499, 1986). For example, transgenic mice that overexpress UMLR, either ubiquitously or under a tissue-specific or tissue-restricted promoter can be used to ask whether over-expression causes a phenotype. For example, overexpression of a wild-type UMLR polypeptide, polypeptide fragment or a mutant thereof may alter normal cellular processes, resulting in a phenotype that identifies a tissue in which UMLR expression is functionally relevant and may indicate a therapeutic target for the UMLR, its agonists or antagonists. For example, a transgenic mouse to engineer is one that over-expresses the soluble UMLR polypeptide (approximately amino acids 1 to 129 of SEQ ID NO:2; amino acids 1 to 173 of SEQ ID NO:38; amino acids 1 to 147 of SEQ ID NO:38; amino acids 1 to 154 of SEQ ID NO:38; and amino acids 1 to 165 of SEQ ID NO:38;), or the membrane-bound receptor, (residues 1 to 269 of SEQ ID NO:2; residues 1 to 297 of SEQ ID NO:27; and residues 1 to 299 of SEQ ID NO:35). Moreover, such over-expression may result in a phenotype that shows similarity with human diseases. Similarly, knockout UMLR mice can be used to determine where UMLR is absolutely required in vivo. The phenotype of knockout mice is predictive of the in vivo effects of that a UMLR antagonist, such as those described herein, may have. The human UMLR cDNA can be used to isolate murine UMLR mRNA, cDNA and genomic DNA, which are subsequently used to generate knockout mice. These mice may be employed to study the UMLR gene and the protein encoded thereby in an in vivo system, and can be used as in vivo models for corresponding human diseases. Moreover, transgenic mice expression of UMLR antisense polynucleotides or ribozymes directed against UMLR, described herein, can be used analogously to transgenic mice described above.

Another use for in vivo models includes delivery of an antigen challenge to the animal followed by administration of soluble ztnfr11 or its ligand, and measuring the T cell response, or the proliferation or decline of ztnfr11-expressing cells.

T-cell dependent and T-cell independent immune response can be measured as described in Perez-Melgosa et al., *J. Immunol.* 163: 1123–7, 1999.

Pharmacokinetic studies can be used in association with radiolabeled, soluble ztnfr11 polypeptides or fusions to determine the distribution and half life of such polypeptides in vivo. Additionally animal models can be used to determine the effects of soluble ztnfr11 on tumors and tumor development in vivo.

Also provided is the use of ztnfr11 polypeptides as surrogate markers for abnormal cell growth, especially, such growth as related to melanoma, breast carcinoma, lung carcinoma, and cutaneous T-cell lymphoma. Patients having such diseases can be bleed and ztnfr11 soluble receptors and its ligand(s) can be detected in the blood.

UMLR polypeptides, variants, and fragments thereof, may be useful as replacement therapy for disorders associated with cell-cell interactions, including disorders related to, for example, immunology, fertility, egg maturation, and epithelial disorders, in general.

A less widely appreciated determinant of tissue morphogenesis is the process of cell rearrangement: Both cell motility and cell-cell adhesion are likely to play central roles in morphogenetic cell rearrangements. Cells need to be able to rapidly break and probably simultaneously remake contacts with neighboring cells. See Gumbiner, B. M., *Cell* 69:385–387, 1992. As a secreted protein in tissues of the uterus, lung carcinoma and breast carcinoma, as well as in cells of melanoma, osteosarcoma, and lymphoma. UMLR can play a role in intercellular rearrangement in these and other tissues.

UMLR gene may be useful to as a probe to identify humans who have a defective UMLR gene. The strong expression of UMLR in tissues of the uterus, lung carcinoma and breast carcinoma, as well as in cells of melanoma, osteosarcoma, and lymphoma suggests that UMLR polynucleotides or polypeptides can be used as measured as an indication of aberrant growth in these tissues. Thus, polynucleotides and polypeptides of UMLR, and mutations to them, can be used a diagnostic indicators of cancer in these tissues.

The polypeptides of the present invention are useful in studying cell adhesion and the role thereof in metastasis and may be useful in preventing metastasis, in particular metastasis in tumors of the uterus, lung, and in melanoma, osteosarcoma, breast carcinoma, and lymphoma. Similarly, polynucleotides and polypeptides of UMLR may be used to replace their detective counterparts in tumor or malignant tissues.

The UMLR polypeptide is expressed in tissues of the uterus, lung carcinoma and breast carcinoma as well as in cells of melanoma, osteosarcoma, and lymphoma. Thus, UMLR polypeptide pharmaceutical compositions of the present invention may be useful in prevention or treatment of disorders associated with pathological regulation or the expansion of these tissues.

The polynucleotides of the present invention may also be used in conjunction with a regulatable promoter, thus allowing the dosage of delivered protein to be regulated.

Moreover, the activity and effect of ztnfr11 on tumor progression and metastasis can be measured in vivo. Several syngeneic mouse models have been developed to study the influence of polypeptides, compounds or other treatments on tumor progression. In these models, tumor cells passaged in culture are implanted into mice of the same strain as the tumor donor. The cells will develop into tumors having similar characteristics in the recipient mice, and metastasis will also occur in some of the models. Tumor models include the Lewis lung carcinoma (ATCC No. CRL-1642) and B16 melanoma (ATCC No. CRL-6323), amongst others. These are both commonly used tumor lines, syngeneic to the C57BL6 mouse, that are readily cultured and manipulated in vitro. Tumors resulting from implantation of either of these cell lines are capable of metastasis to the lung in C57BL6 mice. The Lewis lung carcinoma model has recently been used in mice to identify an inhibitor of angiogenesis (O'Reilly MS, et al. *Cell* 79: 315–328, 1994). C57BL6/J mice are treated with an experimental agent either through daily injection of recombinant protein, agonist or antagonist or a one time injection of recombinant adenovirus. Three days following this treatment, $10^5$ to $10^6$ cells are implanted under the dorsal skin. Alternatively, the cells themselves may be infected with recombinant adenovirus, such as one expressing ztnfr11, before implantation so that the protein is synthesized at the tumor site or intracellularly, rather than systemically. The mice normally develop visible tumors within 5 days. The tumors are allowed to grow for a period of up to 3 weeks, during which time they may reach a size of 1500–1800 $mm^3$ in the control treated group. Tumor size and body weight are carefully monitored throughout the experiment. At the time of sacrifice, the tumor is removed and weighed along with the lungs and the liver. The lung weight has been shown to correlate well with metastatic tumor burden. As an additional measure, lung surface metastases are counted. The resected tumor, lungs and liver are prepared for histopathological examination, immunohistochemistry, and in situ hybridization, using methods known in the art and described herein. The influence of the expressed polypeptide in question, e.g., ztnfr11, on the ability of the tumor to recruit vasculature and undergo metastasis can thus be assessed. In addition, aside from using adenovirus, the implanted cells can be transiently transfected with ztnfr11. Moreover, purified ztnfr11 or ztnfr11-conditioned media can be directly injected in to this mouse model, and hence be used in this system. Use of stable ztnfr11 transfectants as well as use of induceable promoters to activate ztnfr11 expression in vivo are known in the art and can be used in this system to assess ztnfr11 induction of metastasis. For general reference see, O'Reilly M S, et al. *Cell* 79:315–328, 1994; and Rusciano D, et al. Murine Models of Liver Metastasis. *Invasion Metastasis* 14:349–361, 1995.

Ztnfr11 polypeptides and antibodies may be used within diagnostic systems to detect the presence of its ligand polypeptides, such as a tumor necrosis factor ligand. The information derived from such detection methods would provide insight into the significance of ztnfr11 polypeptides in various diseases, and as a would serve as diagnostic tools for diseases for which altered levels of ztnfr11 are significant. Altered levels of ztnfr11 polypeptides may be indicative of pathological conditions including cancer, autoimmune disorders and infectious diseases.

In a basic assay, a single-stranded probe molecule is incubated with RNA, isolated from a biological sample, under conditions of temperature and ionic strength that promote base pairing between the probe and target ztnfr11 species. After separating unbound probe from hybridized molecules, the amount of hybrids is detected.

Well-established hybridization methods of RNA detection include northern analysis and dot/slot blot hybridization (see, for example, Ausubel ibid. and Wu et al. (eds.), "Analysis of Gene Expression at the RNA Level," in *Methods in Gene Biotechnology*, pages 225–239 (CRC Press, Inc. 1997)). Nucleic acid probes can be detectably labeled with radioisotopes such as $^{32}$P or $^{35}$S. Alternatively, ztnfr11 RNA can be detected with a nonradioactive hybridization method (see, for example, Isaac (ed.)., *Protocols for Nucleic Acid Analysis by Nonradioactive Probes*, Humana Press, Inc., 1993). Typically, nonradioactive detection is achieved by enzymatic conversion of chromogenic or chemiluminescent substrates. Illustrative nonradioactive moieties include biotin, fluorescein, and digoxigenin.

ztnfr11 oligonucleotide probes are also useful for in vivo diagnosis. As an illustration, $^{18}$F-labeled oligonucleotides can be administered to a subject and visualized by positron emission tomography (Tavitian et al., *Nature Medicine* 4:467, 1998).

Numerous diagnostic procedures take advantage of the polymerase chain reaction (PCR) to increase sensitivity of detection methods. Standard techniques for performing PCR are well-known (see, generally, Mathew (ed.), *Protocols in Human Molecular Genetics* (Humana Press, Inc. 1991), White (ed.), *PCR Protocols: Current Methods and Applications* (Humana Press, Inc. 1993), Cotter (ed.), *Molecular Diagnosis of Cancer* (Humana Press, Inc. 1996), Hanausek and Walaszek (eds.), *Tumor Marker Protocols* (Humana Press, Inc. 1998), Lo (ed.), *Clinical Applications of PCR* (Humana Press, Inc. 1998), and Meltzer (ed.), *PCR in Bioanalysis* (Humana Press, Inc. 1998)). PCR primers can be designed to amplify a sequence encoding a particular ztnfr11 domain or motif, such as the ztnfr11 cysteine rich pseudo repeat.

One variation of PCR for diagnostic assays is reverse transcriptase-PCR (RT-PCR). In the RT-PCR technique, RNA is isolated from a biological sample, reverse transcribed to cDNA, and the cDNA is incubated with ztnfr11 primers (see, for example, Wu et al. (eds.), "Rapid Isolation of Specific cDNAs or Genes by PCR," in *Methods in Gene Biotechnology*, CRC Press, Inc., pages 15–28, 1997). PCR is then performed and the products are analyzed using standard techniques.

As an illustration, RNA is isolated from biological sample using, for example, the guanidinium-thiocyanate cell lysis procedure described above. Alternatively, a solid-phase technique can be used to isolate mRNA from a cell lysate. A reverse transcription reaction can be primed with the isolated RNA using random oligonucleotides, short homopolymers of dT, or ztnfr11 anti-sense oligomers. Oligo-dT primers offer the advantage that various mRNA nucleotide sequences are amplified that can provide control target sequences. Ztnfr11 sequences are amplified by the polymerase chain reaction using two flanking oligonucleotide primers that are typically at least 5 bases in length.

PCR amplification products can be detected using a variety of approaches. For example, PCR products can be fractionated by gel electrophoresis, and visualized by ethidium bromide staining. Alternatively, fractionated PCR products can be transferred to a membrane, hybridized with a detectably-labeled ztnfr11 probe, and examined by autoradiography. Additional alternative approaches include the use of digoxigenin-labeled deoxyribonucleic acid triphosphates to provide chemiluminescence detection, and the C-TRAK colorimetric assay.

Another approach is real time quantitative PCR (Perkin-Elmer Cetus, Norwalk, Conn.). A fluorogenic probe, consisting of an oligonucleotide with both a reporter and a quencher dye attached, anneals specifically between the forward and reverse primers. Using the 5' endonuclease activity of Taq DNA polymerase, the reporter dye is separated from the quencher dye and a sequence-specific signal is generated and increases as amplification increases. The fluorescence intensity can be continuously monitored and quantified during the PCR reaction.

Another approach for detection of ztnfr11 expression is cycling probe technology (CPT), in which a single-stranded DNA target binds with an excess of DNA-RNA-DNA chimeric probe to form a complex, the RNA portion is cleaved with RNase H, and the presence of cleaved chimeric probe is detected (see, for example, Beggs et al., *J. Clin. Microbiol.* 34:2985, 1996 and Bekkaoui et al., *Biotechniques* 20:240, 1996). Alternative methods for detection of ztnfr11 sequences can utilize approaches such as nucleic acid sequence-based amplification (NASBA), cooperative amplification of templates by cross-hybridization (CATCH), and the ligase chain reaction (LCR) (see, for example, Marshall et al., U.S. Pat. No. 5,686,272 (1997), Dyer et al., *J. Virol. Methods* 60:161, 1996; Ehricht et al., *Eur. J. Biochem.* 243:358, 1997 and Chadwick et al., *J. Virol. Methods* 70:59, 1998). Other standard methods are known to those of skill in the art.

Ztnfr11 probes and primers can also be used to detect and to localize ztnfr11 gene expression in tissue samples. Methods for such in situ hybridization are well-known to those of skill in the art (see, for example, Choo (ed.), *In Situ Hybridization Protocols*, Humana Press, Inc., 1994; Wu et al. (eds.), "Analysis of Cellular DNA or Abundance of mRNA by Radioactive In Situ Hybridization (RISH)," in *Methods in Gene Biotechnology*, CRC Press, Inc., pages 259–278, 1997 and Wu et al. (eds.), "Localization of DNA or Abundance of mRNA by Fluorescence In Situ Hybridization (RISH)," in *Methods in Gene Biotechnology*, CRC Press, Inc., pages 279–289, 1997).

Various additional diagnostic approaches are well-known to those of skill in the art (see, for example, Mathew (ed.), *Protocols in Human Molecular Genetics* Humana Press, Inc., 1991; Coleman and Tsongalis, *Molecular Diagnostics*, Humana Press, Inc., 1996 and Elles, *Molecular Diagnosis of Genetic Diseases*, Humana Press, Inc., 1996).

In addition, such polynucleotide probes could be used to hybridize to counterpart sequences on individual chromosomes. Chromosomal identification and/or mapping of the ztnfr11 gene could provide useful information about gene function and disease association. Many mapping techniques are available to one skilled in the art, for example, mapping somatic cell hybrids, and fluorescence in situ hybridization (FISH). A preferred method is radiation hybrid mapping. Radiation hybrid mapping is a somatic cell genetic technique developed for constructing high-resolution, contiguous maps of mammalian chromosomes (Cox et al., *Science* 250:245–50, 1990). Partial or full knowledge of a gene's sequence allows the designing of PCR primers suitable for use with chromosomal radiation hybrid mapping panels. Commercially available radiation hybrid mapping panels which cover the entire human genome, such as the Stanford G3 RH Panel and the GeneBridge 4 RH Panel (Research Genetics, Inc., Huntsville, Ala.), are available. These panels enable rapid, PCR based, chromosomal localizations and ordering of genes, sequence-tagged sites (STSs), and other non-polymorphic- and polymorphic markers within a region of interest. This includes establishing directly proportional physical distances between newly discovered genes of interest and previously mapped markers. The precise knowledge of a gene's position can be useful in a number of ways including: 1) determining if a sequence is part of an existing contig and obtaining additional surrounding genetic sequences in various forms such as YAC-, BAC- or cDNA clones, 2) providing a possible candidate gene for an inheritable disease which shows linkage to the same chromosomal region, and 3) for cross-referencing model organisms such as mouse which may be beneficial in helping to determine what function a particular gene might have.

The UMLR polynucleotides of SEQ ID NO:2 have been mapped to chromosome Xq11–q12. Thus, the present invention also provides reagents which will find use in diagnostic applications. For example, the UMLR gene, a probe comprising UMLR DNA or RNA or a subsequence thereof can be used to determine if the UMLR gene is present on chromosome Xq11–q12 or if a mutation has occurred. Detectable chromosomal aberrations at the UMLR gene locus include, but are not limited to, aneuploidy, gene copy number changes, insertions, deletions, restriction site changes and rearrangements. These aberrations can occur within the coding sequence, within introns, or within flanking sequences, including upstream promoter and regulatory regions, and may be manifested as physical alterations within a coding sequence or changes in gene expression level.

Such aberrations can be detected using polynucleotides of the present invention by employing molecular genetic techniques, such as restriction fragment length polymorphism (RFLP) analysis, short tandem repeat (STR) analysis employing PCR techniques, and other genetic linkage analysis techniques known in the art (Sambrook et al., ibid.; Ausubel et. al., ibid.; Marian, *Chest* 108:255–65, 1995).

In general, these diagnostic methods comprise the steps of (a) obtaining a genetic sample from a patient; (b) incubating the genetic sample with a polynucleotide probe or primer as disclosed above, under conditions wherein the polynucleotide will hybridize to complementary polynucleotide sequence, to produce a first reaction product; and (iii) comparing the first reaction product to a control reaction product. A difference between the first reaction product and the control reaction product is indicative of a genetic abnormality in the patient. Genetic samples for use within the present invention include genomic DNA, cDNA, and RNA. The polynucleotide probe or primer can be RNA or DNA, and will comprise a portion of SEQ ID NOs:1 or 3, the complement of SEQ ID NOs:1 or 3, or an RNA equivalent thereof. Suitable assay methods in this regard include molecular genetic techniques known to those in the art, such as restriction fragment length polymorphism (RFLP) analysis, short tandem repeat (STR) analysis employing PCR techniques, ligation chain reaction (Barany, *PCR Methods and Applications* 1:5–16, 1991), ribonuclease protection assays, and other genetic linkage analysis techniques known in the art (Sambrook et al., ibid.; Ausubel et. al., ibid.; Marian, *Chest* 108:255–65, 1995). Ribonuclease protection assays (see, e.g., Ausubel et al., ibid., ch. 4) comprise the hybridization of an RNA probe to a patient RNA sample, after which the reaction product (RNA-RNA hybrid) is exposed to RNase. Hybridized regions of the RNA are protected from digestion. Within PCR assays, a patient's genetic sample is incubated with a pair of polynucleotide primers, and the region between the primers is amplified and recovered. Changes in size or amount of recovered product are indicative of mutations in the patient. Another PCR-based technique that can be employed is single strand conformational polymorphism (SSCP) analysis (Hayashi, *PCR Methods and Applications* 1:34–8, 1991).

Antisense methodology can be used to inhibit ztnfr11 gene transcription, such as to inhibit T cell development and interaction with other cells. Polynucleotides that are complementary to a segment of a ztnfr11-encoding polynucleotide (e.g., a polynucleotide as set forth in SEQ ID NOs:2, 27, or 38) are designed to bind to ztnfr11-encoding mRNA and to inhibit translation of such mRNA. Such antisense polynucleotides are used to inhibit expression of ztnfr11 polypeptide-encoding genes in cell culture or in a subject.

Additionally, polynucleotides of the present invention can be used as a marker for the X chromosome. Diseases which map to the Xq11–12 include, but are not limited to, adenocarcinoma of the prostate (Verma, R. S. et al., *Cancer Invest.* 17(6):441–447, 1999); and dystonia-parkinsonism, sideroblastic anemia, and several forms of mental retardation (Villard, L. et al., *Gene* 235(1–2):43–50, 1999). Other aberrations at this locus include a deletion which is related to borderline and invasive epithelial tumors (Edelson, M. L. et al., *Oncogene* 16(2):192–202, 1998), and a gain in patients with adult testicular germ cell tumors (Summersgill, B. et al., *Br J Cancer* 77(2):305–13, 1998).

The polypeptides of UMLR may represent an antigenic marker for melanoma, osteosarcoma, breast carcinoma, and lymphoma, as well as tumors of the lung and uterus. Thus, these polypeptides, or fragments thereof may be useful as antigens to produce humanized antibodies for treatment of these specific tumors. Additionally, these polypeptides and polypeptide fragments can be useful to generate vaccines for use cancer therapy.

For pharmaceutical use, the proteins of the present invention can be administered intravaginally, orally, rectally, parenterally (particularly intravenous or subcutaneous), intracisternally, intraperitoneally, topically (as douches, powders, ointments, drops or transdermal patch) bucally, or as a pulmonary or nasal inhalant. Intravenous administration will be by bolus injection or infusion over a typical period of one to several hours. In general, pharmaceutical formulations will include a UMLR protein, alone, or in conjunction with a dimeric partner, in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in Remington: *The Science and Practice of Pharmacy*, Gennaro, ed., Mack Publishing Co., Easton, Pa., 19th ed., 1995. Therapeutic doses will generally be in the range of 0.1 to 100 µg/kg of patient weight per day, preferably 0.5–20 mg/kg per day, with the exact dose determined by the clinician according to accepted standards, taking into account the nature and severity of the condition to be treated, patient traits, etc. Determination of dose is within the level of ordinary skill in the art. The proteins may be administered for acute treatment, over one week or less, often over a period of one to three days or may be used in chronic treatment, over several months or years. In general, a therapeutically effective amount of UMLR is an amount sufficient to produce a clinically significant change in, tumor suppression, apoptosis, myogenesis, inflammation, and infection in tissues of the uterus, lung carcinoma and breast carcinoma, as well as in cells of melanoma, osteosarcoma, and lymphoma. Similarly, a therapeutically effective amount of UMLR is an amount sufficient to produce a clinically significant change in disorders associated with tissues of the uterus, melanoma, osteosarcoma, breast carcinoma, and lymphoma, and tumors of the lung.

The invention is further illustrated by the following non-limiting examples.

EXAMPLES

Example 1

Extension of EST Sequence

The novel UMLR polypeptide-encoding polynucleotides of the present invention were initially identified by querying a database of partial sequences. A partial sequence was identified in a uterus, myometruim, leiomyoma cDNA library. The polynucleotide sequence (SEQ ID NO:1) of the insert corresponding to the cDNA clone was sequenced. The deduced amino acid sequence of the insert was determined to be full-length and is shown in SEQ ID NO:2. This polypeptide, and the polynucleotides encoding it, were identified as a novel member of the tumor necrosis factor receptor family, UMLR.

Example 2

Tissue Distribution

Human Multiple Tissue Northern Blots (MTN I, MTN II and MTN III; Human Cancer Cell Line; Human Immune Blot; Clontech, In-house human lymphocyte subset blot; Clontech, Palo Alto, Calif.) were probed to determine the tissue distribution of human UMLR expression. An approximately 555 bp PCR derived probe was amplified as a template and oligonucleotide ZC25364 (SEQ ID NO:12) and oligonucleotide ZC25365 (SEQ ID NO:13) as primers. The amplification was carried out as follows: 1 cycle at 94° C. for 1.5 minutes, 35 cycles of 94° C. for 15 seconds and 60° C. for 30 seconds, followed by one cycle at 72° C. for 10 minutes. The PCR products were visualized by agarose gel electrophoresis and the 555 bp PCR product was purified using a Gel Extraction Kit (Qiagen, Chatsworth, Calif.) according to manufacturer's instructions. The probe was radioactively labeled using the MULTIPRIME DNA labeling kit (Amersham, Arlington Heights, Ill.) according to the manufacturer's instructions. The probe was purified using a NUCTRAP push column (Stratagene). EXPRESSHYB (Clontech) solution was used for prehybridization and as a hybridizing solution for the Northern blots. Hybridization took place overnight at 65° C. using 1×10$^6$ cpm/ml of labeled probe. The blots were then washed four times in 2×SSC and 0.1% SDS at RT, followed by 2 washes in 0.1×SSC and 0.1% SDS at 55° C. A major transcript of approximately 3.5 kb and a minor transcript of ~4.7 kb were seen in the lung carcinoma cell line A-549 and the melanoma cell line G-361. All other samples were negative at a 24 hr exposure time.

Example 3

Chromosomal Assignment and Placement of UMLR

UMLR was mapped to human chromosome X using the commercially available version of the "Stanford G3 Radiation Hybrid Mapping Panel" (Research Genetics, Inc., Huntsville, Ala.). The "Stanford G3 RH Panel" contains PCRable DNAs from each of 83 radiation hybrid clones of the whole human genome, plus two control DNAs (the RM donor and the A3 recipient). A publicly available WWW server (http://shgc-www.stanford.edu) allows chromosomal localization of markers.

For the mapping of UMLR with the "Stanford G3 RH Panel", 20 µl reactions were set up in a 96-well microtiter plate (Stratagene, La Jolla, Calif.) and used in a "RoboCycler Gradient 96" thermal cycler (Stratagene). Each of the 85 PCR reactions consisted of 2 µl 10× KlenTaq PCR reaction buffer (CLONTECH Laboratories, Inc., Palo Alto, Calif.), 1.6 µl dNTPs mix (2.5 mM each, PERKIN-ELMER, Foster City, Calif.), 1 µl sense primer, ZC 25352 (SEQ ID NO:14), 1 µl antisense primer, ZC 25353 (SEQ ID NO:15), 2 µl "RediLoad" (Research Genetics, Inc., Huntsville, Ala.), 0.4 µl 50× Advantage KlenTaq Polymerase Mix (Clontech Laboratories, Inc.), 25 ng of DNA from an individual hybrid clone or control and x µl ddH2O for a total volume of 20 µl. The reactions were overlaid with an equal amount of mineral oil and sealed. The PCR cycler conditions were as follows: an initial 1 cycle 5 minute denaturation at 94° C., 35 cycles of a 45 seconds denaturation at 94° C., 45 seconds annealing at 64° C. and 1 minute AND 15 seconds extension at 72° C., followed by a final 1 cycle extension of 7 minutes at 72° C. The reactions were separated by electrophoresis on a 2% agarose gel.

The results showed linkage of UMLR to the human chromosome X framework marker SHGC-1486 with a LOD score of 7.00 and at a distance of 22 cR__10000 from the marker. The use of surrounding genes/markers positions UMLR in the Xq11–q12 chromosomal region.

Example 4

Construction of Mammalian Soluble ztnfr11 Expression Vectors: ztnfr11sR/CEE and Ztnfr11sR/Fc4

An expression vector was prepared to express the soluble ztnfr11 polypeptide (ztnfr11sR, i.e., from residue 2 to residue 132 of SEQ ID NO:2) fused to a C-terminal Glu-Glu tag (SEQ ID NO:16).

A PCR generated ztnfr11 DNA fragment of about 400 bp was created using oligo ZC25598 (SEQ ID NO:17) and oligo ZC25596 (SEQ ID NO:18) as PCR primers to add BamHI and BglII restriction sites at 5' and 3' ends of the soluble ztnfr11 DNA, respectively. A plasmid containing the ztnfr11 cDNA (SEQ ID NO:1) was used as a template. PCR amplification of the ztnfr11 fragment was performed as follows: One cycle at 94° C. for 1 minute; 25 cycles at 94° C. for 30 seconds, 68° C. for 90 seconds, followed by an additional 68° C. incubation for 4 minutes, and hold at 10° C. The reaction was purified by chloroform/phenol extraction and isopropanol precipitation, and digested with BamHI and Bgl2 (Boehringer Mannheim, Indianapolis, Ind.). A band of approximately 400 bp, as visualized by 1% agarose gel electrophoresis, was excised and the DNA was purified using a QiaexII™ purification kit (Qiagen, Valencia, Calif.) according to the manufacturer's instruction.

The pZP9CEE plasmid is a mammalian expression vector containing an expression cassette having the mouse metallothionein-1 promoter, human tPA leader peptide, multiple restriction sites for insertion of coding sequences, a Glu-Glu tag, and a human growth hormone terminator. The plasmid also has an E. coli origin of replication, a mammalian selectable marker expression unit having an SV40 promoter, an enhancer and an origin of replication, as well as a DHFR gene, and the SV40 terminator. The ztnfr11sR/pZP9/CEE expression vector uses the human tPA leader peptide (SEQ ID NO:19) and attaches the Glu-Glu tag to the C-terminus of the extracellular portion of the ztnfr11 polypeptide sequence.

About 30 ng of the restriction digested ztnfr11sR insert and about 10 ng of the digested vector were ligated at room temperature for 2 hours. One microliter of ligation reaction was electroporated into DH10B competent cells (Gibco BRL, Rockville, Md.) according to manufacturer's direction and plated onto LB plates containing 50 mg/ml ampicillin, and incubated overnight. Colonies were screened by restriction analysis of DNA, which was prepared from 2 ml liquid cultures of individual colonies. The insert sequence of positive clones was verified by sequence analysis. The sequence of the soluble ztnfr11 gene fused amino-terminally to the human tPA leader and carboxy-terminally to the CEE tag is shown in SEQ ID NO:21. Thus the excised ztnfr11sR DNA was subcloned into the pZP9CEE plasmid, which had been cut with BamHI. The A large-scale plasmid preparation was done using a Qiagen® Mega prep kit (Qiagen) according to manufacturer's instruction.

The same process was used to prepare the ztnfr11 soluble receptor with a C-terminal Fc4 tag (SEQ ID NO:20), creating the ztnfr11sR/Fc4. To prepare ztnfr11sR/Fc4, the pZP9 vector has a Fc4 tag in place of the Glu-Glu tag. The sequence of the soluble ztnfr11 gene fused amino-terminally to the human tPA leader and carboxy-terminally to the Fc4 tag is shown in SEQ ID NO:22. Fc4 is the Fc region derived from human IgG, which contains a mutation so that it no longer binds the Fc receptor.

Example 5

Transfection and Expression of Ztnfr11 Soluble Receptor Polypeptides

The day before the transfection, BHK 570 cells (ATCC No. CRL-10314; ATCC, Manasas, Va.) were plated in a 10-cm plate with 50% confluence in normal BHK DMEM (Gibco/BRL High Glucose) media. The day of the transfection, the cells were washed once with Serum Free (SF) DMEM, followed by transfection with the ztnfr11sR/Fc4 or ztnfr11sR/CEE expression plasmids. Sixteen micrograms of each DNA construct were separately diluted into a total final volume of 640 µl SF DMEM. A diluted LipofectAMINE™ mixture (35 µl LipofectAMINE™ in 605 µl SF meida) was added to the DNA mix, and incubated for 30 minutes at room temperature. Five milliliters of SF media was added to the DNA/LipofectAMINE™ mixture, which was then added to BHK cells. The cells were incubated at 37° C./5% $CO_2$ for 5 hours, after which 6.4 ml of BHK media with 10% FBS was added. The cells were incubated overnight at 37° C./5% $CO_2$.

Approximately 24 hours post-transfection, the BHK cells were split into selection media with 1 µM methotrexate (MTX). The cells were repeatedly split in this manner until stable ztnfr11sR/CEE and ztnfr11sRIFc4 cell lines were identified. To detect the expression level of the ztnfr11 soluble receptor fusion proteins, the BHK cells were washed with PBS and incubated in SF media for 72 hours. The SF condition media was collected and 20 µl of the sample was run on 10% SDS-PAGE gel under reduced conditions. The protein bands were transferred to nitrocellulose filter by Western blot, and the fusion proteins were detected using either goat-anti-human IgG/HRP conjugates for the ztnfr11sR/Fc4 fusion or mouse-anti-Glu-Glu tag/HRP conjugates for the ztnfr11sR/CEE fusion. Expression vectors containing a different soluble receptor fused to the Fc4 or the CEE tags were used as controls. The expression level is approximately 10 mg/L for ztnfr11sR/Fc4 and 0.5 mg/L for ztnfr11sR/CEE.

Transfected BHK cells were transferred into T-162 flasks. Once the BHK cells reached about 80% confluence, they were washed with PBS and incubated in 100 ml SF media for 72 hours, and then the condition media was collected for protein purification.

Example 6

Purification and Analysis of Ztnfr11sR/CEE

Recombinant carboxyl terminal Glu-Glu tagged ztnfr11sR was produced from transfected BHK cells as described in Example 5 above. About six liters of conditioned media were harvested from 60 dishes after roughly 72 hours incubation. A portion of the media was sterile filtered using filtration units from different manufactures. The Nalgene 0.2 µm and 0.45 µm filters, and Millipore Express 0.22 µm filter were compared. The amount of ztnfr11sR/CEE lost through the filter can be more than 50% of the starting material with Nalgene's 0.2 µm filter. The other filters performed better and gave more reasonable recovery of the protein. Additionally, the Millipore Express 0.22 µm filter achieved a good flow rate. The level of protein expression reached the optimal concentration after about 72 hours in new media. Three harvests of the ztnfr11sR/CEE conditioned media were collected.

Protein was purified from the filtered media by a combination of Anti-Glu-Glu (Anti-EE) peptide antibody affinity chromatography and S-100 gel exclusion chromatography. Culture medium was directly loaded onto a 20×85 mm (58-ml bed volume) anti-EE antibody affinity column at a flow of about 4 ml/minute. Following column washing with ten column volumes of PBS, bound protein was eluted with two column volumes of 0.4 mg/ml EYMPTD peptide (Princeton Biomolecules, N.J.). Fractions of 5 ml were collected. Samples from the anti-EE antibody affinity column were analyzed by SDS-PAGE with silver staining and western blotting for the presence of ztnfr11sR/CEE. Fractions containing the ztnfr11sR/CEE protein were pooled and concentrated to 4 mils using Biomax-5 concentrator (Millipore), and loaded onto a 16×1000 mm Sephacryl S-100 HR gel filtration column (Amersham Pharmacia Biotech). The fractions containing purified ztnfr11sR/CEE were pooled, filtered through 0.2 µm filter, aliquoted into 100 µl each, and frozen at −80° C. The concentration of the final purified protein was determined by BCA assay (Pierce) and HPLC-amino acid analysis.

Recombinant ztnfr11sR/CEE was analyzed by SDS-PAGE (Nupage 4–12%), Novex) with either coomassie and silver staining method (Fast Silver, Geno Tech), and Western blotting using monoclonal anti-EE antibody. Either the conditioned media or purified protein was electrophoresed using a Novex's Xcell II mini-cell (San Diego, Calif.) and transferred to nitrocellulose (0.2 µm; Bio-Rad Laboratories, Hercules, Calif.) at room temperature using Novex's Xcell II blot module with stirring according to directions provided in the instrument manual. The transfer was run at 500 mA for one hour in a buffer containing 25 mM Tris base, 200 mM glycine, and 20% methanol. The filters were then blocked with 10% non-fat dry milk in PBS for 10 minutes at room temperature. The nitrocellulose was quickly rinsed, then primary antibody was added in PBS containing 2.5% non-fat dry milk. The blots were incubated for two hours at room temperature or overnight at 4° C. with gentle shaking. Following the incubation, blots were washed three times for 10 minutes each in PBS. Secondary antibody (goat anti-mouse IgG conjugated to horseradish peroxidase; obtained from Rockland Inc., Gilbertsville, Pa.) diluted 1:2000 in PBS containing 2.5% non-fat dry milk was added, and the blots were incubated for two hours at room temperature with gentle shaking. The blots were then washed three times, 10 minutes each, in PBS, then quickly rinsed in $H_2O$. The blots were developed using commercially available chemiluminescent substrate reagents (SuperSignal® ULTRA reagents 1 and 2 mixed 1:1; reagents obtained from Pierce Chemical Co.), and the signal was captured using Lumi-Imager's Lumi Analyst 3.0 software (Boehringer Mannheim GmbH, Germany) for exposure times ranging from 10 second to 5 minutes or as necessary.

The purified ztnfr11sR/CEE appeared as a single band with either the coomassie or silver staining at about 18 kDa under non-reducing conditions, and at about 20 kDa under reducing conditions, suggesting the monomeric form of ztnfr11sR/CEE under non-reducing conditions.

Example 7

Purification and Analysis of Ztnfr11sR/Fc4

Recombinant carboxyl terminal Fc4 tagged ztnfr11sR was produced from transfected BHK cells as described in Example 5 above. Approximately five-liters of conditioned media were harvested from 60 dishes after about 72 hours of incubation. A portion of the media was sterile filtered using filtration units from different manufactures. The Nalgene 0.2 μm and 0.45 μm filters, Millipore Express 0.22 μm filter, and Durapore 0.45 μm filter were compared. The Millipore Express 0.22 μm filter gave the best yield and flow rate. The level of protein expression reached the optimal concentration after about 72 hours in the new media. Normally three to four harvests of the media were collected.

Protein was purified from the filtered media by a combination of Poros 50 protein A affinity chromatography (PerSeptive Biosystems, 1-5559-01, Framingham, Mass.) and S-200 gel exclusion chromatography column (Amersham Pharmacia Biotech). Culture medium was directly loaded onto a 10×80 mm (6.2-ml bed volume) protein A affinity column at a flow of about 4 ml/minute. Following column washing for ten column volumes of PBS, bound protein was eluted by five column volumes of 0.1 M glycine, pH 3.0 at 10 ml/minute). Fractions of 1.5 ml each were collected into tubes containing 38 μl of 2.0 M Tris, pH 8.8, in order to neutralize the eluted proteins. Samples from the affinity column were analyzed by SDS-PAGE with Coomassie staining and Western blotting for the presence of ztnfr11sR/Fc4 using human IgG-HRP. Ztnfr11sR/Fc4-containing fractions were pooled and concentrated to 4 mls using Biomax-30 concentrator (Millipore), and loaded onto a 16×1000 mm Sephacryl S-200 HR gel filtration. The fractions containing purified ztnfr11sR/Fc4 were pooled, filtered through 0.2 μm filter, aliquoted into 100, 200 and 500 μl each, and frozen at −80° C. The concentration of the final purified protein was determined by BCA assay (Pierce) and HPLC-amino acid analysis.

Recombinant ztnfr11sR/Fc4 was analyzed by SDS-PAGE (Nupage 4–12%, Novex) with coomassie staining method and Western blotting using human IgG-HRP. Either the conditioned media or purified protein was electrophoresed using a Novex's Xcell II mini-cell (San Diego, Calif.) and transferred to nitrocellulose (0.2 μm; Bio-Rad Laboratories, Hercules, Calif.) at room temperature using Novex's Xcell II blot module with stirring according to directions provided in the instrument manual. The transfer was run at 500 mA for one hour in a buffer containing 25 mM Tris base, 200 mM glycine, and 20% methanol. The filters were then blocked with 10% non-fat dry milk in PBS for 10 minutes at room temperature. The nitrocellulose was quickly rinsed, then the human Ig-HRP antibody (1:2000) was added in PBS containing 2.5% non-fat dry milk. The blots were incubated for two hours at room temperature, or overnight at 4° C., with gentle shaking. Following the incubation, the blots were washed three times for 10 minutes each in PBS, then quickly rinsed in $H_2O$. The blots were developed using commercially available chemiluminescent substrate reagents (SuperSignal® ULTRA reagents 1 and 2 mixed 1:1; reagents obtained from Pierce Chemical Co.), and the signal was captured using Lumi-Imager's Lumi Analyst 3.0 software (Boehringer Mannheim GmbH, Germany) for exposure times ranging from 10 second to 5 minutes or as necessary.

The purified ztnfr11sR/Fc4 appeared as a single band with either the coomassie or silver staining at about 100 kDa under non-reducing conditions, and at about 55 kDa under reducing conditions, suggesting the dimeric form of ztnfr11sR/Fc4 under non-reducing conditions as expected.

Example 8

Identification of Cells Expressing Ztnfr11 Using In Situ Hybridization

Specific human tissues were isolated and screened for ztnfr11 expression by in situ hybridization. Various human tissues prepared, sectioned and subjected to in situ hybridization included normal lung, lung carcinoma and breast carcinoma. The tissues were fixed in 10% buffered formalin and blocked in paraffin using standard techniques. Tissues were sectioned at 4 to 8 microns. Tissues were prepared using a standard protocol ("Development of non-isotopic in situ hybridization" at http://dir.niehs.nih.gov/dirlep/ish.html). Briefly, tissue sections were deparaffinized with HistoClear (National Diagnostics, Atlanta, Ga.) and then dehydrated with ethanol. Next they were digested with Proteinase K (50 μg/ml) (Boehringer Diagnostics, Indianapolis, Ind.) at 37° C. for 2 to 20 minutes. This step was followed by acetylation and re-hydration of the tissues.

Two in situ probes generated by PCR were designed against the human ztnfr11 sequence. Two sets of oligos were designed to generate probes for separate regions of the ztnfr11 cDNA: (1) Oligos ZC26463 (SEQ ID NO:23) and ZC26464 (SEQ ID NO:24) were used to generate a 439 bp probe for ztnfr11 (from nucleotide 290 to nucleotide 840 as shown in SEQ ID NO:1); and (2) ZC26470 (SEQ ID NO: 25) and ZC26471 (SEQ ID NO: 26) were used to generate a 548 bp probe for ztnfr11 (from nucleotide 560 to nucleotide 1000 as shown in SEQ ID NO:1). The antisense oligo from each set also contained the working sequence for the T7 RNA polymerase promoter to allow for easy transcription of antisense RNA probes from these PCR products. The PCR reaction conditions were as follows: 2 cycles at 95° C. for 30 sec, 50° C. for 1 min, 72° C. for 1 min followed by 33 cycles of 95° C. for 30 sec, 72° C. for 2 min. Probes were subsequently labeled with digoxigenin (Boehringer) or biotin (Boehringer) using an In Vitro transcription System (Promega, Madison, Wis.) as per manufacturer's instruction.

In situ hybridization was performed with a digoxigenin- or biotin-labeled ztnfr11 probe (above). The probe was added to the slides at a concentration of 1 to 5 pmol/ml for 12 to 16 hours at 60° C. Slides were subsequently washed in 2×SSC and 0.1×SSC at 55° C. The signals were amplified using tyramide signal amplification (TSA) (TSA, in situ indirect kit; NEN) and visualized with Vector Red substrate kit (Vector Lab) as per manufacturer's instructions. The slides were then counter-stained with hematoxylin (Vector Laboratories, Burlingame, Calif.).

Positive signals were seen in the human lung carcinoma and one of two breast carcinoma tissue samples. The positive-staining cells in the human lung carcinoma sample appeared to be plasma cells, mononuclear cells of unknown type and occasional alveolar epithelial cells. In one of the breast carcinoma tissue samples the positive staining cells appeared to be epthilial/myoepithelial cells, clusters of tumor cells within vascular lumens, mononuclear cells and occasional vascular endothelial cells. The normal human lung tissue sample and one of the breast carcinoma tissue samples were negative for ztnfr11.

Example 9

Human ztnfr11 Polyclonal Antibodies

Polyclonal antibodies were prepared by immunizing 2 female New Zealand white rabbits with the purified recombinant protein ztnfr11-CEE protein expressed in BHK from Example 6. The rabbits were each given an initial intraperitoneal (ip) injection of 200 µg of purified protein in Complete Freund's Adjuvant followed by booster ip injections of 100 µg peptide in Incomplete Freund's Adjuvant every three weeks. Seven to ten days after the administration of the second booster injection (3 total injections), the animals were bled and the serum was collected. The animals were then boosted and bled every three weeks.

The ztnfr11sR-specific polyclonal antibodies were affinity purified from the rabbit serum using a CNBr-SEPHAROSE 4B protein column (Pharmacia LKB) that was prepared using 10 mg of purified recombinant huztnfr11-Fc protein (as prepared in Example 6) per gram of CNBr-SEPHAROSE, followed by 20x dialysis in PBS overnight. Ztnfr11sR-specific antibodies were characterized by ELISA using 1 µg/ml of the specific purified recombinant huztnfr11-CEE-BHK protein as antibody target. The lower limit of detection (LLD) of the rabbit anti-ztnfr11sR affinity purified antibody was 100 pg/ml on its specific purified recombinant protein antigen ztnfr11sR/CEE.

Example 10

Human ztnfr11 Skin Northern

A probe of approximately 555 bp was made by PCR using plasmid DNA containing SEQ ID NO:1 as a template and oligonucleotide ZC25364 (SEQ ID NO:12) and ZC25365 (SEQ ID NO:13) as primers. The amplification was carried out as follows: 1 cycle at 94° C. for 1 minutes, 35 cycles of 94° C. for 30 seconds, 55° C. for 30 seconds and 72° C. for 30 seconds, followed by 1 cycle at 72° C. for 10 minutes. The PCR products were visualized by agarose gel electrophoresis and the 555 bp probe was purified using a Gel Extraction Kit (Qiagen, Chatsworth, Calif.) according to manufacturer's instructions. The probe was radioactively labeled using the REDIPRIME DNA labeling kit (Amersham, Arlington Heights, Ill.) according to the manufacturer's instructions. The probe was purified using a NUCTRAP push column (Stratagene).

An in-house blot containing poly A+ RNA from human normal liver, human normal pancreas and the human melanoma cell lines including C32, Malme 3M, SK-MEL-2, and WM-115 was prehybridized in EXPRESSHYB (Clontech) for 3 hours at 65° C. Hybridization took place overnight at 65° C. using $10^6$ cpm/ml of labeled probe. The blots were then washed four times in 2×SSC and 0.1% SDS at room temp, followed by 2 washes in 0.1×SSC and 0.1% SDS at 50° C. A transcript of approximately 3.5 kb was observed most strongly in the Malme 3M cell line and weakly in the C32 and SK-MEL-2 cell lines. Liver, and pancreas tissues and the WM-115 cell line were negative at the 18 hour exposure time.

Example 11

Human ztnfr11 Tumor Polymerase Chain Reaction

A nested 5' RACE reaction was performed using marathon cDNAs from a lymphoma cell line (Burkitt's Lymphoma, DAUDI) and three osteosarcoma cell lines: MG63, HOS, and SaOS2. A 50 ul PCR reaction was run under the following conditions: 20 pmol of a sense primer corresponding to the vector sequence and 20 pmol if an antisense primer corresponding to the polynucleotide sequence as shown in SEQ ID NO:1 from nucleotide 664 to nucleotide 688 were used in a 3-step, 2-temperature reaction including an initial one minute at 94° C. followed by 5 cycles of 94° C. for 30 seconds and 72° C. for 5 minutes, then 5 cycles of 94° C. for 30 seconds and 70° C. for 5 minutes, then 25 cycles of 94° C. for 30 seconds and 68° C. for 5 minutes. A final extension of 72° C. for 10 min completed the reaction. One ul of a 1:50 dilution of the above reactions was used for nested 5' RACE using 20 pmol of an nested sense primer corresponding to the vector sequence and 20 pmol of an antisense primer corresponding to the polynucleotide sequence as shown in SEQ ID NO:1 from nucleotide 248 to nucleotide 272. A 50 µl reaction was set up and run under the following conditions. An initial one minute at 94° C. was followed by 4 cycles of 94° C. for 30 seconds and 72° C. for 5 minutes, then 4 cycles of 94° C. for 30 seconds and 70° C. for 5 minutes, then 20 cycles of 94° C. for 30 seconds and 68° C. for 5 minutes. The DAUDI, MG63, and SaOS2, were positive for a 250 bp band. The SaOS2 cell line also contained a 350 bp band. The HOS cell line contained a band of about 900 bp. All bands were sequenced and are isoforms of the ztnfr11 sequence.

Example 12

Additional Human ztnfr11 Tumor Polymerase Chain Reaction

A PCR reaction was set up using marathon cDNAs as follows: 30 pmol of a sense primer (corresponding to the polynucleotide as shown in SEQ ID NO:1 from nucleotide 441 to nucleotide 464) and an anti sense primer (corresponding to the polynucleotide as shown in SEQ ID NO:1 from nucleotide 856 to 879) were used in a 50 ul reaction in which an initial step of 94° C. for 1 minute was run followed by 3 cycles of 94° C. for 30 seconds, 63° C. for 30 seconds and 72° C. for 30 seconds then 32 cycles of 94° C. for 30 seconds, 61° C. for 30 seconds and 72° C. for 30 seconds with a final 10 minute extension at 72° C. Two bands were seen at ~530 bp and ~430 bp in MG63, DAUDI, U2OS, cell lines and thymus and pituitary tissues. These PCR bands were excised from the U2OS lane and submitted to sequencing. The upper band was found to have a ~82 bp insertion relative to the corresponding region of the polynucleotide as shown in SEQ ID NO:1. The polynucleotide sequence of the upper PCR band can be seen in SEQ ID NO:31. A polypeptide sequence corresponding to the variant polynucleotide sequence which contains the ~82 bp insertion can be seen in SEQ ID NO:27. A degenerate polynucleotide sequence for this variant is shown in SEQ ID NO:28. The polynucleotide sequence of this lower PCR band can be seen in SEQ ID NO:32. The lower PCR band was found to have the same insertion and an additional ~87 bp deletion relative to the corresponding region of the polynucleotide as shown in SEQ ID NO:1. A polypeptide sequence corresponding to this variant polynucleotide sequence which contains the ~82 bp insertion and the ~87 bp deletion can be seen in SEQ ID NO:29. A degenerate polynucleotide sequence for this variant is shown in SEQ ID NO:30.

These PCR bands were excised, purified using a Qiagen gel extraction kit and subcloned into the pCR 2.1 TOPO vector (Invitrogen, San Diego, Calif.). The resulting nucleotide sequence of the clone containing the 552 bp band (upper) is shown in SEQ ID NO: 33, which corresponds to the 175 residue amino acid sequence as shown in SEQ ID NO:34. A composite of the polypeptide sequence of SEQ ID NO:2 with SEQ ID NO:34 results in a 299 residue protein shown in SEQ ID NO:35. This variant of ztnfr11 differs from the polypeptide sequence as shown in SEQ ID NO:2 by a two amino acid insertion (Val-Ala) at residue 172 and a 28 residue insertion at residue 204 relative to the corresponding region of SEQ ID NO:2.

The resulting nucleotide sequence for the clone containing the 431 bp band (lower) is shown in SEQ ID NO:36, which corresponds to the 142 residue amino acid sequence shown in SEQ ID NO:37. A composite of the polypeptide sequence of SEQ ID NO:2 with SEQ ID NO:37 results in a 173 residue protein shown in SEQ ID NO:38. This variant of ztnfr11 differs from the polypeptide sequence as shown in SEQ ID NO:2 by a translation stop codon resulting in a truncated soluble ztnfr11 receptor.

Example 13

Identification of Cells Expressing ztnfr11 Using in Situ Hybridization

Specific human tissues were isolated and screened for ztnfr11 expression by in situ hybridization. Various human tissues prepared, sectioned and subjected to in situ hybridization included normal skin, melanoma skin, squamous cell carcinoma, psoriasis and cutaneous T-cell lymphoma skin samples, normal and adenocarcinoma colon and inflamed appendix samples. The tissues were fixed in 10% buffered formalin and blocked in paraffin using standard techniques. Tissues were sectioned at 4 to 8 microns. Tissues were prepared using a standard protocol ("Development of non-isotopic in situ hybridization" at http://dir.niehs.nih.gov/dirlep/ish.html). Briefly, tissue sections were deparaffinized with HistoClear (National Diagnostics, Atlanta, Ga.) and then dehydrated with ethanol. Next they were digested with Proteinase K (50 µg/ml) (Boehringer Diagnostics, Indianapolis, Ind.) at 37° C. for 2 to 20 minutes. This step was followed by acetylation and re-hydration of the tissues.

Two in situ probes generated by PCR were designed against the human ztnfr11 sequence. Two sets of oligos were designed to generate probes for separate regions of the ztnfr11 cDNA: (1) Oligos ZC26463 (SEQ ID NO:40) and ZC26464 (SEQ ID NO:41) were used to generate a 439 bp probe for ztnfr11 (from n.a. #576 to 1014); (2) ZC26470 (SEQ ID NO:42) and ZC26471 (SEQ ID NO:43) were used to generate a 548 bp probe for ztnfr11 (from n.a. #308 to 856). The antisense oligo from each set also contained the working sequence for the T7 RNA polymerase promoter to allow for easy transcription of antisense RNA probes from these PCR products. The PCR reaction conditions were as follows: 2 cycles at 95° C. for 30 sec, 50° C. for 1 min, 72° C. for 1 min followed by 33 cycles of 95° C. for 30 sec, 72° C. for 2 min. Probes were subsequently labeled with digoxigenin (Boehringer) or biotin (Boehringer) using an In Vitro transcription System (Promega, Madison, Wis.) as per manufacturer's instruction.

In situ hybridization was performed with a digoxigenin- or biotin-labeled ztnfr11 probe (above). The probe was added to the slides at a concentration of 1 to 5 pmol/ml for 12 to 16 hours at 60° C. Slides were subsequently washed in 2×SSC and 0.1×SSC at 55° C. The signals were amplified using tyramide signal amplification (TSA) (TSA, in situ indirect kit; NEN) and visualized with Vector Red substrate kit (Vector Lab) as per manufacturer's instructions. The slides were then counter-stained with hematoxylin (Vector Laboratories, Burlingame, Calif.).

Positive signals were seen in the human cutaneous T-cell lymphoma and melanoma skin samples. The positive-staining cells appeared to be keratinocytes in the cutaneous lymphoma skin, and very weak signal in melanocytes of melanoma skin samples. All other tissue samples tested were negative for ztnfr11.

Example 14

Construction of an Assay Cell Line

A BaF3 assay cell line was constructed for ztnfr11 ligand cloning. A ztnfr11/TNFR1 chimera was built in which the transmembrane and cytoplasmic domain of ztnfr11 were replaced by those of the TNFα receptor (TNFR1) (SEQ ID NO:44). The ztnfr11/TNFR1 chimera was transfected into a BaF3 cell line that contains a KZ159/mIL4 reporter gene (SEQ ID NO:45). Kz159/mIL4 responds to the activation of TNFR1 receptor by TNFα, triggering the expression and secretion of mIL4 that leads to the proliferation of BaF3 cells.

The extracellular domain of ztnfr11 was amplified with PCR primers ZC28835 (SEQ ID NO:46) and ZC28836 (SEQ ID NO:47) using ztnfr11 full-length cDNA as a template. The PCR reaction was as follows: 20 cycles of 94° C. for 30 sec and 68° C. for 2 min, then four more min at 68° C. and soak at 10° C. The transmembrane and cytoplasmic domain of mouse TNFR1 was amplified with PCR primers ZC28830 (SEQ ID NO:48) and ZC28837 (SEQ ID NO:49) using mouse placenta marathon cDNA as a template. The PCR reaction was as follows: 35 cycles of 94° C. for 30 sec and 68° C. for 2 min, then four more min at 68° C. and soak at 10° C. The PCR products were separated on 1% Agarose, a band of 500 bp (for ztnfr11) and 700 bp (for TNFR1) was excised and the DNA was purified using a QiaexII™ purification kit (Qiagen, Valencia, Calif.) according to the manufacturer's instruction.

The pZP7Z plasmid is a mammalian expression vector containing an expression cassette having the CMV promoter and a human growth hormone terminator. The plasmid also has an E. coli origin of replication, a mammalian selectable marker expression unit having an SV40 promoter, an enhancer and an origin of replication, as well as a Zeocin resistant gene, and SV40 terminator. About 30 ng of the restriction digested ztnfr11 insert (cut with EcoRI and PinA1) and TNFR1 insert (cut with PinA1 and Xba1) and about 10 ng of the digested vector (cut with EcoRI and Xba1) were ligated at 11° C. overnight. One microliter of ligation reaction was electroporated into DH10B competent cells (Gibco BRL, Rockville, Md.) according to manufacturer's direction and plated onto LB plates containing 50 ug/ml ampicillin, and incubated overnight. Colonies were screened by restriction analysis of DNA, which was prepared from 2 ml liquid cultures of individual colonies. The insert sequence of positive clones was verified by sequencing analysis (SEQ ID NO:50).

Ten million BaF3 cells that contain KZ159/mIL4 reporter were transfected with ztnfr11/TNFR1/pZP7Z plasmid by electroporation, and selected for Zeocin resistant stable transfectants. The proliferation of this stable cell line in response to TNFα without mIL-3 was assayed, and the activation of ztnfr11/TNFR1 chimera was tested using cross-linked anti-ztnfr11 reagent which was prepared by incubating rabbit anti-ztnfr11 antibody at 1 ug/ml with anti-rabbit immunoglobulin G (IgG) antibody-coupled magnetic beads. The positive clones then can be used as an assay cell line to screen for ztnfr11 ligand.

Example 15

Construction of a Transgenic Plasmid

Twenty μg of the pzp9 plasmid containing the ztnfr11-Fc4 soluble receptor sequence from Example 5 was digested with EcoRI and XbaI. The approximately 1 kb ztnfr11-Fc4 soluble receptor fragment was then isolated by running the digested vector on a 1.2% SeaPlaque GTG® gel and excising the fragment. DNA was purified using the QiaQuick™ (Qiagen) gel extraction kit. The EcoRI and XbaI overhangs were then converted to blunt ends using Klenow polymerase.

The ztnfr11-Fc4 soluble receptor fragment was then ligated into a apoA1 C1-17 transgenic vector, which was previously digested with PmeI. The apoA1 C1-17 plasmid was designed for expression of a gene of interest in transgenic mice. It contains an expression cassette comprised of the apoA1 promoter, the first apoA1 exon and a portion of the first intron, the ztnfr11-Fc4 coding sequence, a polylinker for the insertion of the desired clone and the human growth hormone poly A sequence.

About one microliter of the ligation reaction was electroporated into DH10B ElectroMax® competent cells (GIBCO BRL) according to manufacturer's direction, plated onto LB plates containing 100 μg/ml ampicillin, and incubated overnight at 37° C. Colonies were picked and grown in LB media containing 100 μg/ml ampicillin. Miniprep DNA was prepared from the picked clones and screened for the correctly oriented ztnfr11-Fc4 soluble receptor insert by restriction digestion analysis and subsequent agarose gel electrophoresis. Maxipreps of the correct apoA1 C1-17 ztnfr11-Fc4 soluble receptor construct were performed.

A NotI fragment containing expression cassette was prepared and used for microinjection into fertilized murine oocytes.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated polypeptide comprising residues 1 to 173 of SEQ ID NO:38.

2. An isolated polypeptide selected from the group consisting of:
   a) polypeptide molecules comprising residues 1 to 147 of SEQ ID NO:38;
   b) polypeptide molecules comprising residues 1 to 154 of SEQ ID NO:38;
   c) polypeptide molecules comprising residues 1 to 163 of SEQ ID NO:38; and
   d) polypeptide molecules comprising residues 1 to 165 of SEQ ID NO:38.

3. An isolated polypeptide consisting of residues 1 to 173 of SEQ ID NO:38.

4. An isolated polypeptide selected from the group consisting of:
   a) polypeptide molecule consisting of residues 1 to 147 of SEQ ID NO:38;
   b) polypeptide molecule consisting of residues 1 to 154 of SEQ ID NO:38;
   c) polypeptide molecule consisting of residues 1 to 163 of SEQ ID NO:38; and
   d) polypeptide molecule consisting of residues 1 to 165 of SEQ ID NO:38.

* * * * *

SEQUENCE LISTING

<160> NUMBER OF SEQ ID NOS: 50

<210> SEQ ID NO 1
<211> LENGTH: 1162
<212> TYPE: DNA
<213> ORGANISM: Homo sapiens
<220> FEATURE:
<221> NAME/KEY: CDS
<222> LOCATION: (104)...(913)

<400> SEQUENCE: 1

```
gaggggctg ggtgagatgt gtgctctgcg ctgaggtgga tttgtaccgg agtcccattt         60
gggagcaaga gccatctact cgtccgttac cggccttccc acc atg gat tgc caa       115
                                                  Met Asp Cys Gln
                                                    1 gaa aat gag tac tgg gac caa tgg gga cgg tgt gtc acc tgc caa cgg       163
Glu Asn Glu Tyr Trp Asp Gln Trp Gly Arg Cys Val Thr Cys Gln Arg
  5                  10                  15                  20 tgt ggt cct gga cag gag cta tcc aag gat tgt ggt tat gga gag ggt       211
Cys Gly Pro Gly Gln Glu Leu Ser Lys Asp Cys Gly Tyr Gly Glu Gly
                 25                  30                  35 gga gat gcc tac tgc aca gcc tgc cct cct cgc agg tac aaa agc agc       259
Gly Asp Ala Tyr Cys Thr Ala Cys Pro Pro Arg Arg Tyr Lys Ser Ser
             40                  45                  50 tgg ggc cac cac aaa tgt cag agt tgc atc acc tgt gct gtc atc aat       307
Trp Gly His His Lys Cys Gln Ser Cys Ile Thr Cys Ala Val Ile Asn
         55                  60                  65 cgt gtt cag aag gtc aac tgc aca gct acc tct aat gct gtc tgt ggg       355
Arg Val Gln Lys Val Asn Cys Thr Ala Thr Ser Asn Ala Val Cys Gly
```

```
gac tgt ttg ccc agg ttc tac cga aag aca cgc att gga ggc ctg cag      403
Asp Cys Leu Pro Arg Phe Tyr Arg Lys Thr Arg Ile Gly Gly Leu Gln
 85                  90                  95                 100 gac caa gag tgc atc ccg tgc acg aag cag acc ccc acc tct gag gtt      451
Asp Gln Glu Cys Ile Pro Cys Thr Lys Gln Thr Pro Thr Ser Glu Val
                    105                 110                 115 caa tgt gcc ttc cag ttg agc tta gtg gag gca gat gca ccc aca gtg      499
Gln Cys Ala Phe Gln Leu Ser Leu Val Glu Ala Asp Ala Pro Thr Val
                120                 125                 130 ccc cct cag gag gcc aca ctt gtt gca ctg gtg agc agc ctg cta gtg      547
Pro Pro Gln Glu Ala Thr Leu Val Ala Leu Val Ser Ser Leu Leu Val
            135                 140                 145 gtg ttt acc ctg gcc ttc ctg ggg ctc ttc ttc ctc tac tgc aag cag      595
Val Phe Thr Leu Ala Phe Leu Gly Leu Phe Phe Leu Tyr Cys Lys Gln
        150                 155                 160 ttc ttc aac aga cat tgc cag cgt gga ggt ttg ctg cag ttt gag gct      643
Phe Phe Asn Arg His Cys Gln Arg Gly Gly Leu Leu Gln Phe Glu Ala
165                 170                 175                 180 gat aaa aca gca aag gag gaa tct ctc ttc ccc gtg cca ccc agc aag      691
Asp Lys Thr Ala Lys Glu Glu Ser Leu Phe Pro Val Pro Pro Ser Lys
                185                 190                 195 gag acc agt gct gag tcc caa gag tcc ttt acc atg gcc tcc tgc acc      739
Glu Thr Ser Ala Glu Ser Gln Glu Ser Phe Thr Met Ala Ser Cys Thr
            200                 205                 210 tca gag agc cac tcc cac tgg gtc cac agc ccc atc gaa tgc aca gag      787
Ser Glu Ser His Ser His Trp Val His Ser Pro Ile Glu Cys Thr Glu
        215                 220                 225 ctg gac ctg caa aag ttt tcc agc tct gcc tcc tat act gga gct gag      835
Leu Asp Leu Gln Lys Phe Ser Ser Ser Ala Ser Tyr Thr Gly Ala Glu
230                 235                 240 acc ttg ggg gga aac aca gtc gaa agc act gga gac agg ctg gag ctc      883
Thr Leu Gly Gly Asn Thr Val Glu Ser Thr Gly Asp Arg Leu Glu Leu
245                 250                 255                 260 aat gtg ccc ttt gaa gtt ccc agc cct taa ctctaatgag gtctcttggg        933
Asn Val Pro Phe Glu Val Pro Ser Pro *
                265 cccctggcag ccttgcccag ttgttctctc tggactctgt tcctatacca caacagcagc    993 aggggcctga aatgtgatgt ccacaagagc taatacccta cagatggggc atatcctatc   1053 ccatcccacc agaggattga ttctccattt cacaaggact gatctggagc atttcttgct   1113 tccctgttgt agtctgggga gccagattcc acatgcatgg ggcggccgc               1162

<210> SEQ ID NO 2
<211> LENGTH: 269
<212> TYPE: PRT
<213> ORGANISM: Homo sapiens

<400> SEQUENCE: 2

Met Asp Cys Gln Glu Asn Glu Tyr Trp Asp Gln Trp Gly Arg Cys Val
  1               5                  10                  15

Thr Cys Gln Arg Cys Gly Pro Gly Gln Glu Leu Ser Lys Asp Cys Gly
                 20                  25                  30

Tyr Gly Glu Gly Gly Asp Ala Tyr Cys Thr Ala Cys Pro Pro Arg Arg
             35                  40                  45

Tyr Lys Ser Ser Trp Gly His His Lys Cys Gln Ser Cys Ile Thr Cys
         50                  55                  60

Ala Val Ile Asn Arg Val Gln Lys Val Asn Cys Thr Ala Thr Ser Asn
```

-continued

```
            65                  70                  75                  80
Ala Val Cys Gly Asp Cys Leu Pro Arg Phe Tyr Arg Lys Thr Arg Ile
                85                  90                  95

Gly Gly Leu Gln Asp Gln Glu Cys Ile Pro Cys Thr Lys Gln Thr Pro
            100                 105                 110

Thr Ser Glu Val Gln Cys Ala Phe Gln Leu Ser Leu Val Glu Ala Asp
        115                 120                 125

Ala Pro Thr Val Pro Pro Gln Glu Ala Thr Leu Val Ala Leu Val Ser
    130                 135                 140

Ser Leu Leu Val Val Phe Thr Leu Ala Phe Leu Gly Leu Phe Phe Leu
145                 150                 155                 160

Tyr Cys Lys Gln Phe Phe Asn Arg His Cys Gln Arg Gly Gly Leu Leu
                165                 170                 175

Gln Phe Glu Ala Asp Lys Thr Ala Lys Glu Glu Ser Leu Phe Pro Val
            180                 185                 190

Pro Pro Ser Lys Glu Thr Ser Ala Glu Ser Gln Glu Ser Phe Thr Met
        195                 200                 205

Ala Ser Cys Thr Ser Glu Ser His Ser His Trp Val His Ser Pro Ile
    210                 215                 220

Glu Cys Thr Glu Leu Asp Leu Gln Lys Phe Ser Ser Ser Ala Ser Tyr
225                 230                 235                 240

Thr Gly Ala Glu Thr Leu Gly Gly Asn Thr Val Glu Ser Thr Gly Asp
                245                 250                 255

Arg Leu Glu Leu Asn Val Pro Phe Glu Val Pro Ser Pro
            260                 265
```

<210> SEQ ID NO 3
<211> LENGTH: 807
<212> TYPE: DNA
<213> ORGANISM: Artificial Sequence
<220> FEATURE:
<223> OTHER INFORMATION: degenerate sequence
<220> FEATURE:
<221> NAME/KEY: misc_feature
<222> LOCATION: (1)...(807)
<223> OTHER INFORMATION: n = A,T,C or G

<400> SEQUENCE: 3

```
atggaytgyc argaraayga rtaytgggay cartggggnm gntgygtnac ntgycarmgn      60
tgyggnccng gncargaryt nwsnaargay tgyggntayg gngarggngg ngaygcntay     120
tgyacngcnt gyccnccnmg nmgntayaar wsnwsntggg gncaycayaa rtgycarwsn     180
tgyathacnt gygcngtnat haaymgngtn caraargtna aytgyacngc nacnwsnaay     240
gcngtntgyg gngaytgyyt nccnmgntty taymgnaara cnmgnathgg nggnytncar     300
gaycargart gyathccntg yacnaarcar acnccnacnw sngargtnca rtgygcntty     360
carytnwsny tngtngargc ngaygcnccn acngtnccnc cncargargc nacnytngtn     420
gcnytngtnw snwsnytnyt ngtngtntty acnytngcnt tyytnggnyt nttyttyytn     480
taytgyaarc arttyttyaa ymgncaytgy carmgnggng gnytnytnca rttygargcn     540
gayaaracng cnaargarga rwsnytntty ccngtnccnc cnwsnaarga racnwsngcn     600
garwsncarg arwsnttyac natggcnwsn tgyacnwsng arwsncayws ncaytgggtn     660
caywsnccna thgartgyac ngarytngay ytncaraart tywsnwsnws ngcnwsntay     720
acnggngcna aracnytngg nggnaaytac ngtngarwsna cnggngaymg nytngarytn     780
aaygtnccnt tygargtncc nwsnccn                                         807
```

```
<210> SEQ ID NO 4
<211> LENGTH: 41
<212> TYPE: PRT
<213> ORGANISM: Artificial Sequence
<220> FEATURE:
<223> OTHER INFORMATION: Pseudo repeat motif #1
<220> FEATURE:
<221> NAME/KEY: VARIANT
<222> LOCATION: (1)...(1)
<223> OTHER INFORMATION: Xaa is any amino acid residue
<220> FEATURE:
<221> NAME/KEY: VARIANT
<222> LOCATION: (3)...(12)
<223> OTHER INFORMATION: Each Xaa is independently any amino acid
      residue
<220> FEATURE:
<221> NAME/KEY: VARIANT
<222> LOCATION: (13)...(16)
<223> OTHER INFORMATION: Each Xaa is independently any amino acid
      residue or not present
<220> FEATURE:
<221> NAME/KEY: VARIANT
<222> LOCATION: (19)...(20)
<223> OTHER INFORMATION: Each Xaa is independently any amino acid
      residue
<220> FEATURE:
<221> NAME/KEY: VARIANT
<222> LOCATION: (22)...(26)
<223> OTHER INFORMATION: Each Xaa is independently any amino acid
      residue
<220> FEATURE:
<221> NAME/KEY: VARIANT
<222> LOCATION: (27)...(30)
<223> OTHER INFORMATION: Each Xaa is independently any amino acid
      residue
      or not present
<220> FEATURE:
<221> NAME/KEY: VARIANT
<222> LOCATION: (32)...(37)
<223> OTHER INFORMATION: Each Xaa is independently any amino acid
      residue or not present
<220> FEATURE:
<221> NAME/KEY: VARIANT
<222> LOCATION: (38)...(39)
<223> OTHER INFORMATION: Each Xaa is independently any amino acid
      residue or not present
<220> FEATURE:
<221> NAME/KEY: VARIANT
<222> LOCATION: (41)...(41)
<223> OTHER INFORMATION: Xaa is any amino acid residue

<400> SEQUENCE: 4

Xaa Cys Xaa Xaa Xaa Xaa Xaa Xaa Xaa Xaa Xaa Xaa Xaa Xaa Xaa Xaa
 1               5                  10                  15

Cys Cys Xaa Xaa Cys Xaa Xaa Xaa Xaa Xaa Xaa Xaa Xaa Xaa Cys Xaa
            20                  25                  30

Xaa Xaa Xaa Xaa Xaa Xaa Xaa Cys Xaa
        35                  40

<210> SEQ ID NO 5
<211> LENGTH: 45
<212> TYPE: PRT
<213> ORGANISM: Artificial Sequence
<220> FEATURE:
<223> OTHER INFORMATION: Pseudo repeat motif #2
<220> FEATURE:
<221> NAME/KEY: VARIANT
<222> LOCATION: (1)...(1)
<223> OTHER INFORMATION: Xaa is any amino acid residue
<220> FEATURE:
<221> NAME/KEY: VARIANT
<222> LOCATION: (3)...(15)
<223> OTHER INFORMATION: Each Xaa is independently any amino acid
```

```
                           residue
<220> FEATURE:
<221> NAME/KEY: VARIANT
<222> LOCATION: (16)...(17)
<223> OTHER INFORMATION: Each Xaa is independently any amino acid
      residue or not present
<220> FEATURE:
<221> NAME/KEY: VARIANT
<222> LOCATION: (19)...(20)
<223> OTHER INFORMATION: Each Xaa is independently any amino acid
      residue
<220> FEATURE:
<221> NAME/KEY: VARIANT
<222> LOCATION: (22)...(23)
<223> OTHER INFORMATION: Each Xaa is independently any amino acid
      residue
<220> FEATURE:
<221> NAME/KEY: VARIANT
<222> LOCATION: (24)...(24)
<223> OTHER INFORMATION: Each Xaa is independently any amino acid
      residue
      or not present
<220> FEATURE:
<221> NAME/KEY: VARIANT
<222> LOCATION: (26)...(33)
<223> OTHER INFORMATION: Each Xaa is independently any amino acid
      residue
<220> FEATURE:
<221> NAME/KEY: VARIANT
<222> LOCATION: (34)...(36)
<223> OTHER INFORMATION: Each Xaa is independently any amino acid
      residue or not present
<220> FEATURE:
<221> NAME/KEY: VARIANT
<222> LOCATION: (38)...(44)
<223> OTHER INFORMATION: Each Xaa is independently any amino acid
      residue

<400> SEQUENCE: 5

Xaa Cys Xaa Xaa Xaa Xaa Xaa Xaa Xaa Xaa Xaa Xaa Xaa Xaa Xaa Xaa
 1               5                   10                  15

Xaa Cys Xaa Xaa Cys Xaa Xaa Xaa Cys Xaa Xaa Xaa Xaa Xaa Xaa Xaa
             20                  25                  30

Xaa Xaa Xaa Xaa Cys Xaa Xaa Xaa Xaa Xaa Xaa Xaa Cys
         35                  40                  45

<210> SEQ ID NO 6
<211> LENGTH: 49
<212> TYPE: PRT
<213> ORGANISM: Artificial Sequence
<220> FEATURE:
<223> OTHER INFORMATION: Pseudo repeat motif #3
<220> FEATURE:
<221> NAME/KEY: VARIANT
<222> LOCATION: (1)...(1)
<223> OTHER INFORMATION: Xaa is any amino acid residue
<220> FEATURE:
<221> NAME/KEY: VARIANT
<222> LOCATION: (3)...(7)
<223> OTHER INFORMATION: Each Xaa is independently any amino acid
      residue
<220> FEATURE:
<221> NAME/KEY: VARIANT
<222> LOCATION: (8)...(8)
<223> OTHER INFORMATION: Xaa is any amino acid residue or not
      present
<220> FEATURE:
<221> NAME/KEY: VARIANT
<222> LOCATION: (9)...(14)
<223> OTHER INFORMATION: Each Xaa is independently any amino acid
      residue
<220> FEATURE:
<221> NAME/KEY: VARIANT
<222> LOCATION: (15)...(18)
<223> OTHER INFORMATION: Each Xaa is independently any amino acid
```

```
          residue or not present
<220> FEATURE:
<221> NAME/KEY: VARIANT
<222> LOCATION: (20)...(21)
<223> OTHER INFORMATION: Each Xaa is independently any amino acid
      residue
<220> FEATURE:
<221> NAME/KEY: VARIANT
<222> LOCATION: (23)...(24)
<223> OTHER INFORMATION: Each Xaa is independently any amino acid
      residue
<220> FEATURE:
<221> NAME/KEY: VARIANT
<222> LOCATION: (25)...(29)
<223> OTHER INFORMATION: Each Xaa is independently any amino acid
      residue or not present
<220> FEATURE:
<221> NAME/KEY: VARIANT
<222> LOCATION: (31)...(38)
<223> OTHER INFORMATION: Each Xaa is independently any amino acid
      residue
<220> FEATURE:
<221> NAME/KEY: VARIANT
<222> LOCATION: (39)...(39)
<223> OTHER INFORMATION: Xaa is  any amino acid residue or not present
<220> FEATURE:
<221> NAME/KEY: VARIANT
<222> LOCATION: (41)...(47)
<223> OTHER INFORMATION: Each Xaa is independently any amino acid
      residue
<220> FEATURE:
<221> NAME/KEY: VARIANT
<222> LOCATION: (49)...(49)
<223> OTHER INFORMATION: Xaa is any amino acid residue or not present

<400> SEQUENCE: 6

Xaa Cys Xaa Xaa Xaa Xaa Xaa Xaa Xaa Xaa Xaa Xaa Xaa Xaa Xaa Xaa
 1               5                   10                  15

Xaa Xaa Cys Xaa Xaa Cys Xaa Xaa Xaa Xaa Xaa Xaa Cys Xaa Xaa
             20                  25                  30

Xaa Xaa Xaa Xaa Xaa Xaa Xaa Cys Xaa Xaa Xaa Xaa Xaa Xaa Xaa Cys
         35                  40                  45

Xaa

<210> SEQ ID NO 7
<211> LENGTH: 48
<212> TYPE: PRT
<213> ORGANISM: Artificial Sequence
<220> FEATURE:
<223> OTHER INFORMATION: Pseudo repeat motif #3 alternative motif
<220> FEATURE:
<221> NAME/KEY: VARIANT
<222> LOCATION: (1)...(1)
<223> OTHER INFORMATION: Xaa is any amino acid residue
<220> FEATURE:
<221> NAME/KEY: VARIANT
<222> LOCATION: (3)...(7)
<223> OTHER INFORMATION: Each Xaa is independently any amino acid
      residue
<220> FEATURE:
<221> NAME/KEY: VARIANT
<222> LOCATION: (8)...(8)
<223> OTHER INFORMATION: Xaa is independently any amino acid residue or
      not present
<220> FEATURE:
<221> NAME/KEY: VARIANT
<222> LOCATION: (10)...(13)
<223> OTHER INFORMATION: Each Xaa is independently any amino acid
      residue
<220> FEATURE:
<221> NAME/KEY: VARIANT
<222> LOCATION: (14)...(18)
<223> OTHER INFORMATION: Each Xaa is independently any amino acid
      residue
```

```
      or not present
<220> FEATURE:
<221> NAME/KEY: VARIANT
<222> LOCATION: (20)...(21)
<223> OTHER INFORMATION: Each Xaa is independently any amino acid
      residue
<220> FEATURE:
<221> NAME/KEY: VARIANT
<222> LOCATION: (23)...(24)
<223> OTHER INFORMATION: Each Xaa is independently any amino acid
      residue
<220> FEATURE:
<221> NAME/KEY: VARIANT
<222> LOCATION: (25)...(29)
<223> OTHER INFORMATION: Each Xaa is independently any amino acid
      residue or not present
<220> FEATURE:
<221> NAME/KEY: VARIANT
<222> LOCATION: (31)...(40)
<223> OTHER INFORMATION: Each Xaa is independently any amino acid
      residue
<220> FEATURE:
<221> NAME/KEY: VARIANT
<222> LOCATION: (41)...(46)
<223> OTHER INFORMATION: Each Xaa is independently any amino acid
      residue or not present
<220> FEATURE:
<221> NAME/KEY: VARIANT
<222> LOCATION: (48)...(48)
<223> OTHER INFORMATION: Xaa is any amino acid residue

<400> SEQUENCE: 7

Xaa Cys Xaa Xaa Xaa Xaa Xaa Xaa Cys Xaa Xaa Xaa Xaa Xaa Xaa Xaa
 1               5                  10                  15

Xaa Xaa Cys Xaa Xaa Cys Xaa Xaa Xaa Xaa Xaa Xaa Cys Xaa Xaa
            20                  25                  30

Xaa Xaa Xaa Xaa Xaa Xaa Xaa Xaa Xaa Xaa Xaa Xaa Xaa Cys Xaa
        35                  40                  45

<210> SEQ ID NO 8
<211> LENGTH: 43
<212> TYPE: PRT
<213> ORGANISM: Artificial Sequence
<220> FEATURE:
<223> OTHER INFORMATION: Pseudo repeat motif #4
<220> FEATURE:
<221> NAME/KEY: VARIANT
<222> LOCATION: (1)...(1)
<223> OTHER INFORMATION: Xaa is any amino acid residue
<220> FEATURE:
<221> NAME/KEY: VARIANT
<222> LOCATION: (3)...(12)
<223> OTHER INFORMATION: Each Xaa is independently any amino acid
      residue
<220> FEATURE:
<221> NAME/KEY: VARIANT
<222> LOCATION: (13)...(16)
<223> OTHER INFORMATION: Each Xaa is independently any amino acid
      residue or not present
<220> FEATURE:
<221> NAME/KEY: VARIANT
<222> LOCATION: (18)...(19)
<223> OTHER INFORMATION: Each Xaa is independently any amino acid
      residue
<220> FEATURE:
<221> NAME/KEY: VARIANT
<222> LOCATION: (21)...(22)
<223> OTHER INFORMATION: Each Xaa is independently any amino acid
      residue
<220> FEATURE:
<221> NAME/KEY: VARIANT
<222> LOCATION: (24)...(27)
<223> OTHER INFORMATION: Each Xaa is independently any amino acid
      residue
<220> FEATURE:
```

```
<221> NAME/KEY: VARIANT
<222> LOCATION: (28)...(33)
<223> OTHER INFORMATION: Each Xaa is independently any amino acid
      residue or not present
<220> FEATURE:
<221> NAME/KEY: VARIANT
<222> LOCATION: (35)...(37)
<223> OTHER INFORMATION: Each Xaa is independently any amino acid
      residue
<220> FEATURE:
<221> NAME/KEY: VARIANT
<222> LOCATION: (38)...(41)
<223> OTHER INFORMATION: Each Xaa is independently any amino acid
      residue or not present
<220> FEATURE:
<221> NAME/KEY: VARIANT
<222> LOCATION: (43)...(43)
<223> OTHER INFORMATION: Each Xaa is independently any amino acid
      residue

<400> SEQUENCE: 8

Xaa Cys Xaa Xaa Xaa Xaa Xaa Xaa Xaa Xaa Xaa Xaa Xaa Xaa Xaa Xaa
 1               5                   10                  15

Cys Xaa Xaa Cys Xaa Xaa Cys Xaa Xaa Xaa Xaa Xaa Xaa Xaa Xaa
            20                  25                  30

Xaa Cys Xaa Xaa Xaa Xaa Xaa Xaa Xaa Cys Xaa
        35                  40

<210> SEQ ID NO 9
<211> LENGTH: 43
<212> TYPE: PRT
<213> ORGANISM: Artificial Sequence
<220> FEATURE:
<223> OTHER INFORMATION: Pseudo repeat motif #4 alternative motif
<220> FEATURE:
<221> NAME/KEY: VARIANT
<222> LOCATION: (1)...(1)
<223> OTHER INFORMATION: Xaa is any amino acid residue
<220> FEATURE:
<221> NAME/KEY: VARIANT
<222> LOCATION: (3)...(12)
<223> OTHER INFORMATION: Each Xaa is independently any amino acid
      residue
<220> FEATURE:
<221> NAME/KEY: VARIANT
<222> LOCATION: (13)...(16)
<223> OTHER INFORMATION: Each Xaa is independently any amino acid
      residue or not present
<220> FEATURE:
<221> NAME/KEY: VARIANT
<222> LOCATION: (18)...(22)
<223> OTHER INFORMATION: Each Xaa is independently any amino acid
      residue
<220> FEATURE:
<221> NAME/KEY: VARIANT
<222> LOCATION: (24)...(27)
<223> OTHER INFORMATION: Each Xaa is independently any amino acid
      residue
<220> FEATURE:
<221> NAME/KEY: VARIANT
<222> LOCATION: (28)...(33)
<223> OTHER INFORMATION: Each Xaa is independently any amino acid
      residue or not present
<220> FEATURE:
<221> NAME/KEY: VARIANT
<222> LOCATION: (34)...(37)
<223> OTHER INFORMATION: Each Xaa is independently any amino acid
      residue
<220> FEATURE:
<221> NAME/KEY: VARIANT
<222> LOCATION: (38)...(41)
<223> OTHER INFORMATION: Each Xaa is independently any amino acid
      residue or not present
<220> FEATURE:
<221> NAME/KEY: VARIANT
```

```
<222> LOCATION: (43)...(43)
<223> OTHER INFORMATION: Xaa is any amino acid residue

<400> SEQUENCE: 9

Xaa Cys Xaa Xaa Xaa Xaa Xaa Xaa Xaa Xaa Xaa Xaa Xaa Xaa Xaa
 1               5                   10                  15

Cys Xaa Xaa Xaa Xaa Xaa Cys Xaa Xaa Xaa Xaa Xaa Xaa Xaa Xaa
             20                  25                  30

Xaa Xaa Xaa Xaa Xaa Xaa Xaa Xaa Xaa Cys Xaa
         35                  40

<210> SEQ ID NO 10
<211> LENGTH: 18
<212> TYPE: DNA
<213> ORGANISM: Artificial Sequence
<220> FEATURE:
<223> OTHER INFORMATION: oligonucleotide primer ZC25352

<400> SEQUENCE: 10
ccttgcccag ttgttctc                                             18

<210> SEQ ID NO 11
<211> LENGTH: 18
<212> TYPE: DNA
<213> ORGANISM: Artificial Sequence
<220> FEATURE:
<223> OTHER INFORMATION: oligonucleotide primer ZC25353

<400> SEQUENCE: 11
tctggtggga tgggatag                                             18

<210> SEQ ID NO 12
<211> LENGTH: 26
<212> TYPE: DNA
<213> ORGANISM: Artificial Sequence
<220> FEATURE:
<223> OTHER INFORMATION: oligonucleotide primer ZC25364

<400> SEQUENCE: 12
acctgtgctg tcatcaatcg tgttca                                    26

<210> SEQ ID NO 13
<211> LENGTH: 24
<212> TYPE: DNA
<213> ORGANISM: Artificial Sequence
<220> FEATURE:
<223> OTHER INFORMATION: oligonucleotide primer ZC25365

<400> SEQUENCE: 13
cccccaaggt ctcagctcca gtat                                      24

<210> SEQ ID NO 14
<211> LENGTH: 18
<212> TYPE: DNA
<213> ORGANISM: Artificial Sequence
<220> FEATURE:
<223> OTHER INFORMATION: oligonucleotide primer ZC25352

<400> SEQUENCE: 14
ccttgcccag ttgttctc                                             18

<210> SEQ ID NO 15
<211> LENGTH: 18
<212> TYPE: DNA
<213> ORGANISM: Artificial Sequence
```

```
<220> FEATURE:
<223> OTHER INFORMATION: oligonucleotide primer ZC25353

<400> SEQUENCE: 15
tctggtggga tgggatag                                                    18

<210> SEQ ID NO 16
<211> LENGTH: 6
<212> TYPE: PRT
<213> ORGANISM: Artificial Sequence
<220> FEATURE:
<223> OTHER INFORMATION: Artificial Protein

<400> SEQUENCE: 16

Glu Tyr Met Pro Met Glu
 1               5

<210> SEQ ID NO 17
<211> LENGTH: 33
<212> TYPE: DNA
<213> ORGANISM: Artificial Sequence
<220> FEATURE:
<223> OTHER INFORMATION: oligonucleotide primer ZC25598

<400> SEQUENCE: 17
gcggatccga ttgccaagaa aatgagtact ggg                                   33

<210> SEQ ID NO 18
<211> LENGTH: 37
<212> TYPE: DNA
<213> ORGANISM: Artificial Sequence
<220> FEATURE:
<223> OTHER INFORMATION: oligonucleotide primer ZC25596

<400> SEQUENCE: 18
gcagatctgg gctccactgt gggtgcatct gcctcca                               37

<210> SEQ ID NO 19
<211> LENGTH: 108
<212> TYPE: DNA
<213> ORGANISM: Homo sapiens
<220> FEATURE:
<223> OTHER INFORMATION: tPA leader

<400> SEQUENCE: 19
atggatgcaa tgaagagagg gctctgctgt gtgctgctgc tgtgtggcgc cgtcttcgtt      60
tcgctcagcc aggaaatcca tgccgagttg agacgcttcc gtagatcc                  108

<210> SEQ ID NO 20
<211> LENGTH: 693
<212> TYPE: DNA
<213> ORGANISM: Artificial Sequence
<220> FEATURE:
<223> OTHER INFORMATION: Fc4 tag

<400> SEQUENCE: 20
agatcttcag acaaaactca cacatgccca ccgtgcccag cacctgaagc cgaggggggca     60 ccgtcagtct tcctcttccc cccaaaaccc aaggacaccc tcatgatctc ccggacccct    120
gaggtcacat gcgtggtggt ggacgtgagc cacgaagacc ctgaggtcaa gttcaactgg    180
tacgtggacg gcgtggaggt gcataatgcc aagacaaagc cgcgggagga gcagtacaac    240
agcacgtacc gtgtggtcag cgtcctcacc gtcctgcacc aggactggct gaatggcaag    300
gagtacaagt gcaaggtctc caacaaagcc ctcccatcct ccatcgagaa aaccatctcc    360
```

```
aaagccaaag ggcagccccg agaaccacag gtgtacaccc tgcccccatc ccgggatgag    420
ctgaccaaga accaggtcag cctgacctgc ctggtcaaag gcttctatcc cagcgacatc    480
gccgtggagt gggagagcaa tgggcagccg agaacaact acaagaccac gcctcccgtg     540
ctggactccg acggctcctt cttcctctac agcaagctca ccgtggacaa gagcaggtgg    600
cagcagggga acgtcttctc atgctccgtg atgcatgagg ctctgcacaa ccactacacg    660
cagaagagcc tctccctgtc tccgggtaaa taa                                 693

<210> SEQ ID NO 21
<211> LENGTH: 534
<212> TYPE: DNA
<213> ORGANISM: Artificial Sequence
<220> FEATURE:
<223> OTHER INFORMATION: Polynucleotide Construct

<400> SEQUENCE: 21
atggatgcaa tgaagagagg gctctgctgt gtgctgctgc tgtgtggcgc cgtcttcgtt    60
tcgctcagcc aggaaatcca tgccgagttg agacgcttcc gtagatccga ttgccaagaa    120
aatgagtact gggaccaatg gggacggtgt gtcacctgcc aacggtgtgg tcctggacag    180
gagctatcca aggattgtgg ttatggagag ggtggagatg cctactgcac agcctgccct    240
cctcgcaggt acaaaagcag ctggggccac cacaaatgtc agagttgcat cacctgtgct    300
gtcatcaatc gtgttcagaa ggtcaactgc acagctacct ctaatgctgt ctgtggggac    360
tgtttgccca ggttctaccg aaagacacg attggaggcc tgcaggacca agagtgcatc     420
ccgtgcacga agcagacccc cacctctgag gttcaatgtg ccttccagtt gagcttagtg    480
gaggcagatg cacccacagt ggagcccaga tctgaatata tgcccatgga ataa          534

<210> SEQ ID NO 22
<211> LENGTH: 1200
<212> TYPE: DNA
<213> ORGANISM: Artificial Sequence
<220> FEATURE:
<223> OTHER INFORMATION: construct

<400> SEQUENCE: 22
atggatgcaa tgaagagagg gctctgctgt gtgctgctgc tgtgtggcgc cgtcttcgtt    60
tcgctcagcc aggaaatcca tgccgagttg agacgcttcc gtagatccga ttgccaagaa    120
aatgagtact gggaccaatg gggacggtgt gtcacctgcc aacggtgtgg tcctggacag    180
gagctatcca aggattgtgg ttatggagag ggtggagatg cctactgcac agcctgccct    240
cctcgcaggt acaaaagcag ctggggccac cacaaatgtc agagttgcat cacctgtgct    300
gtcatcaatc gtgttcagaa ggtcaactgc acagctacct ctaatgctgt ctgtggggac    360
tgtttgccca ggttctaccg aaagacacg attggaggcc tgcaggacca agagtgcatc     420
ccgtgcacga agcagacccc cacctctgag gttcaatgtg ccttccagtt gagcttagtg    480
gaggcagatg cacccacagt ggagcccaga tcttcagaca aaactcacac atgcccaccg    540
tgcccagcac ctgaagccga ggggcaccg tcagtcttcc tcttcccccc aaaacccaag     600
gacaccctca tgatctcccg gacccctgag gtcacatgcg tggtggtgga cgtgagccac    660
gaagaccctg aggtcaagtt caactggtac gtggacggcg tggaggtgca taatgccaag    720
acaaagccgc gggaggagca gtacaacagc acgtaccgtg tggtcagcgt cctcaccgtc    780
ctgcaccagg actggctgaa tggcaaggag tacaagtgca aggtctccaa caaagccctc    840
```

```
ccatcctcca tcgagaaaac catctccaaa gccaagggc agccccgaga accacaggtg    900
tacaccctgc ccccatcccg ggatgagctg accaagaacc aggtcagcct gacctgcctg    960
gtcaaaggct tctatcccag cgacatcgcc gtggagtggg agagcaatgg gcagccggag   1020
aacaactaca agaccacgcc tcccgtgctg gactccgacg gctccttctt cctctacagc   1080
aagctcaccg tggacaagag caggtggcag caggggaacg tcttctcatg ctccgtgatg   1140
catgaggctc tgcacaacca ctacacgcag aagagcctct ccctgtctcc gggtaaataa   1200
```

<210> SEQ ID NO 23  
<211> LENGTH: 47  
<212> TYPE: DNA  
<213> ORGANISM: Artificial Sequence  
<220> FEATURE:  
<223> OTHER INFORMATION: Oligonucleotide ZC26463

<400> SEQUENCE: 23

```
atgcattaac cctcactaaa gggccttcct ggggctcttc ttcctct                    47
```

<210> SEQ ID NO 24  
<211> LENGTH: 46  
<212> TYPE: DNA  
<213> ORGANISM: Artificial Sequence  
<220> FEATURE:  
<223> OTHER INFORMATION: Oligonucleotide ZC26464

<400> SEQUENCE: 24

```
taatacgact cactatoggg aggggcccct gctgctgttg tggtat                     46
```

<210> SEQ ID NO 25  
<211> LENGTH: 49  
<212> TYPE: DNA  
<213> ORGANISM: Artificial Sequence  
<220> FEATURE:  
<223> OTHER INFORMATION: Oligonucleotide ZC26470

<400> SEQUENCE: 25

```
atgcattaac cctcactaaa gggacctgtg ctgtcatcaa tcgtgttca                  49
```

<210> SEQ ID NO 26  
<211> LENGTH: 47  
<212> TYPE: DNA  
<213> ORGANISM: Artificial Sequence  
<220> FEATURE:  
<223> OTHER INFORMATION: Oligonucleotide ZC26471

<400> SEQUENCE: 26

```
taatacgact cactataggg aggcccccaa ggtctcagct ccagtat                    47
```

<210> SEQ ID NO 27  
<211> LENGTH: 297  
<212> TYPE: PRT  
<213> ORGANISM: Homo sapiens

<400> SEQUENCE: 27

```
Met Asp Cys Gln Glu Asn Glu Tyr Trp Asp Gln Trp Gly Arg Cys Val
 1               5                  10                  15

Thr Cys Gln Arg Cys Gly Pro Gly Gln Glu Leu Ser Lys Asp Cys Gly
                20                  25                  30

Tyr Gly Glu Gly Gly Asp Ala Tyr Cys Thr Ala Cys Pro Pro Arg Arg
            35                  40                  45

Tyr Lys Ser Ser Trp Gly His His Lys Cys Gln Ser Cys Ile Thr Cys
        50                  55                  60
```

```
Ala Val Ile Asn Arg Val Gln Lys Val Asn Cys Thr Ala Thr Ser Asn
 65                  70                  75                  80

Ala Val Cys Gly Asp Cys Leu Pro Arg Phe Tyr Arg Lys Thr Arg Ile
                 85                  90                  95

Gly Gly Leu Gln Asp Gln Glu Cys Ile Pro Cys Thr Lys Gln Thr Pro
            100                 105                 110

Thr Ser Glu Val Gln Cys Ala Phe Gln Leu Ser Leu Val Glu Ala Asp
        115                 120                 125

Ala Pro Thr Val Pro Pro Gln Glu Ala Thr Leu Val Ala Leu Val Ser
    130                 135                 140

Ser Leu Leu Val Val Phe Thr Leu Ala Phe Leu Gly Leu Phe Phe Leu
145                 150                 155                 160

Tyr Cys Lys Gln Phe Phe Asn Arg His Cys Gln Arg Gly Gly Leu Leu
                165                 170                 175

Gln Phe Glu Ala Asp Lys Thr Ala Lys Glu Glu Ser Leu Phe Pro Val
            180                 185                 190

Pro Pro Ser Lys Glu Thr Ser Ala Glu Ser Gln Val Ser Glu Asn Ile
        195                 200                 205

Phe Gln Thr Gln Pro Leu Asn Pro Ile Leu Glu Asp Asp Cys Ser Ser
    210                 215                 220

Thr Ser Gly Phe Pro Thr Gln Glu Ser Phe Thr Met Ala Ser Cys Thr
225                 230                 235                 240

Ser Glu Ser His Ser His Trp Val His Ser Pro Ile Glu Cys Thr Glu
                245                 250                 255

Leu Asp Leu Gln Lys Phe Ser Ser Ser Ala Ser Tyr Thr Gly Ala Glu
            260                 265                 270

Thr Leu Gly Gly Asn Thr Val Glu Ser Thr Gly Asp Arg Leu Glu Leu
        275                 280                 285

Asn Val Pro Phe Glu Val Pro Ser Pro
    290                 295

<210> SEQ ID NO 28
<211> LENGTH: 891
<212> TYPE: DNA
<213> ORGANISM: Artificial Sequence
<220> FEATURE:
<223> OTHER INFORMATION: degenerate sequence
<220> FEATURE:
<221> NAME/KEY: misc_feature
<222> LOCATION: (1)...(891)
<223> OTHER INFORMATION: n = A,T,C or G

<400> SEQUENCE: 28
atggaytgyc argaraayga rtaytgggay cartggggnm gntgygtnac ntgycarmgn      60
tgyggnccng gncargaryt nwsnaargay tgyggntayg gngarggngg ngaygcntay    120
tgyacngcnt gyccnccnmg nmgntayaar wsnwsntggg gncaycayaa rtgycarwsn    180
tgyathacnt gygcngtnat haaymgngtn caraargtna aytgyacngc nacnwsnaay    240
gcngtntgyg gngaytgyyt nccnmgntty taymgnaara cnmgnathgg nggnytncar    300
gaycargart gyathccntg yacnaarcar acnccnacnw sngargtnca rtgygcntty    360
carytnwsny tngtngargc ngaygcnccn acngtnccnc cncargargc nacnytngtn    420
gcnytngtnw snwsnytnyt ngtngtntty acnytngcnt tyytnggnyt nttyttyytn    480
taytgyaarc arttyttyaa ymgncaytgy carmgnggng gnytnytnca rttygargcn    540
gayaaracng cnaargarga rwsnytntty ccngtnccnc cnwsnaarga racnwsngcn    600
```

```
garwsncarg  tnwsngaraa  yathttycar  acncarccny  tnaayccnat  hytngargay     660
gaytgywsnw  snacnwsngg  nttyccnacn  cargarwsnt  tyacnatggc  nwsntgyacn     720
wsngarwsnc  aywsncaytg  ggtncaywsn  ccnathgart  gyacngaryt  ngayytncar     780
aarttywsnw  snwsngcnws  ntayacnggn  gcngaracny  tnggnggnaa  yacngtngar     840
wsnacnggng  aymgnytnga  rytnaaygtn  ccn

<222> LOCATION: (1)...(801)
<223> OTHER INFORMATION: n = A,T,C or G

<400> SEQUENCE: 30

| | | | | | |
|---|---|---|---|---|---|
| atggaytgyc | argaraayga | rtaytgggay | cartggggnm | gntgygtnac | ntgycarmgn | 60 |
| tgyggnccng | gncargaryt | nwsnaargay | tgyggntayg | gngarggngg | ngaygcntay | 120 |
| tgyacngcnt | gyccncccnmg | nmgntayaar | wsnwsntggg | gncaycayaa | rtgycarwsn | 180 |
| tgyathacnt | gygcngtnat | haaymgngtn | caraargtna | aytgyacngc | nacnwsnaay | 240 |
| gcngtntgyg | gngaytgyyt | nccnmgntty | taymgnaara | cnmgnathgg | nggnytncar | 300 |
| gaycargart | gyathccntg | yacnaarcar | acnccnacnw | sngargtnca | rtgygcntty | 360 |
| carytnwsny | tngtngargc | ngaygcnccn | acngtnccnc | cncargargc | nacnytngtn | 420 |
| gcnytnggng | gnytnytnca | rttygargcn | gayaaracng | cnaargarga | rwsnytntty | 480 |
| ccngtnccnc | cnwsnaarga | racnwsngcn | garwsncarg | tnwsngaraa | yathttycar | 540 |
| acncarccny | tnaayccnat | hytngargay | gaytgywsnw | snacnwsngg | nttyccnacn | 600 |
| cargarwsnt | tyacnatggc | nwsntgyacn | wsngarwsnc | aywsncaytg | ggtncaywsn | 660 |
| ccnathgart | gyacngaryt | ngayytncar | aarttywsnw | snwsngcnws | ntayacnggn | 720 |
| gcngaracny | tnggnggnaa | yacngtngar | wsnacnggng | aymgnytnga | rytnaaygtn | 780 |
| ccnttygarg | tnccnwsncc | n | | | | 801 |

<210> SEQ ID NO 31
<211> LENGTH: 529
<212> TYPE: DNA
<213> ORGANISM: Homo sapiens
<220> FEATURE:
<221> NAME/KEY: misc_feature
<222> LOCATION: (1)...(529)
<223> OTHER INFORMATION: n = A,T,C or G

<400> SEQUENCE: 31

| | | | | | |
|---|---|---|---|---|---|
| ggattcnatn | nctgaggntg | natggcnttc | nagttnwgas | tkagtggagg | cagatgcasc | 60 |
| cacagtgccc | gcctcaggag | gycacacttg | ttgcrmtggt | gagcagcstg | ctagtggtgt | 120 |
| ttrccctggc | cttcctgggg | ctcttcttcc | tcwacygcaa | gcagttcttc | aacagacatt | 180 |
| gycagcsgng | gaggtttgct | gcagtttgag | gctgataaaa | cagcaaagga | ggaatctstm | 240 |
| ttycycgtgc | cacccagcaa | ggagaccagt | gctgagtccc | aagtgagtga | aacatyttt | 300 |
| cakacccagm | cacttaaccc | tatcctyrag | gacgactgca | rctcgactag | tggyttcccc | 360 |
| acacaggart | mctttaccat | ggcctyctgc | acctyagaga | gccactscca | ctgggwccac | 420 |
| arccccatcg | aatgcacaka | gctggacctg | caaaagtttt | ccagctctgc | ctcctatact | 480 |
| ggagctgara | ccttgggggg | aaacacagnc | aaaagcactg | ganacaggg | | 529 |

<210> SEQ ID NO 32
<211> LENGTH: 401
<212> TYPE: DNA
<213> ORGANISM: Homo sapiens
<220> FEATURE:
<221> NAME/KEY: misc_feature
<222> LOCATION: (1)...(401)
<223> OTHER INFORMATION: n = A,T,C or G

<400> SEQUENCE: 32

| | | | | | |
|---|---|---|---|---|---|
| cagttgagct | tagtggaggc | agatgcaccc | acagtgcccc | ctcaggaggc | cacacttgtt | 60 |
| gsactggagg | tttgctgcag | tttgaggctg | ataaaacagc | aaaggaggaa | tctctcttns | 120 |

```
ccgtgccacc cagcaaggag accagtgctg agtcccaagt gagtgagaac atctttcaga      180
cccagccact taaccctatc ctcgaggacg actgcagctc gactagtggc ttccccacac      240
aggagtcctt taccatggcc tcctgcacct cagagagcca ctcccactgg gtccacagcc      300
ccatcgaatg cacagagctg gacctgcaaa agttttccag ctctgcctcc tatactggag      360
ctgagacctt gggggggaaac acagtcgaaa gcactggaga c                        401
```

<210> SEQ ID NO 33
<211> LENGTH: 528
<212> TYPE: DNA
<213> ORGANISM: Homo sapiens

<400> SEQUENCE: 33

```
ctctgaggtt caatgtgcct tccagttgag cttagtggag gcagatgcac ccacagtgcc      60
ccctcaggag gccacacttg ttgcactggt gagcagcctg ctagtggtgt ttaccctggc     120
cttcctgggg ctcttcttcc tctactgcaa gcagttcttc aacagacatt gccagcgtgt     180
tgcaggaggt ttgctgcagt ttgaggctga taaaacagca aaggaggaat ctctcttccc     240
cgtgccaccc agcaaggaga ccagtgctga gtcccaagtg agtgagaaca tctttcagac     300
ccagccactt aaccctatcc tcgaggacga ctgcagctcg actagtggct ccccacaca     360 ggagtccttt accatggcct cctgcacctc agagagccac tcccactggg tccacagccc     420
catcgaatgc acagagctgg acctgcaaaa gttttccagc tctgcctcct atactggagc     480
tgagaccttg ggggggaaaca cagtcgaaag cactggagac aggctgga                 528
```

<210> SEQ ID NO 34
<211> LENGTH: 175
<212> TYPE: PRT
<213> ORGANISM: Homo sapiens

<400> SEQUENCE: 34

```
Ser Glu Val Gln Cys Ala Phe Gln Leu Ser Leu Val Glu Ala Asp Ala
 1               5                  10                  15

Pro Thr Val Pro Pro Gln Glu Ala Thr Leu Val Ala Leu Val Ser Ser
             20                  25                  30

Leu Leu Val Val Phe Thr Leu Ala Phe Leu Gly Leu Phe Phe Leu Tyr
         35                  40                  45

Cys Lys Gln Phe Phe Asn Arg His Cys Gln Arg Val Ala Gly Gly Leu
     50                  55                  60

Leu Gln Phe Glu Ala Asp Lys Thr Ala Lys Glu Ser Leu Phe Pro
 65                  70                  75                  80

Val Pro Pro Ser Lys Glu Thr Ser Ala Glu Ser Gln Val Ser Glu Asn
                 85                  90                  95

Ile Phe Gln Thr Gln Pro Leu Asn Pro Ile Leu Glu Asp Asp Cys Ser
            100                 105                 110

Ser Thr Ser Gly Phe Pro Thr Gln Glu Ser Phe Thr Met Ala Ser Cys
        115                 120                 125

Thr Ser Glu Ser His Ser His Trp Val His Ser Pro Ile Glu Cys Thr
    130                 135                 140

Glu Leu Asp Leu Gln Lys Phe Ser Ser Ser Ala Ser Tyr Thr Gly Ala
145                 150                 155                 160

Glu Thr Leu Gly Gly Asn Thr Val Glu Ser Thr Gly Asp Arg Leu
                165                 170                 175
```

<210> SEQ ID NO 35
<211> LENGTH: 299
<212> TYPE: PRT
<213> ORGANISM: Homo sapiens

<400> SEQUENCE: 35

Met Asp Cys Gln Glu Asn Glu Tyr Trp Asp Gln Trp Gly Arg Cys Val
1               5                   10                  15
Thr Cys Gln Arg Cys Gly Pro Gly Gln Glu Leu Ser Lys Asp Cys Gly
            20                  25                  30
Tyr Gly Glu Gly Gly Asp Ala Tyr Cys Thr Ala Cys Pro Pro Arg Arg
        35                  40                  45
Tyr Lys Ser Ser Trp Gly His His Lys Cys Gln Ser Cys Ile Thr Cys
    50                  55                  60
Ala Val Ile Asn Arg Val Gln Lys Val Asn Cys Thr Ala Thr Ser Asn
65                  70                  75                  80
Ala Val Cys Gly Asp Cys Leu Pro Arg Phe Tyr Arg Lys Thr Arg Ile
                85                  90                  95
Gly Gly Leu Gln Asp Gln Glu Cys Ile Pro Cys Thr Lys Gln Thr Pro
            100                 105                 110
Thr Ser Glu Val Gln Cys Ala Phe Gln Leu Ser Leu Val Glu Ala Asp
        115                 120                 125
Ala Pro Thr Val Pro Pro Gln Glu Ala Thr Leu Val Ala Leu Val Ser
    130                 135                 140
Ser Leu Leu Val Val Phe Thr Leu Ala Phe Leu Gly Leu Phe Phe Leu
145                 150                 155                 160
Tyr Cys Lys Gln Phe Phe Asn Arg His Cys Gln Arg Val Ala Gly Gly
                165                 170                 175
Leu Leu Gln Phe Glu Ala Asp Lys Thr Ala Lys Glu Glu Ser Leu Phe
            180                 185                 190
Pro Val Pro Pro Ser Lys Glu Thr Ser Ala Glu Ser Gln Val Ser Glu
        195                 200                 205
Asn Ile Phe Gln Thr Gln Pro Leu Asn Pro Ile Leu Glu Asp Asp Cys
    210                 215                 220
Ser Ser Thr Ser Gly Phe Pro Thr Gln Glu Ser Phe Thr Met Ala Ser
225                 230                 235                 240
Cys Thr Ser Glu Ser His Ser His Trp Val His Ser Pro Ile Glu Cys
                245                 250                 255
Thr Glu Leu Asp Leu Gln Lys Phe Ser Ser Ser Ala Ser Tyr Thr Gly
            260                 265                 270
Ala Glu Thr Leu Gly Gly Asn Thr Val Glu Ser Thr Gly Asp Arg Leu
        275                 280                 285
Glu Leu Asn Val Pro Phe Glu Val Pro Ser Pro
    290                 295

<210> SEQ ID NO 36
<211> LENGTH: 431
<212> TYPE: DNA
<213> ORGANISM: Homo sapiens

<400> SEQUENCE: 36 ctc tga ggt tca atg tgc ctt cca gtt gag ctt agt gga ggc aga tgc     48 acc cac agt gcc ccc tca gga ggc cac act tgt tgc act gga ggt ttg     96 ctg cag ttt gag gct gat aaa aca gca aag gag gaa tct ctc ttc ccc    144 gtg cca ccc agc aag gag acc agt gct gag tcc caa gtg agt gag aac    192

```
atc ttt cag acc cag cca ctt aac cct atc ctc gag gac gac tgc agc      240
tcg act agt ggc ttc ccc aca cag gag tcc ttt acc atg gcc tcc tgc      288
acc tca gag agc cac tcc cac tgg gtc cac agc ccc atc gaa tgc aca      336
gag ctg gac ctg caa aag ttt tcc agc tct gcc tcc tat act gga gct      384
gag acc ttg ggg gga aac aca gtc gaa agc act gga gac agg ctg ga       431
```

<210> SEQ ID NO 37
<211> LENGTH: 142
<212> TYPE: PRT
<213> ORGANISM: Homo sapiens

<400> SEQUENCE: 37

```
Leu Gly Ser Met Cys Leu Pro Val Glu Leu Ser Gly Arg Cys Thr
 1               5                  10                  15

His Ser Ala Pro Ser Gly Gly His Thr Cys Cys Thr Gly Gly Leu Leu
            20                  25                  30

Gln Phe Glu Ala Asp Lys Thr Ala Lys Glu Glu Ser Leu Phe Pro Val
        35                  40                  45

Pro Pro Ser Lys Glu Thr Ser Ala Glu Ser Gln Val Ser Glu Asn Ile
    50                  55                  60

Phe Gln Thr Gln Pro Leu Asn Pro Ile Leu Glu Asp Asp Cys Ser Ser
65                  70                  75                  80

Thr Ser Gly Phe Pro Thr Gln Glu Ser Phe Thr Met Ala Ser Cys Thr
                85                  90                  95

Ser Glu Ser His Ser His Trp Val His Ser Pro Ile Glu Cys Thr Glu
            100                 105                 110

Leu Asp Leu Gln Lys Phe Ser Ser Ser Ala Ser Tyr Thr Gly Ala Glu
        115                 120                 125

Thr Leu Gly Gly Asn Thr Val Glu Ser Thr Gly Asp Arg Leu
    130                 135                 140
```

<210> SEQ ID NO 38
<211> LENGTH: 173
<212> TYPE: PRT
<213> ORGANISM: Homo sapiens

<400> SEQUENCE: 38

```
Met Asp Cys Gln Glu Asn Glu Tyr Trp Asp Gln Trp Gly Arg Cys Val
 1               5                  10                  15

Thr Cys Gln Arg Cys Gly Pro Gly Gln Glu Leu Ser Lys Asp Cys Gly
            20                  25                  30

Tyr Gly Glu Gly Gly Asp Ala Tyr Cys Thr Ala Cys Pro Pro Arg Arg
        35                  40                  45

Tyr Lys Ser Ser Trp Gly His His Lys Cys Gln Ser Cys Ile Thr Cys
    50                  55                  60

Ala Val Ile Asn Arg Val Gln Lys Val Asn Cys Thr Ala Thr Ser Asn
65                  70                  75                  80

Ala Val Cys Gly Asp Cys Leu Pro Arg Phe Tyr Arg Lys Thr Arg Ile
                85                  90                  95

Gly Gly Leu Gln Asp Gln Glu Cys Ile Pro Cys Thr Lys Gln Thr Pro
            100                 105                 110

Thr Ser Glu Val Gln Cys Ala Phe Gln Leu Ser Leu Val Glu Ala Asp
        115                 120                 125

Ala Pro Thr Val Pro Pro Gln Glu Ala Thr Leu Val Ala Leu Glu Val
```

```
            130                 135                 140
Cys Cys Ser Leu Arg Leu Ile Lys Gln Gln Arg Arg Asn Leu Ser Ser
145                 150                 155                 160

Pro Cys His Pro Ala Arg Arg Pro Val Leu Ser Pro Lys
                165                 170

<210> SEQ ID NO 39
<211> LENGTH: 519
<212> TYPE: DNA
<213> ORGANISM: Artificial Sequence
<220> FEATURE:
<223> OTHER INFORMATION: degenerate polynucleotide sequence
<220> FEATURE:
<221> NAME/KEY: misc_feature
<222> LOCATION: (1)...(519)
<223> OTHER INFORMATION: n = A,T,C or G

<400> SEQUENCE: 39
atggaytgyc argaraayga rtaytgggay cartggggnm gntgygtnac ntgycarmgn      60
tgyggnccng gncargaryt nwsnaargay tgyggntayg gngarggngg ngaygcntay     120
tgyacngcnt gyccnccnmg nmgntayaar wsnwsntggg gncaycayaa rtgycarwsn     180
tgyathacnt gygcngtnat haaymgngtn caraargtna aytgyacngc nacnwsnaay     240
gcngtntgyg gngaytgyyt ccnmgntty taymgnaara cnmgnathgg nggnytncar     300
gaycargart gyathcnctg yacnaarcar acnccnacnw sngargtnca rtgygcntty     360
carytnwsny tngtngargc ngaygcnccn acngtccnc cncargargc nacnytngtn     420
gcnytngarg tntgytgyws nytnmgnytn athaarcarc armgnmgnaa yytnwsnwsn     480
ccntgycayc cngcnmgnmg nccngtnytn wsnccnaar                           519

<210> SEQ ID NO 40
<211> LENGTH: 47
<212> TYPE: DNA
<213> ORGANISM: Artificial Sequence
<220> FEATURE:
<223> OTHER INFORMATION: oligonucleotide ZC26463

<400> SEQUENCE: 40
atgcattaac cctcactaaa gggccttcct ggggctcttc ttcctct                   47

<210> SEQ ID NO 41
<211> LENGTH: 46
<212> TYPE: DNA
<213> ORGANISM: Artificial Sequence
<220> FEATURE:
<223> OTHER INFORMATION: Oligonucleotide sequence ZC 26464

<400> SEQUENCE: 41
taatacgact cactataggg aggggcccct gctgctgttg tggtat                    46

<210> SEQ ID NO 42
<211> LENGTH: 49
<212> TYPE: DNA
<213> ORGANISM: Artificial Sequence
<220> FEATURE:
<223> OTHER INFORMATION: Oligonucleotide ZC24670

<400> SEQUENCE: 42
atgcattaac cctcactaaa gggacctgtg ctgtcatcaa tcgtgttca                 49

<210> SEQ ID NO 43
<211> LENGTH: 47
```

```
<212> TYPE: DNA
<213> ORGANISM: Artificial Sequence
<220> FEATURE:
<223> OTHER INFORMATION: Oligonucleotide sequence ZC 26471

<400> SEQUENCE: 43
taatacgact cactataggg aggcccccaa ggtctcagct ccagtat          47

<210> SEQ ID NO 44
<211> LENGTH: 657
<212> TYPE: DNA
<213> ORGANISM: murine

<400> SEQUENCE: 44
ggtggcatct ctcttccaat tggtctgatt gttggagtga catcactggg tctgctgatg    60
ttaggactgg tgaactgcat catcctggtg cagaggaaaa agaagccctc ctgcctacaa   120
agagatgcca aggtgcctca tgtgcctgat gagaaatccc aggatgcagt aggccttgag   180
cagcagcacc tgttgaccac agcacccagt tccagcagca gctccctaga gagctcagcc   240
agcgctgggg accgaagggc gcccctggg ggccatcccc aagcaagagt catggcggag    300
gcccaagggt ttcaggaggc ccgtgccagc tccaggattt cagattcttc ccacggaagc   360
cacgggaccc acgtcaacgt cacctgcatc gtgaacgtct gtagcagctc tgaccacagt   420
tctcagtgct cttcccaagc cagcgccaca gtgggagacc cagatgccaa gccctcagcg   480
tccccaaagg atgagcaggt ccccttctct caggaggagt gtccgtctca gtcccgtgt    540 gagactacag agacactgca gagccatgag aagcccttgc ccttggtgt gccggatatg    600 ggcatgaagc ccagccaagc tggctggttt gatcagattg cagtcaaagt ggcctga      657

<210> SEQ ID NO 45
<211> LENGTH: 824
<212> TYPE: DNA
<213> ORGANISM: Artificial Sequence
<220> FEATURE:
<223> OTHER INFORMATION: artificial cDNA sequence

<400> SEQUENCE: 45
ggtaccgaat tgtacgcgta tggggacttc ccatatcaat cagggacttt ccgctgggga    60 cttttccggtc tgactcatgc ttctgactca tgcttgggtg acatcatctc gactagtcgt   120
accttcccgt aaatccctcc ccttcccgga attacacacg cgtatttccc agaaaaggaa   180
ctgtagattt ctaggaattc aatccttggc cacgcgttta caccggaagt tttccatatt   240
aggaattcct tccggtttcc tttctcgagg ccaccgtggt tgagcccgac actcattcat   300
aaaacgcttg ttataaaagc agtggctgcg gcgccttcgt actccaaccg catctgcagc   360
gagcaactga aagccaagg atccaggctg aattcatggg tctcaacccc cagctagttg   420
tcatcctgct cttctttctc gaatgtacca ggagccatat ccacggatgc gacaaaaatc   480
acttgagaga gatcatcggc attttgaacg aggtcacagg agaagggacg ccatgcacgg   540
agatggatgt gccaaacgtc ctcacagcaa cgaagaacac cacagagagt gagctcgtct   600
gtagggcttc caaggtgctt cgcatatttt atttaaaaca tgggaaaact ccatgcttga   660
agaagaactc tagtgttctc atggagctgc agagactctt tcgggctttt cgatgcctgg   720
attcatcgat aagctgcacc atgaatgagt ccaagtccac atcactgaaa gacttcctgg   780
aaagcctaaa gagcatcatg caaatggatt actcgtagtc taga                   824

<210> SEQ ID NO 46
```

```
<211> LENGTH: 47
<212> TYPE: DNA
<213> ORGANISM: Artificial Sequence
<220> FEATURE:
<223> OTHER INFORMATION: Oligonucleotide sequence ZC28835

<400> SEQUENCE: 46
taatacgact cactataggg aggcccccaa ggtctcagct ccagtat          47

<210> SEQ ID NO 47
<211> LENGTH: 27
<212> TYPE: DNA
<213> ORGANISM: Artificial Sequence
<220> FEATURE:
<223> OTHER INFORMATION: Oligonucleotide sequence ZC 28836

<400> SEQUENCE: 47
gcaccggtgg cctcctgagg gggcact                                27

<210> SEQ ID NO 48
<211> LENGTH: 29
<212> TYPE: DNA
<213> ORGANISM: Artificial Sequence
<220> FEATURE:
<223> OTHER INFORMATION: Oligonucleotide ZC 28830

<400> SEQUENCE: 48
gcaccggtgg catctctctt ccaattggt                              29

<210> SEQ ID NO 49
<211> LENGTH: 29
<212> TYPE: DNA
<213> ORGANISM: Artificial Sequence
<220> FEATURE:
<223> OTHER INFORMATION: Oligonucleotide ZC 28837

<400> SEQUENCE: 49
gctctagagg ggtcaggcca ctttgactg                              29

<210> SEQ ID NO 50
<211> LENGTH: 1081
<212> TYPE: DNA
<213> ORGANISM: Artificial Sequence
<220> FEATURE:
<223> OTHER INFORMATION: DNA construct

<400> SEQUENCE: 50
atggattgcc aagaaaatga gtactgggac caatggggac ggtgtgtcac ctgccaacgg    60
tgtggtcctg acaggagct atccaaggat tgtggttatg gagagggtgg agatgcctac   120
tgcacagcct gccctcctcg caggtacaaa agcagctggg gccaccacaa atgtcagagt   180
tgcatcacct gtgctgtcat caatcgtgtt cagaaggtca actgcacagc tacctctaat   240
gctgtctgtg gggactgttt gcccaggttc taccgaaaga cacgcattgg aggcctgcag   300
gaccaagagt gcatcccgtg cacgaagcag acccccacct ctgaggttca atgtgccttc   360
cagttgagct tagtggaggc agatgcaccc acagtgcccc ctcaggaggt cacccgttggc   420 atctctcttc caattggtct gattgttgga gtgacatcac tgggtctgct gatgttagga   480
ctggtgaact gcatcatcct ggtgcagagg aaaaagaagc cctcctgcct acaaagagat   540
gccaaggtgc ctcatgtgcc tgatgagaaa tcccaggatg cagtaggcct tgagcagcag   600
cacctgttga ccacagcacc cagttccagc agcagctccc tagagagctc agccagcgct   660
ggggaccgaa gggcgccccc tgggggccat ccccaagcaa gagtcatggc ggaggcccaa   720
```

```
gggtttcagg aggcccgtgc cagctccagg atttcagatt cttcccacgg aagccacggg    780
acccacgtca acgtcacctg catcgtgaac gtctgtagca gctctgacca cagttctcag    840
tgctcttccc aagccagcgc cacagtggga gacccagatg ccaagccctc agcgtcccca    900
aaggatgagc aggtcccctt ctctcaggag gagtgtccgt ctcagtcccc gtgtgagact    960
acagagacac tgcagagcca tgagaagccc ttgccccttg gtgtgccgga tatgggcatg   1020
aagcccagcc aagctggctg gtttgatcag attgcagtca aagtggcctg accctctag   1080 a                                                                   1081
```